(12) United States Patent
Wang et al.

(10) Patent No.: US 8,772,005 B2
(45) Date of Patent: Jul. 8, 2014

(54) LACCASES, COMPOSITIONS AND METHODS OF USE

(75) Inventors: Huaming Wang, Fremont, CA (US); Joseph C. McAuliffe, Sunnyvale, CA (US)

(73) Assignee: Danisco US Inc., Palo Alto, CA (US)

( * ) Notice: Subject to any disclaimer, the term of this patent is extended or adjusted under 35 U.S.C. 154(b) by 408 days.

(21) Appl. No.: 13/312,840

(22) Filed: Dec. 6, 2011

(65) Prior Publication Data

US 2012/0151682 A1 Jun. 21, 2012

Related U.S. Application Data

(63) Continuation of application No. 11/954,804, filed on Dec. 12, 2007, now Pat. No. 8,105,812.

(60) Provisional application No. 60/875,518, filed on Dec. 18, 2006, provisional application No. 60/875,454, filed on Dec. 18, 2006.

(51) Int. Cl.
*C12N 9/02* (2006.01)

(52) U.S. Cl.
USPC .......................................... 435/189; 536/23.2

(58) Field of Classification Search
CPC ...................... C12N 9/0061; C12Y 110/03002
USPC .......................................... 435/189; 536/23.2
See application file for complete search history.

(56) References Cited

U.S. PATENT DOCUMENTS

| | | | |
|---|---|---|---|
| 5,752,980 A | 5/1998 | Pedersen et al. | |
| 5,861,271 A | 1/1999 | Fowler et al. | |
| 7,279,564 B2 | 10/2007 | De Nobel et al. | |
| 7,354,752 B2 | 4/2008 | Dunn-Coleman et al. | |
| 7,413,877 B2 | 8/2008 | Collier et al. | |
| 7,413,887 B2 | 8/2008 | Dunn-Coleman et al. | |
| 2006/0154843 A1 | 7/2006 | Wang et al. | |
| 2008/0196173 A1 | 8/2008 | Wang et al. | |

FOREIGN PATENT DOCUMENTS

| | | |
|---|---|---|
| EP | 0 238 023 A2 | 9/1987 |
| EP | 0 504 005 B1 | 9/1992 |
| JP | 02238885 A | 9/1990 |
| WO | WO 92/01046 A1 | 1/1992 |
| WO | WO 95/01426 A1 | 1/1995 |
| WO | WO 95/33836 A1 | 12/1995 |
| WO | WO 95/33837 A1 | 12/1995 |
| WO | WO 96/00290 A1 | 1/1996 |
| WO | WO 96/00787 A1 | 1/1996 |
| WO | WO 96/12845 A1 | 5/1996 |
| WO | WO 97/08325 A2 | 3/1997 |
| WO | WO 97/11217 A1 | 3/1997 |
| WO | WO 2005/001036 A2 | 1/2005 |
| WO | WO 2005/093050 A2 | 10/2005 |

OTHER PUBLICATIONS

Altschul, S.F. et al. "Basic local alignment search tool." *J. Mol. Biol* 215(3): 403-410, 1990.

Altschul, S.F. et al. "Gapped BLAST and PSI—BLAST: a new generation of protein database search programs." *Nucleic Acids Res.* 25(17): 3389-3402, 1997.

Lyashenko, A.V. et al. "Purification, crystallization and preliminary X-ray study of the fungal laccase from *Cerrena maxima*." *Acta Crystallogr Sect F Struct Biol Cryst Commun.* F62(Pt 10): 954-957, Oct. 1, 2006.

Mander, G.J. et al. "Use of Laccase as a Novel, Versatile Reporter System in Filamentous Fungi." *Appl. Environ. Microbiol.* 72(7): 5020-5026, Jul. 1, 2006.

Michniewicz, A. et al. "The white-rot fungus *Cerrena unicolor* strain 137 produces two laccase isoforms with different physico-chemical and catalytic properties." *Applied Microbiology and Biotechnology* 69(6): 682-688, Feb. 11, 2006.

Zhang, M. et al. "Characterization and decolorization ability of a laccase from *Panus rudis*." *Enzyme and Microbial Technology* 39(1): 92-97, Jun. 1, 2006.

Database UniProt. Laccase 1 precursor (EC:1.10.3.2). EBI accession No. Uniprot:Q2HWK1, Mar. 21, 2006.

*Primary Examiner* — Tekchand Saidha
(74) *Attorney, Agent, or Firm* — Danisco US Inc.

(57) ABSTRACT

Novel laccases, nucleic acid sequences encoding such laccases, and vectors and host cells for expressing the laccases are described. The novel laccase enzymes may be employed in conjunction with mediators to provide an improved method for bleaching denim fabrics.

7 Claims, 10 Drawing Sheets

Figure 7. Bleaching of soluble indigo using a *Thielavia* sp. laccase and a variety of mediators at 50 and 500 uM concentrations.

Figure 8. Bleaching of soluble indigo using a *Thielavia*, *Myceliophthora* and *Cerrena* sp. laccase and a variety of mediators at pH 5.

Figure 9. Bleaching of soluble indigo using a *Thielavia*, *Myceliophthora* and *Cerrena* sp. laccase and a variety of mediators at pH 7.

SEQUENCE LISTING

<160> NUMBER OF SEQ ID NOS: 77

<210> SEQ ID NO 1
<211> LENGTH: 2363
<212> TYPE: DNA
<213> ORGANISM: Cerrena unicolor

<400> SEQUENCE: 1

| | | | | | | |
|---|---|---|---|---|---|---|
| atgagctcaa | agctacttgc | tcttatcact | gtcgctctcg | tcttgccact | aggcaccgac | 60 |
| gccggcatcg | gtcctgttac | cgacttgcgc | atcaccaacc | aggatatcgc | tccagatggc | 120 |
| ttcacccgac | cagcggtact | agctgggggc | acattccctg | gagcacttat | taccggtcag | 180 |
| aaggtatggg | agatcaactt | ggttgaatag | agaaataaaa | gtgacaacaa | atccttatag | 240 |
| ggagacagct | tccaaatcaa | tgtcatcgac | gagcttaccg | atgccagcat | gttgacccag | 300 |
| acatccattg | tgagtataat | ttaggtccgc | tcttctggct | atcctttcta | actcttaccg | 360 |
| tctagcattg | gcacggcttc | tttcagaagg | gatctgcgtg | ggccgatggt | cctgccttcg | 420 |
| ttactcaatg | ccctatcgtc | accggaaatt | ccttcctgta | cgactttgat | gttcccgacc | 480 |
| aacctggtac | tttctggtac | catagtcact | tgtctactca | atattgcgat | ggtcttcgtg | 540 |
| gcccgttcgt | tgtatacgat | ccaaaggatc | ctaataaacg | gttgtacgac | attgacaatg | 600 |
| gtatgtgcat | catcatagag | atataattca | tgcagctact | gaccgtgact | gatgctgcca | 660 |
| gatcatacgg | ttattaccct | ggcagactgg | taccacgttc | tcgcaagaac | tgttgtcgga | 720 |
| gtcgcgtaag | tacagtctca | cttatagtgg | tcttcttact | cattttgaca | taggacaccc | 780 |
| gacgcaacct | tgatcaacgg | tttgggccgt | tctccagacg | ggccagcaga | tgctgagttg | 840 |
| gctgtcatca | acgttaaacg | cggcaaacgg | tatgttattg | aactcccgat | ttctccatac | 900 |
| acagtgaaat | gactgtctgg | tctagttatc | gatttcgtct | ggtctccatc | tcatgtgacc | 960 |
| ctaattacat | cttttctatc | gacaaccatt | ctatgactgt | catcgaagtc | gatggtgtca | 1020 |
| acacccaatc | cctgaccgtc | gattctattc | aaatcttcgc | aggccaacga | tactcgttcg | 1080 |
| tcgtaagtct | ctttgcacga | ttactgcttc | tttgtccatt | ctctgacctg | tttaaacagc | 1140 |
| tccatgccaa | ccgtcctgaa | acaactattg | gatcagggc | caaacctaat | atcggtacgg | 1200 |
| atactaccac | agacaacggc | atgaactctg | ccattctgcg | atacaacggc | gcacctgttg | 1260 |
| cggaaccgca | aactgttcaa | tctcccagtc | tcacccctttt | gctcgaacag | aaccttcgcc | 1320 |
| ctctcgtgta | cactcctgtg | gtatgtttca | aagcgttgta | atttgattgt | ggtcattcta | 1380 |
| acgttactgc | gtttgcatag | cctggaaacc | ctacgcctgg | cggcgccgat | attgtccata | 1440 |
| ctcttgactt | gagttttgtg | cggagtcaac | attcgtaaag | ataagagtgt | ttctaatttc | 1500 |
| ttcaataata | ggatgctggt | cgcttcagta | tcaacggtgc | ctcgttcctt | gatcctaccg | 1560 |
| tccccgttct | cctgcaaatt | tcagcggca | cgcagaatgc | acaagatcta | ctccctcctg | 1620 |
| gaagtgtgat | tcctctcgaa | ttaggcaagg | tcgtcgaatt | agtcatacct | gcaggtgtcg | 1680 |
| tcggtggacc | tcatccgttc | catctccatg | gggtacgtaa | cccgaactta | taacagtctt | 1740 |
| ggacttaccc | gctgacaagt | gcatagcata | acttctgggt | cgtgcgaagt | gccggaaccg | 1800 |
| accagtacaa | ctttaacgat | gccattctcc | gagacgtcgt | cagtatagga | ggaaccgggg | 1860 |
| atcaagtcac | cattcgtttc | gtggtatgtt | tcattcttgt | ggatgtatgt | gctctaggat | 1920 |
| actaaccggc | ttgcgcgtat | agaccgataa | ccccggaccg | tggttcctcc | attgccatat | 1980 |
| cgactggcac | ttggaagcgg | gtctcgctat | cgtatttgca | gagggaattg | aaaatactgc | 2040 |
| tgcgtctaat | ttaaccccc | gtacgcggtt | tccctcacat | cctggagcta | agcagcttac | 2100 |

```
taacatacat tgcagaggc ttgggatgag ctttgcccga agtataacgc gctcagcgca   2160
caaaagaagg ttgcatctaa gaaaggcact gccatctaat ttttgtaaca aacaaggagg   2220
gtctcttgta cttttattgg gatttctttc ttggggttta ttgttaaact tgactctact   2280
atgtttggaa gacgaaaggg gctcgcgcat ttatatacta tctctcttgg catcacctgc   2340
agctcaatcc ttcaaccacc taa                                           2363
```

<210> SEQ ID NO 2
<211> LENGTH: 523
<212> TYPE: PRT
<213> ORGANISM: Cerrena unicolor

<400> SEQUENCE: 2

```
Met Ser Ser Lys Leu Leu Ala Leu Ile Thr Val Ala Leu Val Leu Pro
1               5                   10                  15

Leu Gly Thr Asp Ala Gly Ile Gly Pro Val Thr Asp Leu Arg Ile Thr
            20                  25                  30

Asn Gln Asp Ile Ala Pro Asp Gly Phe Thr Arg Pro Ala Val Leu Ala
        35                  40                  45

Gly Gly Thr Phe Pro Gly Ala Leu Ile Thr Gly Gln Lys Gly Asp Ser
    50                  55                  60

Phe Gln Ile Asn Val Ile Asp Glu Leu Thr Asp Ala Ser Met Leu Thr
65                  70                  75                  80

Gln Thr Ser Ile His Trp His Gly Phe Phe Gln Lys Gly Ser Ala Trp
                85                  90                  95

Ala Asp Gly Pro Ala Phe Val Thr Gln Cys Pro Ile Val Thr Gly Asn
            100                 105                 110

Ser Phe Leu Tyr Asp Phe Asp Val Pro Asp Gln Pro Gly Thr Phe Trp
        115                 120                 125

Tyr His Ser His Leu Ser Thr Gln Tyr Cys Asp Gly Leu Arg Gly Pro
    130                 135                 140

Phe Val Val Tyr Asp Pro Lys Asp Pro Asn Lys Arg Leu Tyr Asp Ile
145                 150                 155                 160

Asp Asn Asp His Thr Val Ile Thr Leu Ala Asp Trp Tyr His Val Leu
                165                 170                 175

Ala Arg Thr Val Val Gly Val Ala Thr Pro Asp Ala Thr Leu Ile Asn
            180                 185                 190

Gly Leu Gly Arg Ser Pro Asp Gly Pro Ala Asp Ala Glu Leu Ala Val
        195                 200                 205

Ile Asn Val Lys Arg Gly Lys Arg Tyr Arg Phe Arg Leu Val Ser Ile
    210                 215                 220

Ser Cys Asp Pro Asn Tyr Ile Phe Ser Ile Asp Asn His Ser Met Thr
225                 230                 235                 240

Val Ile Glu Val Asp Gly Val Asn Thr Gln Ser Leu Thr Val Asp Ser
                245                 250                 255

Ile Gln Ile Phe Ala Gly Gln Arg Tyr Ser Phe Val Leu His Ala Asn
            260                 265                 270

Arg Pro Glu Asn Asn Tyr Trp Ile Arg Ala Lys Pro Asn Ile Gly Thr
        275                 280                 285

Asp Thr Thr Thr Asp Ser Gly Met Asn Ser Ala Ile Leu Arg Tyr Asn
    290                 295                 300

Gly Ala Pro Val Ala Glu Pro Gln Thr Val Gln Ser Pro Ser Leu Thr
305                 310                 315                 320
```

| | | | | | | | | | | | |
|---|---|---|---|---|---|---|---|---|---|---|---|
|Pro|Leu|Leu|Glu|Gln|Asn|Leu|Arg|Pro|Leu|Val|Tyr|Thr|Pro|Val|Pro|
| | | | |325| | | |330| | | |335| | | |

Gly Asn Pro Thr Pro Gly Gly Ala Asp Ile Val His Thr Leu Asp Leu
            340                345                350

Ser Phe Asp Ala Gly Arg Phe Ser Ile Asn Gly Ala Ser Phe Leu Asp
            355                360                365

Pro Thr Val Pro Val Leu Leu Gln Ile Leu Ser Gly Thr Gln Asn Ala
370                      375                380

Gln Asp Leu Leu Pro Pro Gly Ser Val Ile Pro Leu Glu Leu Gly Lys
385                      390                395                400

Val Val Glu Leu Val Ile Pro Ala Gly Val Gly Gly Pro His Pro
            405                410                415

Phe His Leu His Gly His Asn Phe Trp Val Val Arg Ser Ala Gly Thr
            420                425                430

Asp Gln Tyr Asn Phe Asn Asp Ala Ile Leu Arg Asp Val Val Ser Ile
            435                440                445

Gly Gly Thr Gly Asp Gln Val Thr Ile Arg Phe Val Thr Asp Asn Pro
450                      455                460

Gly Pro Trp Phe Leu His Cys His Ile Asp Trp His Leu Glu Ala Gly
465                      470                475                480

Leu Ala Ile Val Phe Ala Glu Gly Ile Glu Asn Thr Ala Ala Ser Asn
            485                490                495

Leu Thr Pro Gln Ala Trp Asp Glu Leu Cys Pro Lys Tyr Asn Ala Leu
            500                505                510

Ser Ala Gln Lys Lys Leu Asn Pro Ser Thr Thr
            515                520

<210> SEQ ID NO 3
<211> LENGTH: 2374
<212> TYPE: DNA
<213> ORGANISM: Cerrena unicolor

<400> SEQUENCE: 3

```
atgagctcaa agctacttgc tcttattact gtcgctctcg tcttgccact aggcactgac      60
gccggcatcg gtcctgttac cgacttgcgc atcaccaacc aggatatcgc tccagatggc     120
ttcacccgac cagctgtact ggctgggggc acattccccg agcactgat  taccggtcag     180
aaggtatggg agatcgattt cgttgaatag agaaatacaa ctgaaaacaa attcttatag     240
ggagacagct tccaaatcaa tgtcatcgac gagcttaccg atgccagcat gttgacccag     300
acatccattg tgagtataat atgggtccgc tcttctagct atcctttcta actcttaccc     360
tctagcattg gcacggcttc tttcagaagg gatctgcgtg gccgatggt  cctgccttcg     420
ttactcaatg tcctatcgtc accggaaatt ccttcctgta cgactttgat gtccccgacc     480
aacctggtac tttctggtac catagtcact tgtctactca atattgcgat ggtcttcggg     540
gcccgttcgt tgtatacgat ccaaaggatc taataaacg  ttgtacgac attgacaatg     600
gtatgtgcat catcataaaa atataattca tgcagctact gaccgcgact gatgctgcca     660
gatcatacgg ttattaccct ggcagactgg taccacgttc tcgcacgaac tgttgtcgga     720
gtcgcgtaag tacagtctga cttatagtgg tcttcttact cattttgaca taggacaccc     780
gacgcaacct tgatcaacgg tttgggccgt ctccagacg  ggccagcaga tgctgagttg     840
gctgtcatca cgttaaacg  cggcaaacgg tatgtcattg aactcccgat ttctccattc     900
acattgaaat gactgtctgg tctagttatc gattccgtct ggtctccatc tcatgtgacc     960
```

```
ctaattacat cttttctatc gacaaccatt ctatgactgt catcgaagtc gatggtgtca    1020
acacccaatc cctgaccgtc gattctatcc aaatcttcgc aggccaacgc tactcgttcg    1080
tcgtaagtct ctttgaatgg ttggtgcttt ttctgtccat tctctaacct gtttatacag    1140
ctccatgcca accgtcctga aaacaactat tggatcaggg ccaaacctaa tatcggtacg    1200
gatactacca cagacaacgg catgaactct gccattctgc gatacaacgg cgcacctgtt    1260
gcggaaccgc aaactgttca atctcccagt ctcacccctt tgctcgaaca gaaccttcgc    1320
cctctcgtgt acactcctgt ggtatgtttc aaagcgttgt aatttgattg tggtcattct    1380
aacgttactg cctttgcaca gcctggaaat cctacgcctg cggggccga tattgtccat    1440 actcttgact tgagttttgt gcggagtcaa cattcgtaaa gataagagtg tttctaattt    1500
cttcaataat aggatgctgg tcgcttcagt atcaacggtg cctcgttcct tgatcctacc    1560
gtccctgttc tcctgcaaat tctcagcggc acgcagaatg cacaagatct actcoctcct    1620 ggaagtgtga ttcctctcga attaggcaag gtcgtcgaat tagtcatacc tgcaggtgtt    1680
gtcggtggac ctcatccgtt ccatctccat ggggtacgta acccgaactt ataacagtct    1740
tggacttacc cgctgacaag tgtatagcat aacttctggg tcgtgcgaag tgccggaacc    1800
gaccagtaca actttaacga tgccattctc cgagacgtcg tcagtatagg aggaaccgag    1860
gatcaagtca ccattcgatt cgtggtatat acttcattct tgtggatgta tgtgctctag    1920
gatactaact ggcttgcgcg tatagaccga taacccccgga ccgtggttcc tccattgcca    1980
tatcgactgg cacttggaag cgggtctcgc tatcgtattt gcagagggaa ttgaaaatac    2040
tgctgcgtct aatccaaccc cccgtatgcg gtttcccaca cattctgaat ctaagcagct    2100
tactaatata catttgcaga ggcttgggat gagctttgcc cgaagtataa cgcgctcaac    2160
gcacaaaaga aggttgcatc taagaaaggc actgccatct aatccttgta acaaacaagg    2220
agggtctctt gtacttttat tgggatttat ttcttggggt ttattgttca acttgattct    2280
actatgtttg gaagtagcga ttacgaaagg ggcttgcgca tttatatacc atctttcttg    2340
gcaccacctg cagctcaatc cttcaaccac ctaa                                2374
```

<210> SEQ ID NO 4
<211> LENGTH: 523
<212> TYPE: PRT
<213> ORGANISM: Cerrena unicolor

<400> SEQUENCE: 4

```
Met Ser Ser Lys Leu Leu Ala Leu Ile Thr Val Ala Leu Val Leu Pro
1               5                   10                  15

Leu Gly Thr Asp Ala Gly Ile Gly Pro Val Thr Asp Leu Arg Ile Thr
            20                  25                  30

Asn Gln Asp Ile Ala Pro Asp Gly Phe Thr Arg Pro Ala Val Leu Ala
        35                  40                  45

Gly Gly Thr Phe Pro Gly Ala Leu Ile Thr Gly Gln Lys Gly Asp Ser
    50                  55                  60

Phe Gln Ile Asn Val Ile Asp Glu Leu Thr Asp Ala Ser Met Leu Thr
65                  70                  75                  80

Gln Thr Ser Ile His Trp His Gly Phe Phe Gln Lys Gly Ser Ala Trp
                85                  90                  95

Ala Asp Gly Pro Ala Phe Val Thr Gln Cys Pro Ile Val Thr Gly Asn
            100                 105                 110

Ser Phe Leu Tyr Asp Phe Asp Val Pro Asp Gln Pro Gly Thr Phe Trp
        115                 120                 125
```

Tyr His Ser His Leu Ser Thr Gln Tyr Cys Asp Gly Leu Arg Gly Pro
130                 135                 140

Phe Val Val Tyr Asp Pro Lys Asp Pro Asn Lys Arg Leu Tyr Asp Ile
145                 150                 155                 160

Asp Asn Asp His Thr Val Ile Thr Leu Ala Asp Trp Tyr His Val Leu
                165                 170                 175

Ala Arg Thr Val Val Gly Val Ala Thr Pro Asp Ala Thr Leu Ile Asn
            180                 185                 190

Gly Leu Gly Arg Ser Pro Asp Gly Pro Ala Asp Ala Glu Leu Ala Val
        195                 200                 205

Ile Asn Val Lys Arg Gly Lys Arg Tyr Arg Phe Arg Leu Val Ser Ile
210                 215                 220

Ser Cys Asp Pro Asn Tyr Ile Phe Ser Ile Asp Asn His Ser Met Thr
225                 230                 235                 240

Val Ile Glu Val Asp Gly Val Asn Thr Gln Ser Leu Thr Val Asp Ser
                245                 250                 255

Ile Gln Ile Phe Ala Gly Gln Arg Tyr Ser Phe Val Leu His Ala Asn
            260                 265                 270

Arg Pro Glu Asn Asn Tyr Trp Ile Arg Ala Lys Pro Asn Ile Gly Thr
        275                 280                 285

Asp Thr Thr Thr Asp Asn Gly Met Asn Ser Ala Ile Leu Arg Tyr Asn
290                 295                 300

Gly Ala Pro Val Ala Glu Pro Gln Thr Val Gln Ser Pro Ser Leu Thr
305                 310                 315                 320

Pro Leu Leu Glu Gln Asn Leu Arg Pro Leu Val Tyr Thr Pro Val Pro
                325                 330                 335

Gly Asn Pro Thr Pro Gly Gly Ala Asp Ile Val His Thr Leu Asp Leu
            340                 345                 350

Ser Phe Asp Ala Gly Arg Phe Ser Ile Asn Gly Ala Ser Phe Leu Asp
        355                 360                 365

Pro Thr Val Pro Val Leu Leu Gln Ile Leu Ser Gly Thr Gln Asn Ala
370                 375                 380

Gln Asp Leu Leu Pro Pro Gly Ser Val Ile Pro Leu Glu Leu Gly Lys
385                 390                 395                 400

Val Val Glu Leu Val Ile Pro Ala Gly Val Gly Gly Pro His Pro
                405                 410                 415

Phe His Leu His Gly His Asn Phe Trp Val Val Arg Ser Ala Gly Thr
            420                 425                 430

Asp Gln Tyr Asn Phe Asn Asp Ala Ile Leu Arg Asp Val Val Ser Ile
        435                 440                 445

Gly Gly Thr Glu Asp Gln Val Thr Ile Arg Phe Val Thr Asp Asn Pro
450                 455                 460

Gly Pro Trp Phe Leu His Cys His Ile Asp Trp His Leu Glu Ala Gly
465                 470                 475                 480

Leu Ala Ile Val Phe Ala Glu Gly Ile Glu Asn Thr Ala Ala Ser Asn
                485                 490                 495

Pro Thr Pro Gln Ala Trp Asp Glu Leu Cys Pro Lys Tyr Asn Ala Leu
            500                 505                 510

Asn Ala Gln Lys Lys Leu Asn Pro Ser Thr Thr
        515                 520

<210> SEQ ID NO 5
<211> LENGTH: 2173

<212> TYPE: DNA
<213> ORGANISM: Cerrena unicolor

<400> SEQUENCE: 5

```
atgtctcttc ttcgtagctt gacctccctc atcgtactag tcattggtgc atttgctgca      60
atcggtccag tcactgacct acatatagtg aaccagaatc tcgacccaga tggtttcaac     120
cgccccactg tactcgcagg tggtactttc cccggtcctc tgattcgtgg taacaaggta     180
cgcttcataa ccgccctccg tagacgtagg cttcggctga catgaccatc atctgtaggg     240
agataacttt aaaattaatg tgattgacga cttgacagag cacagtatgc tcaaggctac     300
gtccatcgta agtccctgat taacgtttca cctggtcata tcgctcaacg tctcgaagca     360
ctggcatggg ttcttccaga agggaaccaa ctgggccgat ggccccgcct tgtcaccca      420
atgtcctatc acatcaggaa acgccttcct gtatgatttc aacgttccgg accaagctgg     480
tactttctgg taccacagcc atctctctac acagtattgt gacggtcttc gtggtgcctt     540
tgtcgtctat gatcctaatg atcccaacaa gcaactctat gatgttgata acggcaagtt     600
ccttgcatat ttcatttcta tcatatcctc acctgtattg gcacagaaag caccgtgatt     660
accttggctg attggtatca tgcccttgct cagactgtca ctggtgtcgc gtgagtgaca     720
aatggccctc aattgttcac atattttcct gattatcata tgatagagta tctgatgcaa     780
cgttgatcaa cggattggga cgttcggcca ccggccccgc aaatgcccct ctggcggtca     840
tcagtgtcga gcggaataag aggtcagttc cataattatg attatttccc gcgttacttc     900
ctaacaatta tttttgtatc cctccacaga tatcgtttcc gattggtttc tatttcttgc     960
gaccctaact ttatttctc aattgaccac cacccaatga ccgtaattga gatggacggt    1020
gttaataccc aatctatgac cgtagattcg atccaaatat tcgcaggtca acgatattca    1080
tttgtcgtag gttattataa actgcccacc gatcatctct cacgtaactg ttatagatgc    1140
aagccaacca accagttgga aattattgga tccgcgctaa acctaatgtt gggaacacaa    1200
cttttccttgg aggcctgaac tccgctatat tacgatatgt gggagcccct gaccaagaac    1260
cgaccactga ccaaacaccc aactctacac cgctcgttga ggcgaaccta cgacccctcg    1320
tctatactcc tgtggtatgt tgttctcgtt acatatacca aacctaatat gaagactgaa    1380
cggatctact agccgggaca gccattcccc ggcggtgctg atatcgtcaa gaacttagct    1440
ttgggtttcg tacgtgtatt tcacttccct tttggcagta actgaggtgg aatgtatata    1500
gaatgccggg cgtttcacaa tcaatggagc gtccctcaca cctcctacag tccctgtact    1560
actccagatc ctcagtggta ctcacaatgc acaggatctt ctcccagcag gaagcgtgat    1620
cgaacttgaa cagaataaag ttgtcgaaat cgttttgccc gctgcgggcg ccgttggcgg    1680
tcctcatcct tttcacttac atggtgtaag tatcagacgt cctcatgccc atattgctcc    1740
gaaccttaca cacctgattt cagcacaatt tctgggtggt tcgtagcgcc ggtcaaacca    1800
catacaattt caatgatgct cctatccgtg atgttgtcag tattggcggt gcaaacgatc    1860
aagtcacgat ccgatttgtg gtatgtatct cgtgccttgc attcattcca cgagtaatga    1920
tccttacact tcgggttctc agaccgataa ccctggccca tggttccttc actgtcacat    1980
tgactggcat ttggaggctg ggttcgctgt agtctttgcg gagggaatca atggtactgc    2040
agctgctaat ccagtcccag gtaagactct cgctgctttg cgtaatatct atgaatttaa    2100
atcatatcaa tttgcagcgg cttggaatca attgtgccca ttgtatgatg ccttgagccc    2160
aggtgataca tga                                                        2173
```

<210> SEQ ID NO 6
<211> LENGTH: 515
<212> TYPE: PRT
<213> ORGANISM: Cerrena unicolor

<400> SEQUENCE: 6

```
Met Ser Leu Leu Arg Ser Leu Thr Ser Leu Ile Val Leu Val Ile Gly
1               5                   10                  15

Ala Phe Ala Ala Ile Gly Pro Val Thr Asp Leu His Ile Val Asn Gln
            20                  25                  30

Asn Leu Asp Pro Asp Gly Phe Asn Arg Pro Thr Val Leu Ala Gly Gly
        35                  40                  45

Thr Phe Pro Gly Pro Leu Ile Arg Gly Asn Lys Gly Asp Asn Phe Lys
50                  55                  60

Ile Asn Val Ile Asp Asp Leu Thr Glu His Ser Met Leu Lys Ala Thr
65                  70                  75                  80

Ser Ile His Trp His Gly Phe Phe Gln Lys Gly Thr Asn Trp Ala Asp
                85                  90                  95

Gly Pro Ala Phe Val Thr Gln Cys Pro Ile Thr Ser Gly Asn Ala Phe
            100                 105                 110

Leu Tyr Asp Phe Asn Val Pro Asp Gln Ala Gly Thr Phe Trp Tyr His
        115                 120                 125

Ser His Leu Ser Thr Gln Tyr Cys Asp Gly Leu Arg Gly Ala Phe Val
130                 135                 140

Val Tyr Asp Pro Asn Asp Pro Asn Lys Gln Leu Tyr Asp Val Asp Asn
145                 150                 155                 160

Gly Asn Thr Val Ile Thr Leu Ala Asp Trp Tyr His Ala Leu Ala Gln
                165                 170                 175

Thr Val Thr Gly Val Ala Val Ser Asp Ala Thr Leu Ile Asn Gly Leu
            180                 185                 190

Gly Arg Ser Ala Thr Gly Pro Ala Asn Ala Pro Leu Ala Val Ile Ser
        195                 200                 205

Val Glu Arg Asn Lys Arg Tyr Arg Phe Arg Leu Val Ser Ile Ser Cys
210                 215                 220

Asp Pro Asn Phe Ile Phe Ser Ile Asp His His Pro Met Thr Val Ile
225                 230                 235                 240

Glu Met Asp Gly Val Asn Thr Gln Ser Met Thr Val Asp Ser Ile Gln
                245                 250                 255

Ile Phe Ala Gly Gln Arg Tyr Ser Phe Val Met Gln Ala Asn Gln Pro
            260                 265                 270

Val Gly Asn Tyr Trp Ile Arg Ala Lys Pro Asn Val Gly Asn Thr Thr
        275                 280                 285

Phe Leu Gly Gly Leu Asn Ser Ala Ile Leu Arg Tyr Val Gly Ala Pro
290                 295                 300

Asp Gln Glu Pro Thr Thr Asp Gln Thr Pro Asn Ser Thr Pro Leu Val
305                 310                 315                 320

Glu Ala Asn Leu Arg Pro Leu Val Tyr Thr Pro Val Pro Gly Gln Pro
                325                 330                 335

Phe Pro Gly Gly Ala Asp Ile Val Lys Asn Leu Ala Leu Gly Phe Asn
            340                 345                 350

Ala Gly Arg Phe Thr Ile Asn Gly Ala Ser Leu Thr Pro Pro Thr Val
        355                 360                 365

Pro Val Leu Leu Gln Ile Leu Ser Gly Thr His Asn Ala Gln Asp Leu
370                 375                 380
```

```
Leu Pro Ala Gly Ser Val Ile Glu Leu Glu Gln Asn Lys Val Val Glu
385                 390                 395                 400

Ile Val Leu Pro Ala Gly Ala Val Gly Gly Pro His Pro Phe His
            405                 410                 415

Leu His Gly His Asn Phe Trp Val Val Arg Ser Ala Gly Gln Thr Thr
        420                 425                 430

Tyr Asn Phe Asn Asp Ala Pro Ile Arg Asp Val Val Ser Ile Gly Gly
        435                 440                 445

Ala Asn Asp Gln Val Thr Ile Arg Phe Val Thr Asp Asn Pro Gly Pro
    450                 455                 460

Trp Phe Leu His Cys His Ile Asp Trp His Leu Glu Ala Gly Phe Ala
465                 470                 475                 480

Val Val Phe Ala Glu Gly Ile Asn Gly Thr Ala Ala Ala Asn Pro Val
            485                 490                 495

Pro Ala Ala Trp Asn Gln Leu Cys Pro Leu Tyr Asp Ala Leu Ser Pro
            500                 505                 510

Gly Asp Thr
        515

<210> SEQ ID NO 7
<211> LENGTH: 2663
<212> TYPE: DNA
<213> ORGANISM: Cerrena unicolor

<400> SEQUENCE: 7
caccgcgatg tctcttcttc gtagcttgac ctccctcatc gtactagcca ctggtgcatt      60
tgctgcaatc ggtccagtca ccgacctaca tatagtgaac cagaatctcg ccccagatgg     120
tttaaaccgc cccactgtac tcgcaggtgg tactttcccc ggtcctctga ttcgtggtaa     180
caaggtacgc ttcataaccg ccctccgtag acgtaggctt cggctgacat gaccatcatc     240
tgtagggaga taactttaaa attaatgtga ttgacgactt gacagaacac agtatgctca     300
aggctacgtc cattgtaagt ccctgattaa cgtttcacct ggtcatatcg ctcaacgtct     360
cgaagcactg gcatgggttc ttccagaagg gaaccaactg gccgatggc cccgcctttg     420 tcacccaatg tcctatcaca tcaggaaacg ccttcttgta tgatttcaac gttccggacc     480
aagctggtac tttctggtac cacagccatc tctcyacaca gtattgtgac ggtcttcgtg     540
gtgcctttgt cgtctatgat cctaatgatc ccaacaagca actctatgat gttgataacg     600
gcaagtccct tgcatatttc agttctatca tatcctcacc tgtattggca cagaaagcac     660
cgtgattacc ttggctgatt ggtatcatgc ccttgctcag actgtcactg gtgtcgcgtg     720
agtgacaaat ggcccttaat tgttcacata ttttcctgat tatcatatga tagagtatct     780
gatgcaacgt tgatcaacgg attgggacgt tcggccaccg gccccgcaaa tgcccctctg     840
gcggtcatca gtgtcgagcg gaataagagg tcagttccat aattatgatt atttcccgcg     900
ttacttccta acgattattt ttgtatccct ccacagatat cgtttccgat ggtttctat      960 ttcttgcgac cctaacttta ttttctcaat tgaccaccac ccaatgaccg taattgagat    1020
ggacggtgtt aatacccaat ctatgaccgt agattcgatc caaatattcg caggtcaacg    1080
atattcattt gtcgtaggtt attataaact gcccaccgat catctctcac gtaactgtta    1140
tagatgcaag ccaaccaacc agttggaaat tattggatcc gygctaaacc taatgttggg    1200
aacacaactt tccttggagg cctgaactcc gctatattac gatatgtggg agcccctgac    1260
caagaaccga ccactgacca aacacccaac tctacaccgc tcgtcgaggc gaacctacgt    1320
```

-continued

```
cccctcgtct atactcctgt ggtatgttgt tctcgttaca ataccaaac ctaatatgag    1380 gactgaacgg atctactagc cgggacagcc attccctggc ggtgctgata tcgtcaagaa    1440
cttagctttg ggtttcgtac gtgtatttca cttcccttttt ggcagtaact gaggtggaat    1500
gtatatagaa tgccgggcgt ttcacaatca atggaacatc cttcacacct cctacagtcc    1560
ctgtactact ccagatcctc agtggtactc acaatgcaca ggatcttctt ccagcaggaa    1620
gcgtgatcga acttgaacag ataaagttg tcgaaatcgt tctgcccgct gcgggcgccg    1680
ttggcggtcc tcatcctttc acttacatg gtgtaagtat cagacgtcct catgcctata    1740
ttgctccgaa ccttacacac ctgatttcag cacaatttct gggtggttcg tagcgccggt    1800
caaaccacat acaatttcaa tgatgctcct atccgtgatg ttgtcagtat tggcggtgca    1860
aacgatcaag tcacgatccg atttgtggta tgtatctcgt gccttgcatt cattccacga    1920
gtaatgatcc ttacacttcg ggttctcaga ccgataaccc tggcccatgg ttccttcact    1980
gtcacattga ctggcatttg gaggctgggt tcgctgtagt cttttgcggag ggaatcaatg    2040 gcactgcagc tgctaatcca gtcccaggta agactctcgc tgctttgcgt aatatctatg    2100
aatttaaagc atatcaattt gcagcggctt ggaatcaatt gtgcccgttg tatgatgcct    2160
tgagcccagg tgatacatga ttactcgtag ctgtgctttc ttatacatat tctatgggta    2220
tatcggagta gctgtactat agtatgtact atactaggtg ggatatgytg atgttgattt    2280
atataatttt gtttgaagag tgactttatc gacttgggat ttagccgagt acatactgat    2340
ctctcactac aggcttgttt tgtctttggg cgcttactca acagttgact gtttttgcta    2400
ttacgcattg aaccgcattc cggtcygact cgtgtcctct actgtgactt gtattggcat    2460
tctagcacat atgtctctta cctataggaa caatatgtct caacactgtt ccaaaacctg    2520
cgtaaaccaa atatcgtcca tcagatcaga tcattaacag tgccgcacta acctaataca    2580
ctggcargga ctgtggaaat ccctataaat gacctctaga ccgtgaggtc attgcaaggt    2640
cgctctcctt gtcaagatga ccc                                              2663
```

<210> SEQ ID NO 8
<211> LENGTH: 515
<212> TYPE: PRT
<213> ORGANISM: Cerrena unicolor

<400> SEQUENCE: 8

Met Ser Leu Leu Arg Ser Leu Thr Ser Leu Ile Val Leu Ala Thr Gly
1               5                   10                  15

Ala Phe Ala Ala Ile Gly Pro Val Thr Asp Leu His Ile Val Asn Gln
                20                  25                  30

Asn Leu Ala Pro Asp Gly Leu Asn Arg Pro Thr Val Leu Ala Gly Gly
            35                  40                  45

Thr Phe Pro Gly Pro Leu Ile Arg Gly Asn Lys Gly Asp Asn Phe Lys
        50                  55                  60

Ile Asn Val Ile Asp Asp Leu Thr Glu His Ser Met Leu Lys Ala Thr
65                  70                  75                  80

Ser Ile His Trp His Gly Phe Phe Gln Lys Gly Thr Asn Trp Ala Asp
                85                  90                  95

Gly Pro Ala Phe Val Thr Gln Cys Pro Ile Thr Ser Gly Asn Ala Phe
            100                 105                 110

Leu Tyr Asp Phe Asn Val Pro Asp Gln Ala Gly Thr Phe Trp Tyr His
        115                 120                 125

Ser His Leu Ser Thr Gln Tyr Cys Asp Gly Leu Arg Gly Ala Phe Val
130                 135                 140

Val Tyr Asp Pro Asn Asp Pro Asn Lys Gln Leu Tyr Asp Val Asp Asn
145                 150                 155                 160

Gly Asn Thr Val Ile Thr Leu Ala Asp Trp Tyr His Ala Leu Ala Gln
            165                 170                 175

Thr Val Thr Gly Val Ala Val Ser Asp Ala Thr Leu Ile Asn Gly Leu
            180                 185                 190

Gly Arg Ser Ala Thr Gly Pro Ala Asn Ala Pro Leu Ala Val Ile Ser
        195                 200                 205

Val Glu Arg Asn Lys Arg Tyr Arg Phe Arg Leu Val Ser Ile Ser Cys
210                 215                 220

Asp Pro Asn Phe Ile Phe Ser Ile Asp His His Pro Met Thr Val Ile
225                 230                 235                 240

Glu Met Asp Gly Val Asn Thr Gln Ser Met Thr Val Asp Ser Ile Gln
                245                 250                 255

Ile Phe Ala Gly Gln Arg Tyr Ser Phe Val Met Gln Ala Asn Gln Pro
            260                 265                 270

Val Gly Asn Tyr Trp Ile Arg Ala Lys Pro Asn Val Gly Asn Thr Thr
        275                 280                 285

Phe Leu Gly Gly Leu Asn Ser Ala Ile Leu Arg Tyr Val Gly Ala Pro
290                 295                 300

Asp Gln Glu Pro Thr Thr Asp Gln Thr Pro Asn Ser Thr Pro Leu Val
305                 310                 315                 320

Glu Ala Asn Leu Arg Pro Leu Val Tyr Thr Pro Val Pro Gly Gln Pro
                325                 330                 335

Phe Pro Gly Gly Ala Asp Ile Val Lys Asn Leu Ala Leu Gly Phe Asn
            340                 345                 350

Ala Gly Arg Phe Thr Ile Asn Gly Thr Ser Phe Thr Pro Pro Thr Val
        355                 360                 365

Pro Val Leu Leu Gln Ile Leu Ser Gly Thr His Asn Ala Gln Asp Leu
370                 375                 380

Leu Pro Ala Gly Ser Val Ile Glu Leu Glu Gln Asn Lys Val Val Glu
385                 390                 395                 400

Ile Val Leu Pro Ala Ala Gly Ala Val Gly Gly Pro His Pro Phe His
                405                 410                 415

Leu His Gly His Asn Phe Trp Val Val Arg Ser Ala Gly Gln Thr Thr
            420                 425                 430

Tyr Asn Phe Asn Asp Ala Pro Ile Arg Asp Val Val Ser Ile Gly Gly
        435                 440                 445

Ala Asn Asp Gln Val Thr Ile Arg Phe Val Thr Asp Asn Pro Gly Pro
450                 455                 460

Trp Phe Leu His Cys His Ile Asp Trp His Leu Glu Ala Gly Phe Ala
465                 470                 475                 480

Val Val Phe Ala Glu Gly Ile Asn Gly Thr Ala Ala Asn Pro Val
                485                 490                 495

Pro Ala Ala Trp Asn Gln Leu Cys Pro Leu Tyr Asp Ala Leu Ser Pro
            500                 505                 510

Gly Asp Thr
        515

<210> SEQ ID NO 9
<211> LENGTH: 1337
<212> TYPE: DNA

<213> ORGANISM: Cerrena unicolor

<400> SEQUENCE: 9

```
gtgggggcgg atccctaact gtttcgaatc ggcaccgaag tatgcaggtg tgacggagat    60
gaggcgtttt ttcatcttcc actgcagtat aaaatgtctc aggtaacgtc cagcttttttg   120
taccagagct acctccaaat acctttactc gcaaaggttt cgcgatgtct cttcttcgta   180
gcttgacctc cctcatcgta ctagccactg gtgcatttgc tgcaatcggt ccagtcactg   240
acctacatat agtgaaccag aatctcgccc agatggtttt caaccgcccc actgtactcg   300
caggtggtac tttccccggt cctctgattc gtggtaacaa ggtacgcttc ataaccgccc   360
tccgtagacg taggcttcgg ctgacatgac catcatctgt agggagataa ctttaaaatt   420
aatgtgattg acgacttgac agaacacagt atgctcaagg ccacgtccat tgtaagtccc   480
tgattaacgt ttcacctggt catatcgctc aacgtctcga agcactggca tgggttcttc   540
cagaagggaa ccaactgggc cgatggcccc gcctttgtca cccaatgtcc tatcacatca   600
ggaaactcct tcctgtatga tttcaacgtt ccggaccaag ctggtacttt ctggtaccac   660
agccatctct ctacacagta ttgtgacggt cttcgtggtg cctttgtcgt ctatgatcct   720
aatgatccca caagcaact ctatgatgtt gataacggca gtcccttgc atatttcatt   780
tctatcatat cctcacctgt attggcacag aaagcaccgt gattaccttg gctgattggt   840
atcatgccct gctcagact gtcactggtg tcgcgtgagt gacaaatggc cctcaattgt   900
tcacatattt tcctgattat catatgatag agtatctgat gcaacgttga tcaacggatt   960
gggacgttcg gccaccggcc ccgcaaatgc ccctctggcg gtcatcagtg tcgagcggaa  1020
taagaggtca gttccataat tatgattatt tcccgcgtta cttcctaaca attattcttg  1080
tatccctcca cagatatcgc ttccgattgg tgtctatttc ttgcgaccct aactttattt  1140
tctcaattga tcaccaccca atgaccgtaa ttgagatgga cggtgttaat acccaatcta  1200
tgaccgtaga ttcgatccaa atattcgcag gtcaacgata ttcatttgtc gtaggttatt  1260
ataaactgcc caccgatcat ctctcacgta actgttatag atgcaagcca accaaccrgt  1320
tggaaattat tggatcc                                                 1337
```

<210> SEQ ID NO 10
<211> LENGTH: 278
<212> TYPE: PRT
<213> ORGANISM: Cerrena unicolor

<400> SEQUENCE: 10

```
Met Ser Leu Leu Arg Ser Leu Thr Ser Leu Ile Val Leu Ala Thr Gly
1               5                   10                  15

Ala Phe Ala Ala Ile Gly Pro Val Thr Asp Leu His Ile Val Asn Gln
            20                  25                  30

Asn Leu Ala Pro Asp Gly Phe Asn Arg Pro Thr Val Leu Ala Gly Gly
        35                  40                  45

Thr Phe Pro Gly Pro Leu Ile Arg Gly Asn Lys Gly Asp Asn Phe Lys
    50                  55                  60

Ile Asn Val Ile Asp Asp Leu Thr Glu His Ser Met Leu Lys Ala Thr
65                  70                  75                  80

Ser Ile His Trp His Gly Phe Phe Gln Lys Gly Thr Asn Trp Ala Asp
                85                  90                  95

Gly Pro Ala Phe Val Thr Gln Cys Pro Ile Thr Ser Gly Asn Ser Phe
            100                 105                 110
```

Leu Tyr Asp Phe Asn Val Pro Asp Gln Ala Gly Thr Phe Trp Tyr His
                115                 120                 125

Ser His Leu Ser Thr Gln Tyr Cys Asp Gly Leu Arg Gly Ala Phe Val
        130                 135                 140

Val Tyr Asp Pro Asn Asp Pro Asn Lys Gln Leu Tyr Asp Val Asp Asn
145                 150                 155                 160

Gly Lys Thr Val Ile Thr Leu Ala Asp Trp Tyr His Ala Leu Ala Gln
                165                 170                 175

Thr Val Thr Gly Val Ala Val Ser Asp Ala Thr Leu Ile Asn Gly Leu
        180                 185                 190

Gly Arg Ser Ala Thr Gly Pro Ala Asn Ala Pro Leu Ala Val Ile Ser
                195                 200                 205

Val Glu Arg Asn Lys Arg Tyr Arg Phe Arg Leu Val Ser Ile Ser Cys
        210                 215                 220

Asp Pro Asn Phe Ile Phe Ser Ile Asp His His Pro Met Thr Val Ile
225                 230                 235                 240

Glu Met Asp Gly Val Asn Thr Gln Ser Met Thr Val Asp Ser Ile Gln
                245                 250                 255

Ile Phe Ala Gly Gln Arg Tyr Ser Phe Val Met Gln Ala Asn Gln Pro
        260                 265                 270

Val Gly Asn Tyr Trp Ile
        275

<210> SEQ ID NO 11
<211> LENGTH: 1080
<212> TYPE: DNA
<213> ORGANISM: Cerrena unicolor

<400> SEQUENCE: 11
tgcaatcgga ccggtbgctg accttcacat tacggacgat accattgccc ccgatggttt      60
ctctcgtcct gctgttctcg ctggcggggg tttccctggc cctctcatca ccggaaacaa     120
ggtaatgcct aatggttgcg tctttgttgg tgctctcatt catccacgac attttgtacc     180
agggcgacgc ctttaaactc aatgtcatcg atgaactaac ggacgcatcc atgctgaagy     240
cgacttccat cgtaagtctc gctgtattgc tccttgagcc atttcattga ctataactac     300
aaccagcact ggcatggatt cttccaaaag ggtactaatt gggcagatgg tcccgctttt     360
gtgaaccaat gccccatcac cacgggaaac tccttcttgt acgacttcca ggttcctgat     420
caagctggta agcatgagat tacactagga aagtttaatt taataactat tcaatcagga     480
acctactggt atcatagtca tttgtctacg caatactgtg atggtctcag aggtgcattc     540
gttgtctacg acccttcaga tcctcacaag atctctacg acgtcgacga cggtgagctt     600
tgcttttttc attggtatcc attatcgctc acgtgtcatt actgcgccac agaaagtacc     660
gtcatcactt ggctgattg gtatcatact ttggctcgtc agattgttgg cgttgcgtga     720
gtagtcttgt accgactgaa acatattcca gttgctgact cccccacagc atttctgata     780
ctaccttgat aaacggtttg gccgcaata ccaatggtcc ggctgatgct gctcttgctg     840
tgatcaatgt tgacgctggc aaacggtgtg tccagattac tatactcccc atgacgtctc     900
aatgctgatg tgtactactt ccaggtaccg tttccgtctt gtttccatat cctgtgaccc     960
caattgggta ttctcgattg acaaccatga ctttacggtc attgaagtcg atggtgttaa    1020
cagtcaacct ctcaacgtcg attctgttca gatcttcgcc ggacaacgtt actcgttcgt    1080

<210> SEQ ID NO 12

```
<211> LENGTH: 246
<212> TYPE: PRT
<213> ORGANISM: Cerrena unicolor
<220> FEATURE:
<221> NAME/KEY: misc_feature
<222> LOCATION: (60)..(60)
<223> OTHER INFORMATION: Xaa can be any naturally occurring amino acid

<400> SEQUENCE: 12
```

Ala Ile Gly Pro Val Ala Asp Leu His Ile Thr Asp Thr Ile Ala
1               5                   10                  15

Pro Asp Gly Phe Ser Arg Pro Ala Val Leu Ala Gly Gly Phe Pro
                20                  25                  30

Gly Pro Leu Ile Thr Gly Asn Lys Gly Asp Ala Phe Lys Leu Asn Val
            35                  40                  45

Ile Asp Glu Leu Thr Asp Ala Ser Met Leu Lys Xaa Thr Ser Ile His
    50                  55                  60

Trp His Gly Phe Phe Gln Lys Gly Thr Asn Trp Ala Asp Gly Pro Ala
65              70                  75                  80

Phe Val Asn Gln Cys Pro Ile Thr Thr Gly Asn Ser Phe Leu Tyr Asp
                85                  90                  95

Phe Gln Val Pro Asp Gln Ala Gly Thr Tyr Trp Tyr His Ser His Leu
                100                 105                 110

Ser Thr Gln Tyr Cys Asp Gly Leu Arg Gly Ala Phe Val Val Tyr Asp
                115                 120                 125

Pro Ser Asp Pro His Lys Asp Leu Tyr Asp Val Asp Glu Ser Thr
                130                 135                 140

Val Ile Thr Leu Ala Asp Trp Tyr His Thr Leu Ala Arg Gln Ile Val
145                 150                 155                 160

Gly Val Ala Ile Ser Asp Thr Thr Leu Ile Asn Gly Leu Gly Arg Asn
                165                 170                 175

Thr Asn Gly Pro Ala Asp Ala Ala Leu Ala Val Ile Asn Val Asp Ala
                180                 185                 190

Gly Lys Arg Tyr Arg Phe Arg Leu Val Ser Ile Ser Cys Asp Pro Asn
                195                 200                 205

Trp Val Phe Ser Ile Asp Asn His Asp Phe Thr Val Ile Glu Val Asp
                210                 215                 220

Gly Val Asn Ser Gln Pro Leu Asn Val Asp Ser Val Gln Ile Phe Ala
225                 230                 235                 240

Gly Gln Arg Tyr Ser Phe
                245

```
<210> SEQ ID NO 13
<211> LENGTH: 2809
<212> TYPE: DNA
<213> ORGANISM: Cerrena unicolor

<400> SEQUENCE: 13
```
gattctaata gaccaggcat accaagagat ctacaggttg acagaccatt cttctaggcg      60
gcatttatgc tgtagcgtca gaaattatct ctccatttgt atcccacagg tcctgtaata     120
acacggagac agtccaaact gggatgcctt ttttctcaac tatgggcgca catagtctgg     180
acgatggtat ataagacgat ggtatgagac ccatgaagtc agaacacttt tgctctctga     240
catttcatgg ttcacactct cgagatggga ttgaactcgg ctattacatc gcttgctatc     300
ttagctctgt cagtcggaag ctatgctgca attgggcccg tggccgacat acacattgtc     360
aacaaagacc ttgctccaga tggcgtacaa cgtccaaccg tgcttgccgg aggcactttt     420

```
cctgggacgt tgatcaccgg tcagaaagta agggatatta gtttgcgtca aagagccaac    480
caaaactaac cgtcccgtac tatagggtga caacttccag ctcaatgtca tcgatgatct    540
taccgacgat cggatgttga cgccaacttc cattgtgagc ctattattgt atgatttatc    600
cgaatagttt cgcagtctga tcattggatc tctatcgcta gcattggcac ggtttcttcc    660
agaagggaac cgcttgggcc gacggtcccg ccttcgtaac tcagtgccct ataatagcag    720 ataactctt tctgtatgac ttcgacgtcc cagaccaagc tggtactttc tggtatcata    780
gtcatctatc cactcagtac tgtgacggtt tacgtggtgc cttcgttgtg tacgatccta    840
acgatcctca caaagaccta tacgatgttg atgacggtgg gttccaaata tttgttctgc    900
agacattgta ttgacggtgt tcattataat ttcagagagc accgtgatta cccttgcgga    960
ttggtaccat gttctcgccc agaccgttgt cggcgctgcg tgagtaacac atacacgcgc   1020
tccggcacac tgatactaat tttttttat tgtagcactc ctgattctac cttgatcaac   1080
gggttaggcc gttcacagac cggacccgct gatgctgagc tggctgttat cagcgttgaa   1140
cataacaaac ggtatgtcat ctctacccag tatcttctct cctgctctaa ttcgctgttt   1200
caccatagat accgtttccg tttggtttcg atttcgtgcg accccaactt taccttctcc   1260
gttgatggtc ataatatgac tgtcatcgaa gtcgatggtg tcaacacacg accctgacc   1320 gttgactcta ttcaaatctt cgccggacag aggtattcct ttgtcgtaag ttaatcgata   1380
tattctcctt attaccctg tgtaattgat gtcaatagct caatgctaac caacccgaag   1440
acaattactg gatccgtgct atgccaaaca tcggtagaaa tacaacaaca ctggacggaa   1500
agaatgccgc tatccttcga tacaagaatg cttctgtaga agagcccaag accgttgggg   1560
gccccgctca atccccgttg aatgaagcgg acctgcgtcc actcgtacct gctcctgtgg   1620
tatgtcttgt cgcgctgttc catcgctatt tcatattaac gttttgtttt tgtcaagcct   1680
ggaaacgctg ttccaggtgg cgcagacatc aatcacaggc ttaacttaac tttcgtacgt   1740
acacctggtt gaaacattat atttccagtc taacctctct tgtagagtaa cggcctcttc   1800
agcatcaaca cgcctccttt cactaatcct tcggtccccg ccttattaca aattctgagc   1860
ggtgctcaga acgctcaaga tttacttcca acgggtagtt acattggcct tgaactaggc   1920
aaggttgtgg agctcgttat acctcctctg gcagttggag accgcaccc tttccatctt   1980 catggcgtaa gcataccaca ctcccgcagc cagaatgacg caaactaatc atgatatgca   2040
gcacaatttc tgggtcgtcc gtagtgcagg tagcgatgag tataactttg acgatgctat   2100
cctcagggac gtcgtragca ttggagcggg gactgatgaa gtcacaatcc gtttcgtggt   2160
atgtctcacc cctcgcattt tgagacgcaa gagctgatat attttaacat agaccgacaa   2220
tccgggcccg tggttcctcc attgccatat tgattggcat ttggaggcag gccttgccat   2280
cgtcttcgct gagggcatca atcagaccgc tgcagccaac ccaacacccc gtacgtgaca   2340
ctgagggttt ctttatagtg ctggattact gaatcgagat ttctccacag aagcatggga   2400
tgagctttgc cccaaatata acgggttgag tgcgagccag aaggtcaagc ctaagaaagg   2460
aactgctatt taaacgtggt cctagactac gggcatataa gtattcgggt agcgcgtgtg   2520
agcaatgttc cgatacacgt agattcatca ccggacacgt gggacaatt tgtgtataat   2580 ggctagtaac gtatctgagt tctggtgtgt agttcaaaga dacagccctt cctgagacag   2640
cccttcctga dacagccctt cctgagacgt gacctccgta gtctgcacac gatactycta   2700
aatacgtatg gcaagatgac aaagaggagg atgtgagtta ctacgaacag aaatagtgcc   2760
```

```
cggcctcgga gagatgttct tgaatatggg actgggacca acatccgga           2809
```

<210> SEQ ID NO 14
<211> LENGTH: 526
<212> TYPE: PRT
<213> ORGANISM: Cerrena unicolor

<400> SEQUENCE: 14

Met Gly Leu Asn Ser Ala Ile Thr Ser Leu Ala Ile Leu Ala Leu Ser
1               5                   10                  15

Val Gly Ser Tyr Ala Ala Ile Gly Pro Val Ala Asp Ile His Ile Val
            20                  25                  30

Asn Lys Asp Leu Ala Pro Asp Gly Val Gln Arg Pro Thr Val Leu Ala
        35                  40                  45

Gly Gly Thr Phe Pro Gly Thr Leu Ile Thr Gly Gln Lys Gly Asp Asn
    50                  55                  60

Phe Gln Leu Asn Val Ile Asp Asp Leu Thr Asp Arg Met Leu Thr
65                  70                  75                  80

Pro Thr Ser Ile His Trp His Gly Phe Phe Gln Lys Gly Thr Ala Trp
                85                  90                  95

Ala Asp Gly Pro Ala Phe Val Thr Gln Cys Pro Ile Ile Ala Asp Asn
            100                 105                 110

Ser Phe Leu Tyr Asp Phe Asp Val Pro Asp Gln Ala Gly Thr Phe Trp
        115                 120                 125

Tyr His Ser His Leu Ser Thr Gln Tyr Cys Asp Gly Leu Arg Gly Ala
    130                 135                 140

Phe Val Val Tyr Asp Pro Asn Asp Pro His Lys Asp Leu Tyr Asp Val
145                 150                 155                 160

Asp Asp Gly Gly Thr Val Ile Thr Leu Ala Asp Trp Tyr His Val Leu
                165                 170                 175

Ala Gln Thr Val Val Gly Ala Ala Thr Pro Asp Ser Thr Leu Ile Asn
            180                 185                 190

Gly Leu Gly Arg Ser Gln Thr Gly Pro Ala Asp Ala Glu Leu Ala Val
        195                 200                 205

Ile Ser Val Glu His Asn Lys Arg Tyr Arg Phe Arg Leu Val Ser Ile
    210                 215                 220

Ser Cys Asp Pro Asn Phe Thr Phe Ser Val Asp Gly His Asn Met Thr
225                 230                 235                 240

Val Ile Glu Val Asp Gly Val Asn Thr Arg Pro Leu Thr Val Asp Ser
                245                 250                 255

Ile Gln Ile Phe Ala Gly Gln Arg Tyr Ser Phe Val Leu Asn Ala Asn
            260                 265                 270

Gln Pro Glu Asp Asn Tyr Trp Ile Arg Ala Met Pro Asn Ile Gly Arg
        275                 280                 285

Asn Thr Thr Thr Leu Asp Gly Lys Asn Ala Ala Ile Leu Arg Tyr Lys
    290                 295                 300

Asn Ala Ser Val Glu Glu Pro Lys Thr Val Gly Gly Pro Ala Gln Ser
305                 310                 315                 320

Pro Leu Asn Glu Ala Asp Leu Arg Pro Leu Val Pro Ala Pro Val Pro
                325                 330                 335

Gly Asn Ala Val Pro Gly Gly Ala Asp Ile Asn His Arg Leu Asn Leu
            340                 345                 350

Thr Phe Ser Asn Gly Leu Phe Ser Ile Asn Asn Ala Ser Phe Thr Asn
        355                 360                 365

```
Pro Ser Val Pro Ala Leu Leu Gln Ile Leu Ser Gly Ala Gln Asn Ala
    370                 375                 380

Gln Asp Leu Leu Pro Thr Gly Ser Tyr Ile Gly Leu Glu Leu Gly Lys
385                 390                 395                 400

Val Val Glu Leu Val Ile Pro Pro Leu Ala Val Gly Gly Pro His Pro
                405                 410                 415

Phe His Leu His Gly His Asn Phe Trp Val Val Arg Ser Ala Gly Ser
            420                 425                 430

Asp Glu Tyr Asn Phe Asp Asp Ala Ile Leu Arg Asp Val Val Ser Ile
            435                 440                 445

Gly Ala Gly Thr Asp Glu Val Thr Ile Arg Phe Val Thr Asp Asn Pro
450                 455                 460

Gly Pro Trp Phe Leu His Cys His Ile Asp Trp His Leu Glu Ala Gly
465                 470                 475                 480

Leu Ala Ile Val Phe Ala Glu Gly Ile Asn Gln Thr Ala Ala Ala Asn
                485                 490                 495

Pro Thr Pro Gln Ala Trp Asp Glu Leu Cys Pro Lys Tyr Asn Gly Leu
            500                 505                 510

Ser Ala Ser Gln Lys Val Lys Pro Lys Lys Gly Thr Ala Ile
            515                 520                 525

<210> SEQ ID NO 15
<211> LENGTH: 2299
<212> TYPE: DNA
<213> ORGANISM: Cerrena unicolor

<400> SEQUENCE: 15
gatctggacg atggtatata agacgatggt atgagaccca tgaagtctga acacttttgc      60
tctctgacat ttcatggttc atactctcga gatgggattg aactcggcta ttacatcgct     120
tgctatctta gctctgtcag tcggaagcta tgctgcaatt gggcccgtgg ccgacataca     180
cattgtcaac aaagaccttg ctccagatgg tgtacaacgt ccaaccgtgc tcgccggagg     240
cacttttcct gggacgttga tcaccggtca gaaagtaagg aatattagtt tgcgtcaaag     300
agccaaccaa aattaaccgt cccgtcccat agggtgacaa cttccagctc aatgtcattg     360
atgatcttac cgacgatcgg atgttgacac caacttccat tgtgagccta ttattgtatg     420
atttatccgt atagtttctc agtctgatca ttggctctct atcgctagca ttggcacggt     480
ttcttccaga agggaaccgc ttgggccgac ggtcccgcct tcgtaactca gtgccctata     540
atagcagata actctttttct gtatgacttc gacgtccccg accaagctgg tactttctgg     600
tatcatagtc atctatccac tcagtactgt gacggtttac gtggtgcctt cgttgtgtac     660
gatcctaacg atcctcacaa agacctatac gatgttgatg acggtgggtt ccaaatactt     720
gaccaagaaa cattatattg atagtatcca ctctgatttt cagagagcac cgtgattacc     780
cttgcggatt ggtaccatgt tctcgcccag accgttgtcg cgctgcgtg agtaacacat     840 acacgcgctc cggcacactg atactaattt tttattgtag cactcctgat tctaccttga     900
tcaacgggtt aggccgttca cagaccggac ccgctgatgc tgagctggct gttatcagcg     960
ttgaacataa caaacggtat gtcatctcta cccattatct tctctcctgc tttaattcgc    1020
tgtttcacca tagataccga ttccgtttgg tttcgatttc gtgcgacccc aactttacct    1080
tctccgttga tggtcataat atgactgtca tcgaagtcga cggtgtcaac acacgacccc    1140
tgaccgttga ctctattcaa atcttcgccg gacagaggta ttcctttgtc gtaagttaat    1200
cgatatattc tccctattac ccctgtgtaa ttgatgtcaa cagctcaatg ctaaccaacc    1260
```

```
cgacgacaat tactggatcc gtgctatgcc aaacatcggt agaaatacaa caacactgga    1320
cggaaagaat gccgctatcc ttcgatacaa gaatgcttct gtagaagagc ccaagaccgt    1380
tgggggcccc gctcaatccc cgttgaatga agcggacctg cgtccactcg tacctgctcc    1440
tgtggtatgt cttgtcgtgc tgttccatcg ctatttcata ttaacgtttt gttttgtca     1500 agcctggaaa cgctgttcca ggtggcgcag acatcaatca caggcttaac ttaactttcg    1560
tacgtacacc tggttgaaac attatatttc cagtctaacc tcttgtagag taacggcctt    1620
ttcagcatca acaacgcctc cttcactaat ccttcggtcc ccgccttatt acaaattctg    1680
agcggtgctc agaacgctca agatttactt ccaacgggta gttacattgg ccttgaacta    1740
ggcaaggttg tggagctcgt tatacctcct ctggcagttg aggaccgca cccttccat     1800 cttcatggcg taagcatacc acactcccgc agccagaatg acgcaaacta atcatgatat    1860
gcagcacaat ttctgggtcg tccgtagtgc aggtagcgat gagtataact ttgacgatgc    1920
tatcctcagg gacgtcgtga gcattggagc ggggactgat gaagtcacaa tccgtttcgt    1980
ggtatgtctc accectcgca ttttgagacg caagagctga tatatttaa catagaccga     2040 caatccgggc ccgtggttcc tccattgcca tattgattgg catttggagg caggccttgc    2100
catcgtcttc gctgagggca tcaatcagac cgctgcagcc aacccaacac cccgtacgtg    2160
acactgaggg tttctttata gtgctggatt actgaatcga gatttctcca cagaagcatg    2220
ggatgagctt tgccccaaat ataacggggtt gagtgcgagc cagaaggtca agcctaagaa    2280
aggaactgct atttaaacg                                                 2299
```

<210> SEQ ID NO 16
<211> LENGTH: 526
<212> TYPE: PRT
<213> ORGANISM: Cerrena unicolor

<400> SEQUENCE: 16

```
Met Gly Leu Asn Ser Ala Ile Thr Ser Leu Ala Ile Leu Ala Leu Ser
1               5                   10                  15

Val Gly Ser Tyr Ala Ala Ile Gly Pro Val Ala Asp Ile His Ile Val
            20                  25                  30

Asn Lys Asp Leu Ala Pro Asp Gly Val Gln Arg Pro Thr Val Leu Ala
        35                  40                  45

Gly Gly Thr Phe Pro Gly Thr Leu Ile Thr Gly Gln Lys Gly Asp Asn
    50                  55                  60

Phe Gln Leu Asn Val Ile Asp Asp Leu Thr Asp Arg Met Leu Thr
65                  70                  75                  80

Pro Thr Ser Ile His Trp His Gly Phe Phe Gln Lys Gly Thr Ala Trp
                85                  90                  95

Ala Asp Gly Pro Ala Phe Val Thr Gln Cys Pro Ile Ile Ala Asp Asn
            100                 105                 110

Ser Phe Leu Tyr Asp Phe Asp Val Pro Asp Gln Ala Gly Thr Phe Trp
        115                 120                 125

Tyr His Ser His Leu Ser Thr Gln Tyr Cys Asp Gly Leu Arg Gly Ala
    130                 135                 140

Phe Val Val Tyr Asp Pro Asn Asp Pro His Lys Asp Leu Tyr Asp Val
145                 150                 155                 160

Asp Asp Gly Gly Thr Val Ile Thr Leu Ala Asp Trp Tyr His Val Leu
                165                 170                 175

Ala Gln Thr Val Val Gly Ala Ala Thr Pro Asp Ser Thr Leu Ile Asn
```

```
            180                 185                 190
Gly Leu Gly Arg Ser Gln Thr Gly Pro Ala Asp Ala Glu Leu Ala Val
            195                 200                 205

Ile Ser Val Glu His Asn Lys Arg Tyr Arg Phe Arg Leu Val Ser Ile
            210                 215                 220

Ser Cys Asp Pro Asn Phe Thr Phe Ser Val Asp Gly His Asn Met Thr
225                 230                 235                 240

Val Ile Glu Val Asp Gly Val Asn Thr Arg Pro Leu Thr Val Asp Ser
                245                 250                 255

Ile Gln Ile Phe Ala Gly Gln Arg Tyr Ser Phe Val Leu Asn Ala Asn
            260                 265                 270

Gln Pro Asp Asp Asn Tyr Trp Ile Arg Ala Met Pro Asn Ile Gly Arg
            275                 280                 285

Asn Thr Thr Thr Leu Asp Gly Lys Asn Ala Ala Ile Leu Arg Tyr Lys
            290                 295                 300

Asn Ala Ser Val Glu Glu Pro Lys Thr Val Gly Gly Pro Ala Gln Ser
305                 310                 315                 320

Pro Leu Asn Glu Ala Asp Leu Arg Pro Leu Val Pro Ala Pro Val Pro
                325                 330                 335

Gly Asn Ala Val Pro Gly Gly Ala Asp Ile Asn His Arg Leu Asn Leu
            340                 345                 350

Thr Phe Ser Asn Gly Leu Phe Ser Ile Asn Ala Ser Phe Thr Asn
            355                 360                 365

Pro Ser Val Pro Ala Leu Leu Gln Ile Leu Ser Gly Ala Gln Asn Ala
            370                 375                 380

Gln Asp Leu Leu Pro Thr Gly Ser Tyr Ile Gly Leu Glu Leu Gly Lys
385                 390                 395                 400

Val Val Glu Leu Val Ile Pro Pro Leu Ala Val Gly Gly Pro His Pro
                405                 410                 415

Phe His Leu His Gly His Asn Phe Trp Val Val Arg Ser Ala Gly Ser
            420                 425                 430

Asp Glu Tyr Asn Phe Asp Asp Ala Ile Leu Arg Asp Val Val Ser Ile
            435                 440                 445

Gly Ala Gly Thr Asp Glu Val Thr Ile Arg Phe Val Thr Asp Asn Pro
            450                 455                 460

Gly Pro Trp Phe Leu His Cys His Ile Asp Trp His Leu Glu Ala Gly
465                 470                 475                 480

Leu Ala Ile Val Phe Ala Glu Gly Ile Asn Gln Thr Ala Ala Ala Asn
                485                 490                 495

Pro Thr Pro Gln Ala Trp Asp Glu Leu Cys Pro Lys Tyr Asn Gly Leu
            500                 505                 510

Ser Ala Ser Gln Lys Val Lys Pro Lys Lys Gly Thr Ala Ile
            515                 520                 525

<210> SEQ ID NO 17
<211> LENGTH: 1163
<212> TYPE: DNA
<213> ORGANISM: Cerrena unicolor

<400> SEQUENCE: 17
tgcaatcgga ccggtggccg acctcaagat cgtaaaccga dacattgcac ctgacggttt     60
tattcgtccc gccgttctcg ctggagggtc gttccctggt cctctcatta cagggcagaa    120
agtacgttac gctatctcgg tgctttggct taattaaact atttgacttt gtgttctctt    180
```

```
agggaacga gttcaaaatc aatgtagtca atcaactgac cgatggttct atgttaaaat    240
ccacctcaat cgtaagcaga atgagccctt tgcatctcgt tttattgtta atgcgcccac    300
tatagcattg gcatggattc ttccagaagg gaacaaactg gcagacggtt cctgcgttcg    360
tgaaccaatg tccaatcgcc acgaacaatt cgttcttgta tcagtttacc tcacaggaac    420
agccaggtga gtatgagatg gagttcatcc gagcatgaac tgatttattt ggaacctagg    480
cacattttgg taccatagtc atctttccac acaatactgc gatggtttgc gagggccact    540
cgtggtgtat gacccacaag acccgcatgc tgttctctac gacgtcgacg atggttcgta    600
cttcgcatat ccacgctcgc tttcatacaa tgtaaacttt gttcctccag aaagtacaat    660
catcacgctc gcggattggt atcataccct tggctcggcaa gtgaaaggcc cagcgtaagg    720
cactttagtg tttcctcata gtccaagaaa ttctaacacg ccttcttcat cagggttcct    780
ggtacgacct tgatcaacgg gttggggcgt cacaacaatg gtcctctaga tgctgaacta    840
gcggtgatca gtgttcaagc cggcaaacgg caagttcaat tcacactttt cactctgtac    900
cttcttcctg acattctttt cttgtagtta ccgcttccgc ctgatttcaa tttcatgcga    960
tcccaactac gtattctcca ttgatggcca tgatatgact gtcatcgaag tggatagtgt   1020
taacagtcaa cctctcaagg tagattctat ccaaatattt gcaggtcaga gatattcgtt   1080
cgtggtgagt cagatcaggg catatccttt tgtcgatacg tcattgacca tataatgcta   1140
caagctgaat gccaaccaac cag                                           1163

<210> SEQ ID NO 18
<211> LENGTH: 262
<212> TYPE: PRT
<213> ORGANISM: Cerrena unicolor

<400> SEQUENCE: 18

Ala Ile Gly Pro Val Ala Asp Leu Lys Ile Val Asn Arg Asp Ile Ala
1               5                   10                  15

Pro Asp Gly Phe Ile Arg Pro Ala Val Leu Ala Gly Gly Ser Phe Pro
            20                  25                  30

Gly Pro Leu Ile Thr Gly Gln Lys Gly Asn Glu Phe Lys Ile Asn Val
        35                  40                  45

Val Asn Gln Leu Thr Asp Gly Ser Met Leu Lys Ser Thr Ser Ile His
    50                  55                  60

Trp His Gly Phe Phe Gln Lys Gly Thr Asn Trp Ala Asp Gly Pro Ala
65                  70                  75                  80

Phe Val Asn Gln Cys Pro Ile Ala Thr Asn Asn Ser Phe Leu Tyr Gln
                85                  90                  95

Phe Thr Ser Gln Glu Gln Pro Gly Thr Phe Trp Tyr His Ser His Leu
            100                 105                 110

Ser Thr Gln Tyr Cys Asp Gly Leu Arg Gly Pro Leu Val Val Tyr Asp
        115                 120                 125

Pro Gln Asp Pro His Ala Val Leu Tyr Asp Val Asp Asp Glu Ser Thr
    130                 135                 140

Ile Ile Thr Leu Ala Asp Trp Tyr His Thr Leu Ala Arg Gln Val Lys
145                 150                 155                 160

Gly Pro Ala Val Pro Gly Thr Thr Leu Ile Asn Gly Leu Gly Arg His
                165                 170                 175

Asn Asn Gly Pro Leu Asp Ala Glu Leu Ala Val Ile Ser Val Gln Ala
            180                 185                 190

Gly Lys Arg Gln Val Gln Phe Thr Leu Phe Thr Leu Tyr Arg Phe Arg
```

```
              195                 200                 205
Leu Ile Ser Ile Ser Cys Asp Pro Asn Tyr Val Phe Ser Ile Asp Gly
    210                 215                 220

His Asp Met Thr Val Ile Glu Val Asp Ser Val Asn Ser Gln Pro Leu
225                 230                 235                 240

Lys Val Asp Ser Ile Gln Ile Phe Ala Gly Gln Arg Tyr Ser Phe Val
                245                 250                 255

Leu Asn Ala Asn Gln Pro
            260

<210> SEQ ID NO 19
<211> LENGTH: 10
<212> TYPE: PRT
<213> ORGANISM: Cerrena unicolor

<400> SEQUENCE: 19

Ala Ile Gly Pro Val Ala Asp Leu His Ile
1               5                   10

<210> SEQ ID NO 20
<211> LENGTH: 7
<212> TYPE: PRT
<213> ORGANISM: Cerrena unicolor

<400> SEQUENCE: 20

Met Leu Thr Pro Thr Ser Ile
1               5

<210> SEQ ID NO 21
<211> LENGTH: 6
<212> TYPE: PRT
<213> ORGANISM: Cerrena unicolor

<400> SEQUENCE: 21

Thr Val Gly Gly Pro Ala
1               5

<210> SEQ ID NO 22
<211> LENGTH: 10
<212> TYPE: PRT
<213> ORGANISM: Cerrena unicolor

<400> SEQUENCE: 22

Tyr Ser Phe Val Leu Asn Ala Asn Gln Pro
1               5                   10

<210> SEQ ID NO 23
<211> LENGTH: 20
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 23
gcaatcggac cngtngcaga                                        20
```

```
<210> SEQ ID NO 24
<211> LENGTH: 20
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 24
gcaatcggac cngtngctga                                          20

<210> SEQ ID NO 25
<211> LENGTH: 20
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 25
gcaatcggac cngtngcgga                                          20

<210> SEQ ID NO 26
<211> LENGTH: 20
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 26
gcaatcggac cngtngccga                                          20

<210> SEQ ID NO 27
<211> LENGTH: 20
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 27
ggttgatttg cattnagnac                                          20
```

```
<210> SEQ ID NO 28
<211> LENGTH: 20
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 28
ggttgatttg cgttnagnac                                        20

<210> SEQ ID NO 29
<211> LENGTH: 20
<212> TYPE: DNA
<213> ORGANISM: Artificial
<220> FEATURE:
<223> OTHER INFORMATION: synthetic primer

<400> SEQUENCE: 29
ggacgtggcc ttgagcatac                                        20

<210> SEQ ID NO 30
<211> LENGTH: 20
<212> TYPE: DNA
<213> ORGANISM: Artificial
<220> FEATURE:
<223> OTHER INFORMATION: synthetic primer

<400> SEQUENCE: 30
tctgtcaagt cgtcaatcac                                        20

<210> SEQ ID NO 31
<211> LENGTH: 16
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (1)..(10)
<223> OTHER INFORMATION: n is a, c, g, or t

<400> SEQUENCE: 31
nnnnnnnnnn ggatcc                                            16

<210> SEQ ID NO 32
<211> LENGTH: 20
<212> TYPE: DNA
<213> ORGANISM: Artificial
<220> FEATURE:
<223> OTHER INFORMATION: synthetic primer

<400> SEQUENCE: 32
ttaccacgaa tcagaggacc                                        20

<210> SEQ ID NO 33
<211> LENGTH: 20
<212> TYPE: DNA
<213> ORGANISM: Artificial
<220> FEATURE:
<223> OTHER INFORMATION: synthetic primer
```

<400> SEQUENCE: 33
cctcacctgt attggcacag                                                    20

<210> SEQ ID NO 34
<211> LENGTH: 20
<212> TYPE: DNA
<213> ORGANISM: Artificial
<220> FEATURE:
<223> OTHER INFORMATION: synthetic primer

<400> SEQUENCE: 34
ttggtatcat gcccttgctc                                                    20

<210> SEQ ID NO 35
<211> LENGTH: 20
<212> TYPE: DNA
<213> ORGANISM: Artificial
<220> FEATURE:
<223> OTHER INFORMATION: synthetic primer

<400> SEQUENCE: 35
ttcgcaggtc aacgatattc                                                    20

<210> SEQ ID NO 36
<211> LENGTH: 20
<212> TYPE: DNA
<213> ORGANISM: Artificial
<220> FEATURE:
<223> OTHER INFORMATION: synthetic primer

<400> SEQUENCE: 36
gttaggtggt tgaaggattg                                                    20

<210> SEQ ID NO 37
<211> LENGTH: 1316
<212> TYPE: DNA
<213> ORGANISM: Cerrena unicolor

<400> SEQUENCE: 37
ttcgcaggtc aacgatattc gttcgtcgta agtctctttg aacgattact gcttctttgt        60
ccattctctg acctgtttaa acagctccat gccaaccgtc ctgaaaacaa ctattggatc       120
agggccaaac ctaatatcgg tacggatact accacagaca acggcatgaa ctctgccatt       180
ctgcgataca acggcgcacc tgttgcggaa ccgcaaactg ttcaatctcc cagtctcacc       240
cctttgctcg aacagaacct tcgccctctc gtgtacactc tgtggtatg tttcaaagcg        300 ttgtaatttg attgtggtca ttctaacgtt actgcgtttg catagcctgg aaatcctacg       360
cctggcggcg ccgatattgt ccatattctt gacttgagtt ttgtgcggag tcaacattcg       420
taaagatgag agtgtttcta atttcttcaa taataggatg ctggtcgctt cagtatcaac       480
ggtgcctcgt tccttgatcc taccgtcccc gttctcctgc aaattctcag cggcacgcag       540
aatgcacaag atctactccc tcctggaagt gtgattcctc tcgaattagg caaggtcgtc       600
gaattagtca tacctgcagg tgtcgtcggt ggacctcatc cgttccatct ccatgggta        660 cgtaacccga acttataaca gtcttggact tacccgctga caagtgtata gcataacttc       720
tgggtcgtgc gaagtgccgg aaccgaccag tacaacttta acgatgccat tctccgagac       780
gtcgtcagta taggaggaac cggggatcaa gtcaccattc gtttcgtggt atgtttcatt       840
cttgtggatg tatgtgctct aggatactaa ccggcttacg cgtatagacc gataaccccg       900

```
gaccgtggtt cctccattgc catatcgact ggcacttgga agcgggtctc gctatcgtat    960
ttgcagaggg aattgaaaat actgctgcgt ctaatccaac ccccgtacg tggtttccct   1020 cacatcgtgg atctaagcag cttactaaca tacatttgca gaggcttggg atgagctttg   1080
cccgaagtat aacgcgctca gcgcacaaaa gaaggttgca tctaagaaag gcactgccat   1140
ctaatttttg taacaaacaa ggagggtctc ttgtactttt attgggattt atttcttggg   1200
gtttgttgtt caacttgatt ctactatgtt tggaagtagc gatgacgaaa ggggctcgcg   1260
catttatata ctatctctct tggcatcacc tgcagctcaa tccttcaacc acctaa      1316
```

<210> SEQ ID NO 38
<211> LENGTH: 16
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (1)..(10)
<223> OTHER INFORMATION: n is a, c, g, or t

<400> SEQUENCE: 38
nnnnnnnnnn cgatcg                                                     16

<210> SEQ ID NO 39
<211> LENGTH: 20
<212> TYPE: DNA
<213> ORGANISM: Artificial
<220> FEATURE:
<223> OTHER INFORMATION: synthetic primer

<400> SEQUENCE: 39
caatctatga ccgtagattc                                                 20

<210> SEQ ID NO 40
<211> LENGTH: 20
<212> TYPE: DNA
<213> ORGANISM: Artificial
<220> FEATURE:
<223> OTHER INFORMATION: synthetic primer

<400> SEQUENCE: 40
accgtggttc ctccattgcc                                                 20

<210> SEQ ID NO 41
<211> LENGTH: 20
<212> TYPE: DNA
<213> ORGANISM: Artificial
<220> FEATURE:
<223> OTHER INFORMATION: synthetic primer

<400> SEQUENCE: 41
gactggcact tggaagcggg                                                 20

<210> SEQ ID NO 42
<211> LENGTH: 19
<212> TYPE: DNA
<213> ORGANISM: Artificial
<220> FEATURE:
<223> OTHER INFORMATION: synthetic primer

<400> SEQUENCE: 42
ggaccaagct ggtactttc                                                  19

<210> SEQ ID NO 43
<211> LENGTH: 21
<212> TYPE: DNA
<213> ORGANISM: Artificial
<220> FEATURE:
<223> OTHER INFORMATION: synthetic primer

<400> SEQUENCE: 43
cgtggtacca gtctgccagg g                                             21

<210> SEQ ID NO 44
<211> LENGTH: 21
<212> TYPE: DNA
<213> ORGANISM: Artificial
<220> FEATURE:
<223> OTHER INFORMATION: synthetic primer

<400> SEQUENCE: 44
ggcagcatca gtcacggtca g                                             21

<210> SEQ ID NO 45
<211> LENGTH: 23
<212> TYPE: DNA
<213> ORGANISM: Artificial
<220> FEATURE:
<223> OTHER INFORMATION: synthetic primer

<400> SEQUENCE: 45
caccagcatg agctcaaagc tac                                           23

<210> SEQ ID NO 46
<211> LENGTH: 24
<212> TYPE: DNA
<213> ORGANISM: Artificial
<220> FEATURE:
<223> OTHER INFORMATION: synthetic primer

<400> SEQUENCE: 46
caccgcgatg tctcttcttc gtag                                          24

<210> SEQ ID NO 47
<211> LENGTH: 23
<212> TYPE: DNA
<213> ORGANISM: Artificial
<220> FEATURE:
<223> OTHER INFORMATION: synthetic primer

<400> SEQUENCE: 47
tgragrtgga asggatgwgg tcc                                           23

<210> SEQ ID NO 48
<211> LENGTH: 22
<212> TYPE: DNA
<213> ORGANISM: Artificial
<220> FEATURE:
<223> OTHER INFORMATION: synthetic primer

<400> SEQUENCE: 48
gtccctgtac tactccagat cc                                            22

<210> SEQ ID NO 49
<211> LENGTH: 22
<212> TYPE: DNA
<213> ORGANISM: Artificial
<220> FEATURE:
<223> OTHER INFORMATION: synthetic primer -continued

```
<400> SEQUENCE: 49
ccagcaggaa gcgtgatcga ac                                              22

<210> SEQ ID NO 50
<211> LENGTH: 27
<212> TYPE: DNA
<213> ORGANISM: Artificial
<220> FEATURE:
<223> OTHER INFORMATION: synthetic primer

<400> SEQUENCE: 50
gtaatcatgt atcacctggg ctcaagg                                         27

<210> SEQ ID NO 51
<211> LENGTH: 20
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 51
acgaacgagt ancgttgncc                                                 20

<210> SEQ ID NO 52
<211> LENGTH: 7
<212> TYPE: PRT
<213> ORGANISM: Cerrena unicolor

<400> SEQUENCE: 52

Gly Gln Arg Tyr Ser Phe Val
1               5

<210> SEQ ID NO 53
<211> LENGTH: 19
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t

<400> SEQUENCE: 53
ctggttggtt ngcattnag                                                  19

<210> SEQ ID NO 54
<211> LENGTH: 6
<212> TYPE: PRT
<213> ORGANISM: Cerrena unicolor

<400> SEQUENCE: 54

Leu Asn Ala Asn Gln Pro
1               5
```

```
<210> SEQ ID NO 55
<211> LENGTH: 20
<212> TYPE: DNA
<213> ORGANISM: Artificial
<220> FEATURE:
<223> OTHER INFORMATION: synthetic primer

<400> SEQUENCE: 55
cacacgaccc ctgaccgttg                                               20

<210> SEQ ID NO 56
<211> LENGTH: 20
<212> TYPE: DNA
<213> ORGANISM: Artificial
<220> FEATURE:
<223> OTHER INFORMATION: synthetic primer

<400> SEQUENCE: 56
tgaccggtga tcaacgtccc                                               20

<210> SEQ ID NO 57
<211> LENGTH: 20
<212> TYPE: DNA
<213> ORGANISM: Artificial
<220> FEATURE:
<223> OTHER INFORMATION: synthetic primer

<400> SEQUENCE: 57
ggcgcagaca tcaatcacag                                               20

<210> SEQ ID NO 58
<211> LENGTH: 20
<212> TYPE: DNA
<213> ORGANISM: Artificial
<220> FEATURE:
<223> OTHER INFORMATION: synthetic primer

<400> SEQUENCE: 58
tcttcagcat caacaacgcc                                               20

<210> SEQ ID NO 59
<211> LENGTH: 18
<212> TYPE: DNA
<213> ORGANISM: Artificial
<220> FEATURE:
<223> OTHER INFORMATION: synthetic primer

<400> SEQUENCE: 59
tccggcaagc acggttgg                                                 18

<210> SEQ ID NO 60
<211> LENGTH: 20
<212> TYPE: DNA
<213> ORGANISM: Artificial
<220> FEATURE:
<223> OTHER INFORMATION: synthetic primer

<400> SEQUENCE: 60
tcgtcttcgc tgagggcatc                                               20

<210> SEQ ID NO 61
<211> LENGTH: 20
<212> TYPE: DNA
<213> ORGANISM: Artificial
<220> FEATURE:
<223> OTHER INFORMATION: synthetic primer
```

<400> SEQUENCE: 61
cagaccgctg cagccaaccc                                                                                              20

<210> SEQ ID NO 62
<211> LENGTH: 20
<212> TYPE: DNA
<213> ORGANISM: Artificial
<220> FEATURE:
<223> OTHER INFORMATION: synthetic primer

<400> SEQUENCE: 62
aacacggaga cagtccaaac                                                                                              20

<210> SEQ ID NO 63
<211> LENGTH: 23
<212> TYPE: DNA
<213> ORGANISM: Artificial
<220> FEATURE:
<223> OTHER INFORMATION: synthetic primer

<400> SEQUENCE: 63
cacctctcga gatgggattg aac                                                                                          23

<210> SEQ ID NO 64
<211> LENGTH: 22
<212> TYPE: DNA
<213> ORGANISM: Artificial
<220> FEATURE:
<223> OTHER INFORMATION: synthetic primer

<400> SEQUENCE: 64
cgtttaaata gcagttcctt tc                                                                                           22

<210> SEQ ID NO 65
<211> LENGTH: 48
<212> TYPE: DNA
<213> ORGANISM: Artificial
<220> FEATURE:
<223> OTHER INFORMATION: synthetic primer

<400> SEQUENCE: 65
ggactagtgt cgccgtttac aaacgcgcaa tcggtccagt cactgacc                                                               48

<210> SEQ ID NO 66
<211> LENGTH: 2159
<212> TYPE: DNA
<213> ORGANISM: Artificial
<220> FEATURE:
<223> OTHER INFORMATION: synthetic PCR fragment

<400> SEQUENCE: 66
actagtgtcg ccgtttacaa acgcgcaatc ggtccagtca ctgacctaca tatagtgaac        60
cagaatctcg acccagatgg tttcaaccgc cccactgtac tcgcaggtgg tactttcccc       120
ggtcctctga ttcgtggtaa caaggtacgc ttcataaccg ccctccgtag acgtaggctt       180
cggctgacat gaccatcatc tgtagggaga taactttaaa attaatgtga ttgacgactt       240
gacagagcac agtatgctca aggctacgtc catcgtaagt ccctgattaa cgtttcacct       300
ggtcatatcg ctcaacgtct cgaagcactg gcatgggttc ttccagaagg gaaccaactg       360
ggccgatggc cccgcctttg tcacccaatg tcctatcaca tcaggaaacg ccttcctgta       420
tgatttcaac gttccggacc aagctggtac tttctggtac cacagccatc tctctacaca       480
gtattgtgac ggtcttcgtg gtgcctttgt cgtctatgat cctaatgatc caacaagca       540

```
actctatgat gttgataacg gcaagttcct tgcatatttc atttctatca tatcctcacc    600
tgtattggca cagaaagcac cgtgattacc ttggctgatt ggtatcatgc ccttgctcag    660
actgtcactg gtgtcgcgtg agtgacaaat ggccctcaat tgttcacata ttttcctgat    720
tatcatatga tagagtatct gatgcaacgt tgatcaacgg attgggacgt tcggccaccg    780
gccccgcaaa tgcccctctg gcggtcatca gtgtcgagcg gaataagagg tcagttccat    840
aattatgatt atttcccgcg ttacttccta acaattattt tgtatccct ccacagatat    900
cgtttccgat tggtttctat ttcttgcgac cctaacttta ttttctcaat tgaccaccac    960
ccaatgaccg taattgagat ggacggtgtt aatacccaat ctatgaccgt agattcgatc    1020
caaatattcg caggtcaacg atattcattt gtcgtaggtt attataaact gcccaccgat   1080
catctctcac gtaactgtta tagatgcaag ccaaccaacc agttggaaat tattggatcc   1140
gcgctaaacc taatgttggg aacacaactt ccttggagg cctgaactcc gctatattac    1200
gatatgtggg agcccctgac caagaaccga ccactgacca acacccaac tctacaccgc    1260
tcgttgaggc gaacctacga ccctcgtct atactcctgt ggtatgttgt tctcgttaca    1320
tataccaaac ctaatatgaa gactgaacgg atctactagc cgggacagcc attccctggc   1380
ggtgctgata tcgtcaagaa cttagctttg ggtttcgtac gtgtatttca cttcccttt    1440
ggcagtaact gaggtggaat gtatatagaa tgccgggcgt ttcacaatca atggagcgtc   1500
cctcacacct cctacagtcc ctgtactact ccagatcctc agtggtactc acaatgcaca   1560
ggatcttctc ccagcaggaa gcgtgatcga acttgaacag aataaagttg tcgaaatcgt   1620
tttgcccgct gcgggcgccg ttggcggtcc tcatccttt cacttacatg gtgtaagtat   1680
cagacgtcct catgcccata ttgctccgaa ccttacacac ctgatttcag cacaatttct   1740
gggtggttcg tagcgccggt caaaccacat acaatttcaa tgatgctcct atccgtgatg   1800
ttgtcagtat tggcggtgca aacgatcaag tcacgatccg atttgtggta tgtatctcgt   1860
gccttgcatt cattccacga gtaatgatcc ttacacttcg ggttctcaga ccgataaccc   1920
tggcccatgg ttccttcact gtcacattga ctggcatttg gaggctgggt tcgctgtagt   1980
cttttgcggag ggaatcaatg gtactgcagc tgctaatcca gtcccaggta agactctcgc    2040
tgctttgcgt aatatctatg aatttaaatc atatcaattt gcagcggctt ggaatcaatt    2100
gtgcccattg tatgatgcct tgagcccagg tgatacatga ttacaagggt gggcgcgcc     2159
```

<210> SEQ ID NO 67  
<211> LENGTH: 1523  
<212> TYPE: DNA  
<213> ORGANISM: Artificial  
<220> FEATURE:  
<223> OTHER INFORMATION: synthetic codon optimized laccase B

<400> SEQUENCE: 67

```
actagtgtcg ccgtttacaa acgcgcaatc ggtcccgtca ctgacctgca tattgtgaac     60
cagaatctcg accccgatgg tttcaaccgc cccactgtcc tcgcaggtgg tactttcccc    120
ggtcctctga ttcgtggtaa caagggagat aactttaaaa ttaatgtgat tgacgacttg    180
acagagcaca gcatgctcaa ggctacgtcc atccactggc atggcttctt ccagaaggga    240
accaactggg ccgatggccc cgcctttgtc acccaatgtc ctatcacatc aggaaacgcc    300
ttcctgtacg atttcaacgt tccggaccaa gctggtactt tctggtacca cagccatctc    360
tctacacagt actgtgacgg tcttcgtggt gcctttgtcg tctacgatcc taatgatccc    420
```

```
aacaagcaac tctacgatgt tgataacggc aacaccgtga ttaccttggc tgattggtac    480
catgcccttg ctcagactgt cactggtgtc gcagtctctg atgaacgtt gatcaacgga     540 ttgggacgtt cggccaccgg ccccgcaaat gcccctctgg cggtcatcag cgtcgagcgc    600
aataagcgct atcgtttccg attggttct atttcttgcg accctaactt tattttctca     660
attgaccacc accccatgac cgtcattgag atggacggtg ttaataccca atctatgacc    720
gtagattcga tccaaatctt cgcaggtcaa cgatactcat ttgtcatgca agccaaccaa    780
ccagttggaa attactggat ccgcgctaaa cctaatgttg caacacaac tttccttgga     840 ggcctgaact ccgctatctt gcgatacgtg ggagcccctg accaagaacc gaccactgac    900
caaacaccca actctacacc gctcgttgag gcgaacctgc gaccctcgt ctacactcct     960 gtgccgggac agccattccc tggcggtgct gatatcgtca agaacttggc tttgggtttc   1020
aatgccgggc gtttcacaat caatggagcg tccctcacac ctcctacagt ccctgtcctg   1080
ctccagatcc tcagcggtac tcacaatgca caggatcttc tcccggcagg aagcgtgatc   1140
gaacttgaac agaataaagt tgtcgaaatc gttttgcccg ctgcgggcgc cgttggcggt   1200
cctcatcctt ttcacttgca tggtcacaat ttctgggtgg ttcgtagcgc cggtcaaacc   1260
acatacaatt tcaatgatgc tcctatccgt gatgttgtca gcattggcgg tgcaaacgat   1320
caagtcacga tccgatttgt gaccgataac cctggcccat ggttccttca ctgtcacatt   1380
gactggcatt tggaggctgg attcgctgtc gtctttgcgg agggaatcaa tggtactgca   1440
gctgctaatc ccgtcccggc ggcttggaat caattgtgcc cgttgtacga tgccttgagc   1500
ccgggtgata catgaggcgc gcc                                          1523

<210> SEQ ID NO 68
<211> LENGTH: 47
<212> TYPE: DNA
<213> ORGANISM: Artificial
<220> FEATURE:
<223> OTHER INFORMATION: synthetic primer

<400> SEQUENCE: 68
ggactagtgt cgccgtttac aaacgcgcaa ttgggcccgt ggccgac                 47

<210> SEQ ID NO 69
<211> LENGTH: 33
<212> TYPE: DNA
<213> ORGANISM: Artificial
<220> FEATURE:
<223> OTHER INFORMATION: synthetic primer

<400> SEQUENCE: 69
aaggcgcgcc ttaaatagca gttcctttct tag                                33

<210> SEQ ID NO 70
<211> LENGTH: 1550
<212> TYPE: DNA
<213> ORGANISM: Artificial
<220> FEATURE:
<223> OTHER INFORMATION: synthetic codon optimized laccase D

<400> SEQUENCE: 70
actagtgtcg ccgtttacaa acgcgctatt ggaccagttg ctgatctgca catcgttaac     60
aaggatttgg ccccagacgg cgtccagcgc ccaactgttc tggccggtgg aacttttccg    120
ggcacgctga ttaccggtca aaagggcgac aacttccagc tgaacgtgat tgatgacctg    180
accgacgatc gcatgttgac ccctacttcg atccattggc atggtttctt ccagaaggga    240
```

```
accgcctggg ccgacggtcc ggctttcgtt acacagtgcc ctattatcgc agacaactcc      300
ttcctctacg atttcgacgt tcccgaccag gcgggcacct tctggtacca ctcacacttg      360
tctacacagt actgcgacgg tctgcgcggt gccttcgttg tttacgaccc caacgaccct      420
cacaaggacc tttatgatgt cgatgacggt ggcacagtta tcacattggc tgactggtat      480
cacgtcctcg ctcagaccgt tgtcggagct gctacacccg actctacgct gattaacggc      540
ttgggacgca gccagactgg ccccgccgac gctgagctgg ccgttatctc tgttgaacac      600
aacaagagat accgtttcag actcgtctcc atctcgtgcg atcccaactt cacttttagc      660
gtcgacggtc acaacatgac ggttatcgag gttgatggcg tgaatacccg ccctctcacc      720
gtcgattcca ttcaaatttt cgccggccag cgatactcct tgtgctgaa tgccaatcag      780 cccgaggata actactggat ccgcgctatg cctaacatcg gacgaaacac cactacccett     840 gatggcaaga atgccgctat cctgcgatac aagaacgcca gcgttgagga gcccaaaacc      900
gtcggaggac ccgcgcagag cccattgaac gaggccgacc tgcgacctct ggtgcccgct      960
cctgtccctg gcaacgcagt tcctggtggt gcggacatca ccaccgcct gaacctgaca     1020 ttcagcaacg gcctcttctc tatcaataac gcatcattta caaccccag cgtccctgcc     1080 ttgttgcaga ttcttccgg cgcacaaaac gctcaggatc tgcttccac cggttcttat      1140 atcggcttgg agttgggcaa ggtcgttgaa ctcgtgatcc ctcccttggc cgttggtggc     1200
ccccatccat tccacttgca cggccacaac ttttgggtcg tccgaagcgc tggttctgac     1260
gagtataatt tcgacgatgc aattttgcgc gacgtggtca gcattggcgc gggaactgac     1320
gaggttacta tccgttttgt cactgataac ccaggcccct tggttcctcca ttgccacatc     1380 gactggcacc tcgaagccgg cctcgccatt gtttcgccg aaggcatcaa tcaaaccgca     1440
gccgccaacc cgactccaca ggcctgggac gaactctgcc ccaagtataa cggactctcc     1500
gcttcccaga aagtgaagcc caagaaggga acagccatct aaggcgcgcc               1550
```

<210> SEQ ID NO 71
<211> LENGTH: 1507
<212> TYPE: DNA
<213> ORGANISM: Artificial
<220> FEATURE:
<223> OTHER INFORMATION: synthetic codon optimized laccase D

<400> SEQUENCE: 71

```
ggatcctgaa gctatcggtc cggttgcaga tttacacatc gtaaacaaag atcttgcacc       60
tgacggcgtt caacgtccaa ctgtacttgc tggtggaaca ttccctggta cacttattac      120
tggtcaaaaa ggtgacaact tccaattaaa cgtaattgac gatcttacag atgaccgtat      180
gcttacaccg acttcaattc actggcacgg tttctttcaa aaaggaacag catgggctga      240
tggtcctgca ttcgttacac aatgtccaat cattgctgat aactcttttcc tttacgattt      300 tgacgttcct gatcaagctg gtacattctg gtatacactca cacttatcca cacaatactg      360
cgatggactt cgcggagctt tcgtagttta cgacccaaac gatcctcata agacccttta      420
cgatgtagat gatggtggaa cagttatcac attagctgat tggtaccatg tacttgctca      480
aacagttgta ggtgcagcta caccagattc aacacttatc aatggattag acgttctca      540 aactggtcct gctgacgcag aacttgctgt aatctctgtt gaacataaca acgttacag      600 attccgtctt gttagcattt cttgcgatcc aaacttcaca ttttcagttg acggacataa      660
catgacagtt atcgaagtag atggtgtaaa cacacgtcca cttactgtag actctatcca      720
```

| | |
|---|---|
| aatcttcgca ggacaacgtt actcattcgt attaaacgca aatcaaccag aagataacta | 780 |
| ctggattcgt gcaatgccaa acatcggacg taacactaca actcttgacg gcaaaaacgc | 840 |
| agctattctt cgttacaaaa acgcttctgt tgaagaacct aaaacagttg gtggaccagc | 900 |
| acaatcacca cttaacgaag ctgacttacg tccactggtt ccagcacctg tacctggaaa | 960 |
| cgctgtacca ggaggtgctg atattaatca tagacttaac cttactttct ctaacggtct | 1020 |
| gttctcaatc aacaacgctt cattcacaaa tccttcagtt ccagcacttt tacaaattct | 1080 |
| tagcggtgca caaaatgctc aggatctttt accaactgga tcttacattg gtcttgaact | 1140 |
| gggtaaagta gttgaattag taattcctcc gcttgctgta ggtggaccac atcctttcca | 1200 |
| tcttcacggt cataacttct gggttgtacg ttctgctggt tcagatgaat acaacttcga | 1260 |
| tgacgcaatt cttcgtgatg ttgtatctat tggtgctgga acagatgaag taactattcg | 1320 |
| tttcgtaaca gataaccctg gtccttggtt cttacattgt catatcgatt ggcatcttga | 1380 |
| agctggactt gctattgttt tcgctgaagg aatcaatcaa acagctgcag ctaacccaac | 1440 |
| acctcaagca tgggacgaat tatgtccaaa atacaacgca ctttctccag gagatactta | 1500 |
| aaagctt | 1507 |

<210> SEQ ID NO 72
<211> LENGTH: 34
<212> TYPE: DNA
<213> ORGANISM: Artificial
<220> FEATURE:
<223> OTHER INFORMATION: synthetic primer

<400> SEQUENCE: 72
gcagatctgc gatgtctctt cttcgtagct tgac                         34

<210> SEQ ID NO 73
<211> LENGTH: 42
<212> TYPE: DNA
<213> ORGANISM: Artificial
<220> FEATURE:
<223> OTHER INFORMATION: synthetic primer

<400> SEQUENCE: 73
gaggtcacct ctagatcatg tatcacctgg gctcaaggca tc                 42

<210> SEQ ID NO 74
<211> LENGTH: 51
<212> TYPE: DNA
<213> ORGANISM: Artificial
<220> FEATURE:
<223> OTHER INFORMATION: synthetic primer

<400> SEQUENCE: 74
ttgctagcaa cgtgatctcc aagcgtgcaa tcggtccagt cactgaccta c       51

<210> SEQ ID NO 75
<211> LENGTH: 32
<212> TYPE: DNA
<213> ORGANISM: Artificial
<220> FEATURE:
<223> OTHER INFORMATION: synthetic primer

<400> SEQUENCE: 75
acgcagcctg aactagttgc gatcctctag ag                            32

<210> SEQ ID NO 76
<211> LENGTH: 37

```
<212> TYPE: DNA
<213> ORGANISM: Artificial
<220> FEATURE:
<223> OTHER INFORMATION: synthetic primer

<400> SEQUENCE: 76
ctctgatcaa ggtcatcagg tgtcgcccgg ggacagg                              37

<210> SEQ ID NO 77
<211> LENGTH: 6
<212> TYPE: PRT
<213> ORGANISM: Artificial
<220> FEATURE:
<223> OTHER INFORMATION: synthetic Kex2 site

<400> SEQUENCE: 77

Asn Val Ile Ser Lys Arg
1               5
```

LACCASES, COMPOSITIONS AND METHODS OF USE

CROSS-REFERENCE TO RELATED APPLICATIONS

The present application is a continuation of U.S. patent application Ser. No. 11/954,804, filed 12 Dec. 2007, now U.S. Pat. No. 8,105,812 which claims priority to U.S. Provisional Patent Application Ser. No. 60/875,518, entitled "Novel Laccases, Compositions and Methods of Use", filed 18 Dec. 2006 and U.S. Provisional Patent Application Ser. No. 60/875,454, entitled "Laccase Mediators and Methods of Use", filed 18 Dec. 2006.

SEQUENCE LISTING

The sequence listing submitted via EFS, in compliance with 37 C.F.R. §1.52(e), is incorporated herein by reference. The sequence listing text file submitted via EFS contains the file "30942-PCT_seqlist.txt" created on Nov. 28, 2011 which is 78,223 bytes in size.

FIELD OF THE INVENTION

The present invention relates to laccases and nucleic acid sequences encoding the laccases, and to enzymatic methods for bleaching materials.

BACKGROUND OF THE INVENTION

Laccases are copper-containing enzymes that are known to be good oxidizing agents in the presence of oxygen. Laccases are found in microbes, fungi, and higher organisms. Laccase enzymes are used for many applications, including pulp and textiles bleaching, treatment of pulp waste water, de-inking, industrial color removal, bleaching laundry detergents, oral care teeth whiteners, and as catalysts or facilitators for polymerization and oxidation reactions.

Laccases can be utilized for a wide variety of applications in a number of industries, including the detergent industry, the paper and pulp industry, the textile industry and the food industry. In one application, phenol oxidizing enzymes are used as an aid in the removal of stains, such as food stains, from clothes during detergent washing.

Most laccases exhibit pH optima in the acidic pH range while being inactive in neutral or alkaline pHs.

Laccases are known to be produced by a wide variety of fungi, including species of the genii *Aspergillus, Neurospora, Podospora, Botrytis, Pleurotus, Formes, Phlebia, Trametes, Polyporus, Stachybotrys, Rhizoctonia, Bipolaris, Curvularia, Amerosporium,* and *Lentinus*. However, there remains a need for laccases having different performance profiles in various applications.

For many applications, the oxidizing efficiency of a laccase can be improved through the use of a mediator, also known as an enhancing agent. Systems that include a laccase and a mediator are known in the art as laccase-mediator systems (LMS). The same compounds can also be used to activate or initiate the action of laccase.

There are several known mediators for use in a laccase-mediator system. These include HBT (1-hydroxybenzotriazole), ABTS [2,2'-azinobis(3-ethylbenzothiazoline-6-sulfinic acid)], NHA (N-hydroxyacetanilide), NEIAA (N-acetyl-N-phenylhydroxylamine), HBTO (3-hydroxy 1,2,3-benzotriazin-4(3H)-one), and VIO (violuric acid). In addition, there are several compounds containing NH—OH or N—O that have been found to be useful as mediators.

Functional groups and substituents have large effects on mediator efficiency. Even within the same class of compounds, a substituent can change the laccase specificity towards a substrate, thereby increasing or decreasing mediator efficiency greatly. In addition, a mediator may be effective for one particular application but unsuitable for another application. Another drawback for current mediators is their tendency to polymerize during use. Thus, there is a need to discover efficient mediators for specific applications. One such application is the bleaching of textiles, wherein it is also important that the mediators are not unduly expensive or hazardous. Other applications of the laccase-mediator system are given below.

Thus, there is a need to identify additional mediators that activate laccase, and/or enhance the activity of enzymes that exhibit laccase activity.

SUMMARY OF THE INVENTION

Described herein are novel laccases, nucleic acid sequences encoding such laccases, and vectors and host cells for expressing the laccases.

DETAILED DESCRIPTION OF THE INVENTION

Figure 1:
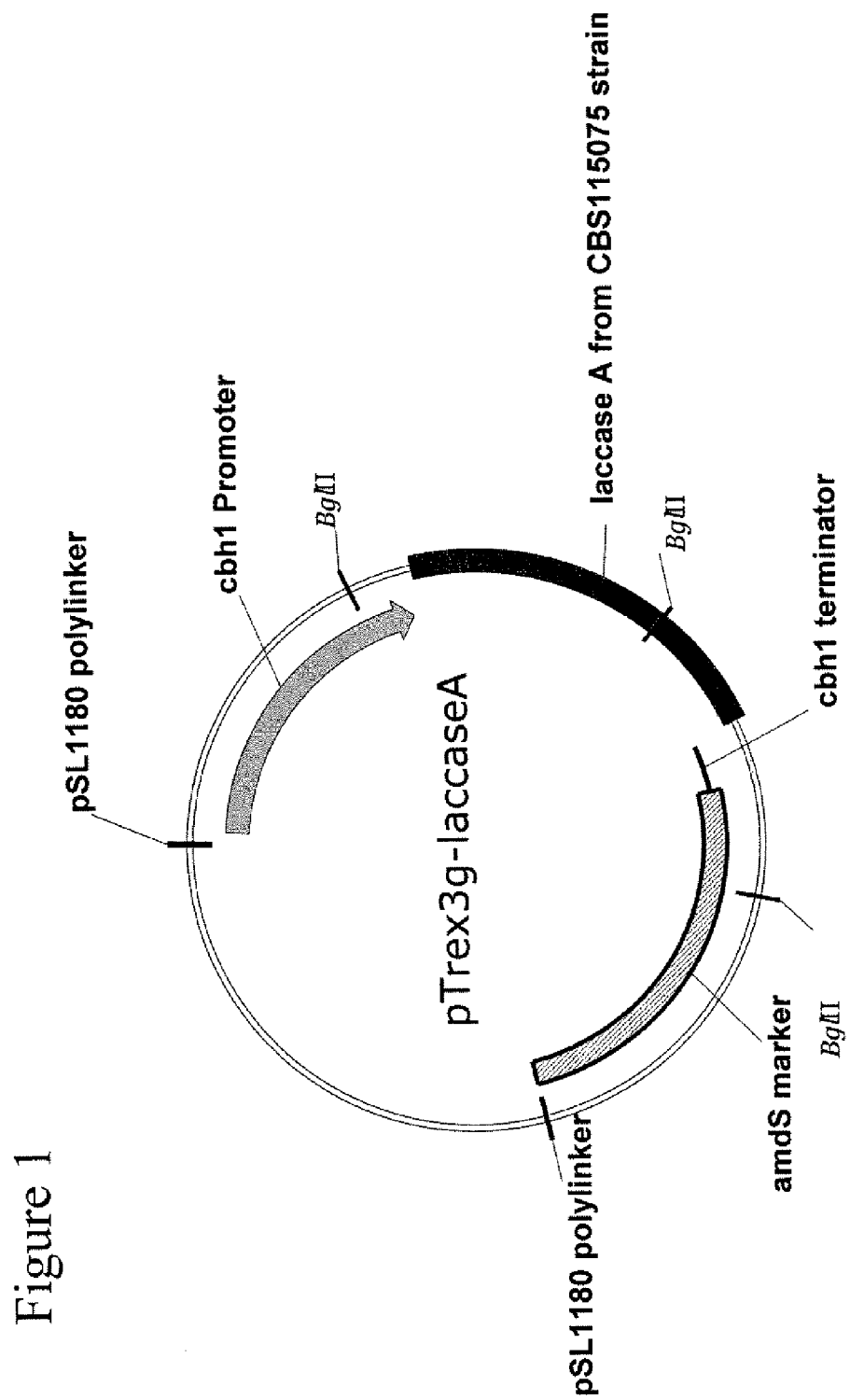
FIG. 1 is a schematic of the *Trichoderma* expression plasmid, pTrex3g-laccaseA, used in Example 7. The laccase A gene may be replaced with other laccase genes described herein.

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, N.Y. (1991) provide one of skill with a general dictionary of many of the terms used in this invention. Although any methods and materials similar or equivalent to those described herein can be used in the practice or testing of the present invention, the preferred methods and materials are described. Numeric ranges are inclusive of the numbers defining the range. It is to be understood that this invention is not limited to the particular methodology, protocols, and reagents described, as these may vary.

The headings provided herein are not limitations of the various aspects or embodiments of the invention which can be had by reference to the specification as a whole. Accordingly, the terms defined immediately below are more fully defined by reference to the specification as a whole.

All publications cited herein are expressly incorporated herein by reference for the purpose of describing and disclosing compositions and methodologies which might be used in connection with the invention.

I. Laccase and Laccase Related Enzymes

In the context of this invention, laccases and laccase related enzymes contemplate any laccase enzyme comprised by the enzyme classification (EC 1.10.3.2). The laccase enzymes are known from microbial and plant origin. The microbial laccase enzyme may be derived from bacteria or fungi (including filamentous fungi and yeasts) and suitable examples include a laccase derivable from a strain of *Aspergillus, Neurospora*, e.g. *N. crassa, Podospora, Botrytis, Collybia, Cerrena, Stachybotrys, Panus*, e.g., *Panus rudis, Theilava, Fomes, Lentinus, Pleurotus, Trametes*, e.g. *T. villosa* and *T. versicolor, Rhizoctonia*, e.g. *R. solani, Coprinus*, e.g. *C. plicatilis* and *C. cinereus, Psatyrella, Myceliophthora*, e.g. *M. thermonhila, Schytalidium, Phlebia*, e.g., *P. radita* (WO 92/01046), or *Coriolus*, e.g. *C. hirsutus* (JP 2-238885), *Spongipellis* sp., *Polyporus, Ceriporiopsis subvermispora, Ganoderma tsunodae* and *Trichoderma*.

The laccase or the laccase related enzyme may furthermore be produced by a method comprising cultivating a host cell transformed with a recombinant DNA vector which carries a DNA sequence encoding said laccase as well as DNA sequences permitting the expression of the DNA sequence encoding the laccase, in a culture medium under conditions permitting the expression of the laccase enzyme, and recovering the laccase from the culture.

The expression vector may be transformed into a suitable host cell, such as a fungal cell, preferred examples of which are species of *Aspergillus*, most preferably *Aspergillus oryzae* and *Aspergillus niger*, and species of *Fusarium*, most preferably *Fusarium venenatum*. Fungal cells may be transformed by a process involving protoplast formation and transformation of the protoplasts followed by regeneration of the cell wall in a manner known per se. The use of *Aspergillus* as a host microorganism is described in EP 238,023. The use of *Fusarium* as a host microorganism is described in WO 96/00787 and WO 97/08325.

Alternatively, the host organism may be a bacterium, in particular strains of *Bacillus, Pseudomonas, Streptomyces*, or *E. coli*. The transformation of bacterial cells may be performed according to conventional methods, e.g., as described in T. Maniatis et al., Molecular Cloning: A Laboratory Manual, Cold Spring Harbor, 1982. The screening of appropriate DNA sequences and construction of vectors may also be carried out by standard procedures, cf. T. Maniatis et al., op. cit.

The medium used to cultivate the transformed host cells may be any conventional medium suitable for growing the host cells in question. The expressed enzyme may conveniently be secreted into the culture medium and may be recovered therefrom by well-known procedures including separating the cells from the medium by centrifugation or filtration, precipitating proteinaceous components of the medium by means of a salt such as ammonium sulphate, followed by chromatographic procedures such as ion exchange chromatography, affinity chromatography, or the like.

In an embodiment, the expression host may be a *Trichoderma reesei* with the laccase coding region under the control of a CBH1 promoter and terminator. (See, e.g., U.S. Pat. No. 5,861,271). The expression vector may be pTrex3g, as disclosed in U.S. patent application Ser. No. 11/245,628 filed 7 Oct. 2005.

In this manner the following novel genes and laccases were prepared:

```
A. Cerrena laccase A1 gene from CBS115.075 strain having the
sequence
                                              (SEQ ID No. 1)
ATGAGCTCAA AGCTACTTGC TCTTATCACT GTCGCTCTCG TCTTGCCACT     50

AGGCACCGAC GCCGGCATCG GTCCTGTTAC CGACTTGCGC ATCACCAACC    100

AGGATATCGC TCCAGATGGC TTCACCCGAC CAGCGGTACT AGCTGGGGGC    150

ACATTCCCTG GAGCACTTAT TACCGGTCAG AAGGTATGGG AGATCAACTT    200

GGTTGAATAG AGAAATAAAA GTGACAACAA ATCCTTATAG GGAGACAGCT    250

TCCAAATCAA TGTCATCGAC GAGCTTACCG ATGCCAGCAT GTTGACCCAG    300

ACATCCATTG TGAGTATAAT TTAGGTCCGC TCTTCTGGCT ATCCTTTCTA    350

ACTCTTACCG TCTAGCATTG GCACGGCTTC TTTCAGAAGG GATCTGCGTG    400

GGCCGATGGT CCTGCCTTCG TTACTCAATG CCCTATCGTC ACCGGAAATT    450

CCTTCCTGTA CGACTTTGAT GTTCCCGACC AACCTGGTAC TTTCTGGTAC    500

CATAGTCACT TGTCTACTCA ATATTGCGAT GGTCTTCGTG GCCCGTTCGT    550
```

-continued

```
TGTATACGAT CCAAAGGATC CTAATAAACG GTTGTACGAC ATTGACAATG    600
GTATGTGCAT CATCATAGAG ATATAATTCA TGCAGCTACT GACCGTGACT    650
GATGCTGCCA GATCATACGG TTATTACCCT GGCAGACTGG TACCACGTTC    700
TCGCAAGAAC TGTTGTCGGA GTCGCGTAAG TACAGTCTCA CTTATAGTGG    750
TCTTCTTACT CATTTTGACA TAGGACACCC GACGCAACCT TGATCAACGG    800
TTTGGGCCGT TCTCCAGACG GGCCAGCAGA TGCTGAGTTG GCTGTCATCA    850
ACGTTAAACG CGGCAAACGG TATGTTATTG AACTCCCGAT TTCTCCATAC    900
ACAGTGAAAT GACTGTCTGG TCTAGTTATC GATTTCGTCT GGTCTCCATC    950
TCATGTGACC CTAATTACAT CTTTTCTATC GACAACCATT CTATGACTGT   1000
CATCGAAGTC GATGGTGTCA ACACCCAATC CCTGACCGTC GATTCTATTC   1050
AAATCTTCGC AGGCCAACGA TACTCGTTCG TCGTAAGTCT CTTTGCACGA   1100
TTACTGCTTC TTTGTCCATT CTCTGACCTG TTTAAACAGC TCCATGCCAA   1150
CCGTCCTGAA ACAACTATT GGATCAGGGC CAAACCTAAT ATCGGTACGG   1200
ATACTACCAC AGACAACGGC ATGAACTCTG CCATTCTGCG AGACAACGGC   1250
GCACCTGTTG CGGAACCGCA AACTGTTCAA TCTCCCAGTC TCACCCCTTT   1300
GCTCGAACAG AACCTTCGCC CTCTCGTGTA CACTCCTGTG GTATGTTTCA   1350
AAGCGTTGTA ATTTGATTGT GGTCATTCTA ACGTTACTGC GTTTGCATAG   1400
CCTGGAAACC CTACGCCTGG CGGCGCCGAT ATTGTCCATA CTCTTGACTT   1450
GAGTTTTGTG CGGAGTCAAC ATTCGTAAAG ATAAGAGTGT TTCTAATTTC   1500
TTCAATAATA GGATGCTGGT CGCTTCAGTA TCAACGGTGC CTCGTTCCTT   1550
GATCCTACCG TCCCCGTTCT CCTGCAAATT CTCAGCGGCA CGCAGAATGC   1600
ACAAGATCTA CTCCCTCCTG GAAGTGTGAT TCCTCTCGAA TTAGGCAAGG   1650
TCGTCGAATT AGTCATACCT GCAGGTGTCG TCGGTGGACC TCATCCGTTC   1700
CATCTCCATG GGGTACGTAA CCCGAACTTA TAACAGTCTT GGACTTACCC   1750
GCTGACAAGT GCATAGCATA ACTTCTGGGT CGTGCGAAGT GCCGGAACCG   1800
ACCAGTACAA CTTTAACGAT GCCATTCTCC GAGACGTCGT CAGTATAGGA   1850
GGAACCGGGG ATCAAGTCAC CATTCGTTTC GTGGTATGTT TCATTCTTGT   1900
GGATGTATGT GCTCTAGGAT ACTAACCGGC TTGCGCGTAT AGACCGATAA   1950
CCCCGGACCG TGGTTCCTCC ATTGCCATAT CGACTGGCAC TTGGAAGCGG   2000
GTCTCGCTAT CGTATTTGCA GAGGGAATTG AAAATACTGC TGCGTCTAAT   2050
TTAACCCCCC GTACGCGGTT TCCCTCACAT CCTGGAGCTA AGCAGCTTAC   2100
TAACATACAT TTGCAGAGGC TTGGGATGAG CTTTGCCCGA AGTATAACGC   2150
GCTCAGCGCA CAAAGAAGG TTGCATCTAA GAAAGGCACT GCCATCTAAT   2200
TTTTGTAACA AACAAGGAGG GTCTCTTGTA CTTTTATTGG GATTTCTTTC   2250
TTGGGGTTTA TTGTTAAACT TGACTCTACT ATGTTTGGAA GACGAAAGGG   2300
GCTCGCGCAT TTATATACTA TCTCTCTTGG CATCACCTGC AGCTCAATCC   2350
TTCAACCACC TAA                                           2363
``` encoding the enzyme laccase A1, having the translated protein sequence (SEQ ID No. 2)
```
MSSKLLALIT VALVLPLGTD AGIGPVTDLR ITNQDIAPDG FTRPAVLAGG     50
TFPGALITGQ KGDSFQINVI DELTDASMLT QTSIHWHGFF QKGSAWADGP    100
```

-continued

```
AFVTQCPIVT GNSFLYDFDV PDQPGTFWYH SHLSTQYCDG LRGPFVVYDP      150
KDPNKRLYDI DNDHTVITLA DWYHVLARTV VGVATPDATL INGLGRSPDG      200
PADAELAVIN VKRGKRYRFR LVSISCDPNY IFSIDNHSMT VIEVDGVNTQ      250
SLTVDSIQIF AGQRYSFVLH ANRPENNYWI RAKPNIGTDT TTDSGMNSAI      300
LRYNGAPVAE PQTVQSPSLT PLLEQNLRPL VYTPVPGNPT PGGADIVHTL      350
DLSFDAGRFS INGASFLDPT VPVLLQILSG TQNAQDLLPP GSVIPLELGK      400
VVELVIPAGV VGGPHPFHLH GHNFWVVRSA GTDQYNFNDA ILRDVVSIGG      450
TGDQVTIRFV TDNPGPWFLH CHIDWHLEAG LAIVFAEGIE NTAASNLTPQ      500
AWDELCPKYN ALSAQKKLNP STT                                   523
```

B. *Cerrena* laccase A2 gene from CBS154.29 strain (SEQ ID No. 3)

```
ATGAGCTCAA AGCTACTTGC TCTTATTACT GTCGCTCTCG TCTTGCCACT       50
AGGCACTGAC GCCGGCATCG GTCCTGTTAC CGACTTGCGC ATCACCAACC      100
AGGATATCGC TCCAGATGGC TTCACCCGAC CAGCTGTACT GGCTGGGGGC      150
ACATTCCCCG GAGCACTGAT TACCGGTCAG AAGGTATGGG AGATCGATTT      200
CGTTGAATAG AGAAATACAA CTGAAAACAA ATTCTTATAG GGAGACAGCT      250
TCCAAATCAA TGTCATCGAC GAGCTTACCG ATGCCAGCAT GTTGACCCAG      300
ACATCCATTG TGAGTATAAT ATGGGTCCGC TCTTCTAGCT ATCCTTTCTA      350
ACTCTTACCC TCTAGCATTG GCACGGCTTC TTTCAGAAGG GATCTGCGTG      400
GGCCGATGGT CCTGCCTTCG TTACTCAATG TCCTATCGTC ACCGGAAATT      450
CCTTCCTGTA CGACTTTGAT GTCCCCGACC AACCTGGTAC TTTCTGGTAC      500
CATAGTCACT TGTCTACTCA ATATTGCGAT GGTCTTCGGG GCCCGTTCGT      550
TGTATACGAT CCAAAGGATC CTAATAAACG GTTGTACGAC ATTGACAATG      600
GTATGTGCAT CATCATAAAA ATATAATTCA TGCAGCTACT GACCGCGACT      650
GATGCTGCCA GATCATACGG TTATTACCCT GGCAGACTGG TACCACGTTC      700
TCGCACGAAC TGTTGTCGGA GTCGCGTAAG TACAGTCTGA CTTATAGTGG      750
TCTTCTTACT CATTTTGACA TAGGACACCC GACGCAACCT TGATCAACGG      800
TTTGGGCCGT TCTCCAGACG GGCCAGCAGA TGCTGAGTTG GCTGTCATCA      850
ACGTTAAACG CGGCAAACGG TATGTCATTG AACTCCCGAT TCTCCATTC       900
ACATTGAAAT GACTGTCTGG TCTAGTTATC GATTCCGTCT GGTCTCCATC      950
TCATGTGACC CTAATTACAT CTTTTCTATC GACAACCATT CTATGACTGT     1000
CATCGAAGTC GATGGTGTCA ACACCCAATC CCTGACCGTC GATTCTATCC     1050
AAATCTTCGC AGGCCAACGC TACTCGTTCG TCGTAAGTCT CTTTGAATGG     1100
TTGGTGCTTT TTCTGTCCAT TCTCTAACCT GTTTATACAG CTCCATGCCA     1150
ACCGTCCTGA AAACAACTAT TGGATCAGGG CCAAACCTAA TATCGGTACG     1200
GATACTACCA CAGACAACGG CATGAACTCT GCCATTCTGC GATACAACGG     1250
CGCACCTGTT GCGGAACCGC AAACTGTTCA ATCTCCCAGT CTCACCCCTT     1300
TGCTCGAACA GAACCTTCGC CCTCTCGTGT ACACTCCTGT GGTATGTTTC     1350
AAAGCGTTGT AATTTGATTG TGGTCATTCT AACGTTACTG CCTTTGCACA     1400
GCCTGGAAAT CCTACGCCTG GCGGGGCCGA TATTGTCCAT ACTCTTGACT     1450
TGAGTTTTGT GCGGAGTCAA CATTCGTAAA GATAAGAGTG TTTCTAATTT     1500
```

-continued

```
CTTCAATAAT AGGATGCTGG TCGCTTCAGT ATCAACGGTG CCTCGTTCCT    1550

TGATCCTACC GTCCCTGTTC TCCTGCAAAT TCTCAGCGGC ACGCAGAATG    1600

CACAAGATCT ACTCCCTCCT GGAAGTGTGA TTCCTCTCGA ATTAGGCAAG    1650

GTCGTCGAAT TAGTCATACC TGCAGGTGTT GTCGGTGGAC CTCATCCGTT    1700

CCATCTCCAT GGGGTACGTA ACCCGAACTT ATAACAGTCT TGGACTTACC    1750

CGCTGACAAG TGTATAGCAT AACTTCTGGG TCGTGCGAAG TGCCGGAACC    1800

GACCAGTACA ACTTTAACGA TGCCATTCTC CGAGACGTCG TCAGTATAGG    1850

AGGAACCGAG GATCAAGTCA CCATTCGATT CGTGGTATAT ACTTCATTCT    1900

TGTGGATGTA TGTGCTCTAG GATACTAACT GGCTTGCGCG TATAGACCGA    1950

TAACCCCGGA CCGTGGTTCC TCCATTGCCA TATCGACTGG CACTTGGAAG    2000

CGGGTCTCGC TATCGTATTT GCAGAGGGAA TTGAAAATAC TGCTGCGTCT    2050

AATCCAACCC CCCGTATGCG GTTTCCCACA CATTCTGAAT CTAAGCAGCT    2100

TACTAATATA CATTTGCAGA GGCTTGGGAT GAGCTTTGCC CGAAGTATAA    2150

CGCGCTCAAC GCACAAAAGA AGGTTGCATC TAAGAAAGGC ACTGCCATCT    2200

AATCCTTGTA ACAAACAAGG AGGGTCTCTT GTACTTTTAT TGGGATTTAT    2250

TTCTTGGGGT TTATTGTTCA ACTTGATTCT ACTATGTTTG GAAGTAGCGA    2300

TTACGAAAGG GGCTTGCGCA TTTATATACC ATCTTTCTTG GCACCACCTG    2350

CAGCTCAATC CTTCAACCAC CTAA                               2374
``` encoding the enzyme laccase A2, having the translated protein sequence shown in (SEQ ID No. 4)
```
MSSKLLALIT VALVLPLGTD AGIGPVTDLR ITNQDIAPDG FTRPAVLAGG     50

TFPGALITGQ KGDSFQINVI DELTDASMLT QTSIHWHGFF QKGSAWADGP    100

AFVTQCPIVT GNSFLYDFDV PDQPGTFWYH SHLSTQYCDG LRGPFVVYDP    150

KDPNKRLYDI DNDHTVITLA DWYHVLARTV VGVATPDATL INGLGRSPDG    200

PADAELAVIN VKRGKRYRFR LVSISCDPNY IFSIDNHSMT VIEVDGVNTQ    250

SLTVDSIQIF AGQRYSFVLH ANRPENNYWI RAKPNIGTDT TTDNGMNSAI    300

LRYNGAPVAE PQTVQSPSLT PLLEQNLRPL VYTPVPGNPT PGGADIVHTL    350

DLSFDAGRFS INGASFLDPT VPVLLQILSG TQNAQDLLPP GSVIPLELGK    400

VVELVIPAGV VGGPHPFHLH GHNFWVVRSA GTDQYNFNDA ILRDVVSIGG    450

TEDQVTIRFV TDNPGPWFLH CHIDWHLEAG LAIVFAEGIE NTAASNPTPQ    500

AWDELCPKYN ALNAQKKLNP STT                                523
```

C. Cerrena laccase B1 gene from CBS115.075 strain (SEQ ID No. 5)
```
ATGTCTCTTC TTCGTAGCTT GACCTCCCTC ATCGTACTAG TCATTGGTGC     50

ATTTGCTGCA ATCGGTCCAG TCACTGACCT ACATATAGTG AACCAGAATC    100

TCGACCCAGA TGGTTTCAAC CGCCCCACTG TACTCGCAGG TGGTACTTTC    150

CCCGGTCCTC TGATTCGTGG TAACAAGGTA CGCTTCATAA CCGCCCTCCG    200

TAGACGTAGG CTTCGGCTGA CATGACCATC ATCTGTAGGG AGATAACTTT    250

AAAATTAATG TGATTGACGA CTTGACAGAG CACAGTATGC TCAAGGCTAC    300

GTCCATCGTA AGTCCCTGAT TAACGTTTCA CCTGGTCATA TCGCTCAACG    350

TCTCGAAGCA CTGGCATGGG TTCTTCCAGA AGGGAACCAA CTGGGCCGAT    400

GGCCCCGCCT TTGTCACCCA ATGTCCTATC ACATCAGGAA ACGCCTTCCT    450
```

-continued

```
GTATGATTTC AACGTTCCGG ACCAAGCTGG TACTTTCTGG TACCACAGCC    500
ATCTCTCTAC ACAGTATTGT GACGGTCTTC GTGGTGCCTT TGTCGTCTAT    550
GATCCTAATG ATCCCAACAA GCAACTCTAT GATGTTGATA ACGGCAAGTT    600
CCTTGCATAT TTCATTTCTA TCATATCCTC ACCTGTATTG GCACAGAAAG    650
CACCGTGATT ACCTTGGCTG ATTGGTATCA TGCCCTTGCT CAGACTGTCA    700
CTGGTGTCGC GTGAGTGACA AATGGCCCTC AATTGTTCAC ATATTTTCCT    750
GATTATCATA TGATAGAGTA TCTGATGCAA CGTTGATCAA CGGATTGGGA    800
CGTTCGGCCA CCGGCCCCGC AAATGCCCCT CTGGCGGTCA TCAGTGTCGA    850
GCGGAATAAG AGGTCAGTTC CATAATTATG ATTATTTCCC GCGTTACTTC    900
CTAACAATTA TTTTTGTATC CCTCCACAGA TATCGTTTCC GATTGGTTTC    950
TATTTCTTGC GACCCTAACT TTATTTTCTC AATTGACCAC CACCCAATGA   1000
CCGTAATTGA GATGGACGGT GTTAATACCC AATCTATGAC CGTAGATTCG   1050
ATCCAAATAT TCGCAGGTCA ACGATATTCA TTTGTCGTAG GTTATTATAA   1100
ACTGCCCACC GATCATCTCT CACGTAACTG TTATAGATGC AAGCCAACCA   1150
ACCAGTTGGA AATTATTGGA TCCGCGCTAA ACCTAATGTT GGGAACACAA   1200
CTTTCCTTGG AGGCCTGAAC TCCGCTATAT TACGATATGT GGGAGCCCCT   1250
GACCAAGAAC CGACCACTGA CCAAACACCC AACTCTACAC CGCTCGTTGA   1300
GGCGAACCTA CGACCCCTCG TCTATACTCC TGTGGTATGT TGTTCTCGTT   1350
ACATATACCA AACCTAATAT GAAGACTGAA CGGATCTACT AGCCGGGACA   1400
GCCATTCCCT GGCGGTGCTG ATATCGTCAA GAACTTAGCT TTGGGTTTCG   1450
TACGTGTATT TCACTTCCCT TTTGGCAGTA ACTGAGGTGG AATGTATATA   1500
GAATGCCGGG CGTTTCACAA TCAATGGAGC GTCCCTCACA CCTCCTACAG   1550
TCCCTGTACT ACTCCAGATC CTCAGTGGTA CTCACAATGC ACAGGATCTT   1600
CTCCCAGCAG GAAGCGTGAT CGAACTTGAA CAGAATAAAG TTGTCGAAAT   1650
CGTTTTGCCC GCTGCGGGCG CCGTTGGCGG TCCTCATCCT TTTCACTTAC   1700
ATGGTGTAAG TATCAGACGT CCTCATGCCC ATATTGCTCC GAACCTTACA   1750
CACCTGATTT CAGCACAATT TCTGGGTGGT TCGTAGCGCC GGTCAAACCA   1800
CATACAATTT CAATGATGCT CCTATCCGTG ATGTTGTCAG TATTGGCGGT   1850
GCAAACGATC AAGTCACGAT CCGATTTGTG GTATGTATCT CGTGCCTTGC   1900
ATTCATTCCA CGAGTAATGA TCCTTACACT TCGGGTTCTC AGACCGATAA   1950
CCCTGGCCCA TGGTTCCTTC ACTGTCACAT TGACTGGCAT TTGGAGGCTG   2000
GGTTCGCTGT AGTCTTTGCG GAGGGAATCA ATGGTACTGC AGCTGCTAAT   2050
CCAGTCCCAG GTAAGACTCT CGCTGCTTTG CGTAATATCT ATGAATTTAA   2100
ATCATATCAA TTTGCAGCGG CTTGGAATCA ATTGTGCCCA TTGTATGATG   2150
CCTTGAGCCC AGGTGATACA TGA                                2173
``` encoding the enzyme laccase B1, having the translated protein sequence (SEQ ID No. 6)
```
MSLLRSLTSL IVLVIGAFAA IGPVTDLHIV NQNLDPDGFN RPTVLAGGTF    50
PGPLIRGNKG DNFKINVIDD LTEHSMLKAT SIHWHGFFQK GTNWADGPAF   100
VTQCPITSGN AFLYDFNVPD QAGTFWYHSH LSTQYCDGLR GAFVVYDPND   150
PNKQLYDVDN GNTVITLADW YHALAQTVTG VAVSDATLIN GLGRSATGPA   200
```

```
NAPLAVISVE RNKRYRFRLV SISCDPNFIF SIDHHPMTVI EMDGVNTQSM    250

TVDSIQIFAG QRYSFVMQAN QPVGNYWIRA KPNVGNTTFL GGLNSAILRY    300

VGAPDQEPTT DQTPNSTPLV EANLRPLVYT PVPGQPFPGG ADIVKNLALG    350

FNAGRFTING ASLTPPTVPV LLQ1LSGTHN AQDLLPAGSV IELEQNKVVE    400

IVLPAAGAVG GPHPFHLHGH NFWVVRSAGQ TTYNFNDAPI RDVVSIGGAN    450

DQVTIRFVTD NPGPWFLHCH IDWHLEAGFA VVFAEGINGT AAANPVPAAW    500

NQLCPLYDAL SPGDT                                         515
```

D. Cerrena laccase B2 gene from CBS154.29 strain (SEQ ID No. 7)
```
CACCGCGATG TCTCTTCTTC GTAGCTTGAC CTCCCTCATC GTACTAGCCA     50

CTGGTGCATT TGCTGCAATC GGTCCAGTCA CCGACCTACA TATAGTGAAC    100

CAGAATCTCG CCCCAGATGG TTTAAACCGC CCCACTGTAC TCGCAGGTGG    150

TACTTTCCCC GGTCCTCTGA TTCGTGGTAA CAAGGTACGC TTCATAACCG    200

CCCTCCGTAG ACGTAGGCTT CGGCTGACAT GACCATCATC TGTAGGGAGA    250

TAACTTTAAA ATTAATGTGA TTGACGACTT GACAGAACAC AGTATGCTCA    300

AGGCTACGTC CATTGTAAGT CCCTGATTAA CGTTTCACCT GGTCATATCG    350

CTCAACGTCT CGAAGCACTG GCATGGGTTC TTCCAGAAGG GAACCAACTG    400

GGCCGATGGC CCCGCCTTTG TCACCCAATG TCCTATCACA TCAGGAAACG    450

CCTTCTTGTA TGATTTCAAC GTTCCGGACC AAGCTGGTAC TTTCTGGTAC    500

CACAGCCATC TCTCYACACA GTATTGTGAC GGTCTTCGTG GTGCCTTTGT    550

CGTCTATGAT CCTAATGATC CCAACAAGCA ACTCTATGAT GTTGATAACG    600

GCAAGTCCCT TGCATATTTC AGTTCTATCA TATCCTCACC TGTATTGGCA    650

CAGAAAGCAC CGTGATTACC TTGGCTGATT GGTATCATGC CCTTGCTCAG    700

ACTGTCACTG GTGTCGCGTG AGTGACAAAT GGCCCTTAAT TGTTCACATA    750

TTTTCCTGAT TATCATATGA TAGAGTATCT GATGCAACGT TGATCAACGG    800

ATTGGGACGT TCGGCCACCG GCCCCGCAAA TGCCCCTCTG GCGGTCATCA    850

GTGTCGAGCG GAATAAGAGG TCAGTTCCAT AATTATGATT ATTTCCCGCG    900

TTACTTCCTA ACGATTATTT TTGTATCCCT CCACAGATAT CGTTTCCGAT    950

TGGTTTCTAT TTCTTGCGAC CCTAACTTTA TTTTCTCAAT TGACCACCAC   1000

CCAATGACCG TAATTGAGAT GGACGGTGTT AATACCCAAT CTATGACCGT   1050

AGATTCGATC CAAATATTCG CAGGTCAACG ATATTCATTT GTCGTAGGTT   1100

ATTATAAACT GCCCACCGAT CATCTCTCAC GTAACTGTTA TAGATGCAAG   1150

CCAACCAACC AGTTGGAAAT TATTGGATCC GYGCTAAACC TAATGTTGGG   1200

AACACAACTT TCCTTGGAGG CCTGAACTCC GCTATATTAC GATATGTGGG   1250

AGCCCCTGAC CAAGAACCGA CCACTGACCA AACACCCAAC TCTACACCGC   1300

TCGTCGAGGC GAACCTACGT CCCCTCGTCT ATACTCCTGT GGTATGTTGT   1350

TCTCGTTACA TATACCAAAC CTAATATGAG GACTGAACGG ATCTACTAGC   1400

CGGGACAGCC ATTCCCTGGC GGTGCTGATA TCGTCAAGAA CTTAGCTTTG   1450

GGTTTCGTAC GTGTATTTCA CTTCCCTTTT GGCAGTAACT GAGGTGGAAT   1500

GTATATAGAA TGCCGGGCGT TTCACAATCA ATGGAACATC CTTCACACCT   1550

CCTACAGTCC CTGTACTACT CCAGATCCTC AGTGGTACTC ACAATGCACA   1600

GGATCTTCTT CCAGCAGGAA GCGTGATCGA ACTTGAACAG AATAAAGTTG   1650
```

```
TCGAAATCGT TCTGCCCGCT GCGGGCGCCG TTGGCGGTCC TCATCCTTTC    1700
CACTTACATG GTGTAAGTAT CAGACGTCCT CATGCCTATA TTGCTCCGAA    1750
CCTTACACAC CTGATTTCAG CACAATTTCT GGGTGGTTCG TAGCGCCGGT    1800
CAAACCACAT ACAATTTCAA TGATGCTCCT ATCCGTGATG TTGTCAGTAT    1850
TGGCGGTGCA AACGATCAAG TCACGATCCG ATTTGTGGTA TGTATCTCGT    1900
GCCTTGCATT CATTCCACGA GTAATGATCC TTACACTTCG GGTTCTCAGA    1950
CCGATAACCC TGGCCCATGG TTCCTTCACT GTCACATTGA CTGGCATTTG    2000
GAGGCTGGGT TCGCTGTAGT CTTTGCGGAG GAATCAATG GCACTGCAGC      2050
TGCTAATCCA GTCCCAGGTA AGACTCTCGC TGCTTTGCGT AATATCTATG    2100
AATTTAAAGC ATATCAATTT GCAGCGGCTT GGAATCAATT GTGCCCGTTG    2150
TATGATGCCT TGAGCCCAGG tGATACATGA TTACTCGTAG CTGTGCTTTC    2200
TTATACATAT TCTATGGGTA TATCGGAGTA GCTGTACTAT AGTATGTACT    2250
ATACTAGGTG GGATATGYTG ATGTTGATTT ATATAATTTT GTTTGAAGAG    2300
TGACTTTATC GACTTGGGAT TTAGCCGAGT ACATACTGAT CTCTCACTAC    2350
AGGCTTGTTT TGTCTTTGGG CGCTTACTCA ACAGTTGACT GTTTTTGCTA    2400
TTACGCATTG AACCGCATTC CGGTCYGACT CGTGTCCTCT ACTGTGACTT    2450
GTATTGGCAT TCTAGCACAT ATGTCTCTTA CCTATAGGAA CAATATGTCT    2500
CAACACTGTT CCAAAACCTG CGTAAACCAA ATATCGTCCA TCAGATCAGA    2550
TCATTAACAG TGCCGCACTA ACCTAATACA CTGGCARGGA CTGTGGAAAT    2600
CCCTATAAAT GACCTCTAGA CCGTGAGGTC ATTGCAAGGT CGCTCTCCTT    2650
GTCAAGATGA CCC                                             2663
encoding the enzyme laccase B2, having the translated protein
sequence
                                                (SEQ ID No. 8)
MSLLRSLTSL IVLATGAFAA IGPVTDLHIV NQNLAPDGLN RPTVLAGGTF     50

PGPLIRGNKG DNFKINVIDD LTEHSMLKAT SIHWHGFFQK GTNWADGPAF    100

VTQCPITSGN AFLYDFNVPD QAGTFWYHSH LSTQYCDGLR GAFVVYDPND   150

PNKQLYDVDN GNTVITLADW YHALAQTVTG VAVSDATLIN GLGRSATGPA    200

NAPLAVISVE RNKRYRFRLV SISCDPNFIF SIDHHPMTVI EMDGVNTQSM    250

TVDSIQIFAG QRYSFVMQAN QPVGNYWIRA KPNVGNTTFL GGLNSAILRY    300

VGAPDQEPTT DQTPNSTPLV EANLRPLVYT PVPGQPFPGG ADIVKNLALG    350

FNAGRFTING TSFTPPTVPV LLQILSGTHN AQDLLPAGSV IELEQNKVVE    400

IVLPAAGAVG GPHPFHLHGH NFWVVRSAGQ TTYNFNDAPI RDVVSIGGAN   450

DQVTIRFVTD NPGPWFLHCH IDWHLEAGFA VVFAEGINGT AAANPVPAAW    500

NQLCPLYDAL SPGDT                                          515
E. Cerrena laccase B3 gene (partial) from ATCC20013 strain
                                                (SEQ ID No. 9)
GTGGGGCGG ATCCCTAACT GTTTCGAATC GGCACCGAAG TATGCAGGTG      50

TGACGGAGAT GAGGCGTTTT TTCATCTTCC ACTGCAGTAT AAAATGTCTC    100

AGGTAACGTC CAGCTTTTTG TACCAGAGCT ACCTCCAAAT ACCTTTACTC    150

GCAAAGGTTT CGCGATGTCT CTTCTTCGTA GCTTGACCTC CCTCATCGTA    200

CTAGCCACTG GTGCATTTGC TGCAATCGGT CCAGTCACTG ACCTACATAT    250

AGTGAACCAG AATCTCGCCC CAGATGGTTT CAACCGCCCC ACTGTACTCG    300
```

-continued

```
CAGGTGGTAC TTTCCCCGGT CCTCTGATTC GTGGTAACAA GGTACGCTTC    350
ATAACCGCCC TCCGTAGACG TAGGCTTCGG CTGACATGAC CATCATCTGT    400
AGGGAGATAA CTTTAAAATT AATGTGATTG ACGACTTGAC AGAACACAGT    450
ATGCTCAAGG CCACGTCCAT TGTAAGTCCC TGATTAACGT TTCACCTGGT    500
CATATCGCTC AACGTCTCGA AGCACTGGCA TGGGTTCTTC CAGAAGGGAA    550
CCAACTGGGC CGATGGCCCC GCCTTTGTCA CCCAATGTCC TATCACATCA    600
GGAAACTCCT TCCTGTATGA TTTCAACGTT CCGGACCAAG CTGGTACTTT    650
CTGGTACCAC AGCCATCTCT CTACACAGTA TTGTGACGGT CTTCGTGGTG    700
CCTTTGTCGT CTATGATCCT AATGATCCCA ACAAGCAACT CTATGATGTT    750
GATAACGGCA AGTCCCTTGC ATATTTCATT TCTATCATAT CCTCACCTGT    800
ATTGGCACAG AAAGCACCGT GATTACCTTG GCTGATTGGT ATCATGCCCT    850
TGCTCAGACT GTCACTGGTG TCGCGTGAGT GACAAATGGC CCTCAATTGT    900
TCACATATTT TCCTGATTAT CATATGATAG AGTATCTGAT GCAACGTTGA    950
TCAACGGATT GGGACGTTCG GCCACCGGCC CCGCAAATGC CCCTCTGGCG   1000
GTCATCAGTG TCGAGCGGAA TAAGAGGTCA GTTCCATAAT TATGATTATT   1050
TCCCGCGTTA CTTCCTAACA ATTATTCTTG TATCCCTCCA CAGATATCGC   1100
TTCCGATTGG TGTCTATTTC TTGCGACCCT AACTTTATTT TCTCAATTGA   1150
TCACCACCCA ATGACCGTAA TTGAGATGGA CGGTGTTAAT ACCCAATCTA   1200
TGACCGTAGA TTCGATCCAA ATATTCGCAG GTCAACGATA TTCATTTGTC   1250
GTAGGTTATT ATAAACTGCC CACCGATCAT CTCTCACGTA ACTGTTATAG   1300
ATGCAAGCCA ACCAACCRGT TGGAAATTAT TGGATCC                 1337
``` encoding the enzyme laccase B3, having the partial translated protein sequence (SEQ ID No. 10)
```
MSLLRSLTSL IVLATGAFAA IGPVTDLHIV NQNLAPDGFN RPTVLAGGTF     50
PGPLIRGNKG DNFKINVIDD LTEHSMLKAT SIHWHGFFQK GTNWADGPAF    100
VTQCPITSGN SFLYDFNVPD QAGTFWYHSH LSTQYCDGLR GAFVVYDPND   150
PNKQLYDVDN GKTVITLADW YHALAQTVTG VAVSDATLIN GLGRSATGPA   200
NAPLAVISVE RNKRYRFRLV SISCDPNFIF SIDHHPMTVI EMDGVNTQSM   250
TVDSIQIFAG QRYSFVMQAN QPVGNYWI                           278
```

F. Cerrena laccase C gene (partial) from CBS154.29 strain (SEQ ID No. 11)
```
TGCAATCGGA CCGGTBGCTG ACCTTCACAT TACGGACGAT ACCATTGCCC     50
CCGATGGTTT CTCTCGTCCT GCTGTTCTCG CTGGCGGGGG TTTCCCTGGC    100
CCTCTCATCA CCGGAAACAA GGTAATGCCT AATGGTTGCG TCTTTGTTGG    150
TGCTCTCATT CATCCACGAC ATTTTGTACC AGGGCGACGC CTTTAAACTC    200
AATGTCATCG ATGAACTAAC GGACGCATCC ATGCTGAAGY CGACTTCCAT    250
CGTAAGTCTC GCTGTATTGC TCCTTGAGCC ATTTCATTGA CTATAACTAC    300
AACCAGCACT GGCATGGATT CTTCCAAAAG GGTACTAATT GGGCAGATGG    350
TCCCGCTTTT GTGAACCAAT GCCCCATCAC CACGGGAAAC TCCTTCTTGT    400
ACGACTTCCA GGTTCCTGAT CAAGCTGGTA AGCATGAGAT TACACTAGGA    450
AAGTTTAATT TAATAACTAT TCAATCAGGA ACCTACTGGT ATCATAGTCA    500
TTTGTCTACG CAATACTGTG ATGGTCTCAG AGGTGCATTC GTTGTCTACG    550
```

-continued

```
ACCCTTCAGA TCCTCACAAG GATCTCTACG ACGTCGACGA CGGTGAGCTT    600

TGCTTTTTTC ATTGGTATCC ATTATCGCTC ACGTGTCATT ACTGCGCCAC    650

AGAAAGTACC GTCATCACTT TGGCTGATTG GTATCATACT TTGGCTCGTC    700

AGATTGTTGG CGTTGCGTGA GTAGTCTTGT ACCGACTGAA ACATATTCCA    750

GTTGCTGACT TCCCCACAGC ATTTCTGATA CTACCTTGAT AAACGGTTTG    800

GGCCGCAATA CCAATGGTCC GGCTGATGCT GCTCTTGCTG TGATCAATGT    850

TGACGCTGGC AAACGGTGTG TCCAGATTAC TATACTCCCC ATGACGTCTC    900

AATGCTGATG TGTACTACTT CCAGGTACCG TTTCCGTCTT GTTTCCATAT    950

CCTGTGACCC CAATTGGGTA TTCTCGATTG ACAACCATGA CTTTACGGTC   1000

ATTGAAGTCG ATGGTGTTAA CAGTCAACCT CTCAACGTCG ATTCTGTTCA   1050

GATCTTCGCC GGACAACGTT ACTCGTTCGT                         1080
``` encoding the enzyme laccase C, having the partial translated protein sequence

```
                                            (SEQ ID No. 12)
AIGPVADLHI TDDTIAPDGF SRPAVLAGGG FPGPLITGNK GDAFKLNVID     50

ELTDASMLKX TSIHWHGFFQ KGTNWADGPA FVNQCPITTG NSFLYDFQVP    100

DQAGTYWYHS HLSTQYCDGL RGAFVVYDPS DPHKDLYDVD DESTVITLAD    150

WYHTLARQIV GVAISDTTLI NGLGRNTNGP ADAALAVINV DAGKRYRFRL    200

VSISCDPNWV FSIDNHDFTV IEVDGVNSQP LNVDSVQIFA GQRYSF       246
```

G. *Cerrena* laccase D1 gene from CBS154.29 strain

```
                                            (SEQ ID No. 13)
GATTCTAATA GACCAGGCAT ACCAAGAGAT CTACAGGTTG ACAGACCATT     50

CTTCTAGGCG GCATTTATGC TGTAGCGTCA GAAATTATCT CTCCATTTGT    100

ATCCCACAGG TCCTGTAATA ACACGGAGAC AGTCCAAACT GGGATGCCTT    150

TTTTCTCAAC TATGGGCGCA CATAGTCTGG ACGATGGTAT ATAAGACGAT    200

GGTATGAGAC CCATGAAGTC AGAACACTTT TGCTCTCTGA CATTTCATGG    250

TTCACACTCT CGAGATGGGA TTGAACTCGG CTATTACATC GCTTGCTATC    300

TTAGCTCTGT CAGTCGGAAG CTATGCTGCA ATTGGGCCCG TGGCCGACAT    350

ACACATTGTC AACAAAGACC TTGCTCCAGA TGGCGTACAA CGTCCAACCG    400

TGCTTGCCGG AGGCACTTTT CCTGGGACGT TGATCACCGG TCAGAAAGTA    450

AGGGATATTA GTTTGCGTCA AAGAGCCAAC CAAAACTAAC CGTCCCGTAC    500

TATAGGGTGA CAACTTCCAG CTCAATGTCA TCGATGATCT TACCGACGAT    550

CGGATGTTGA CGCCAACTTC CATTGTGAGC CTATTATTGT ATGATTTATC    600

CGAATAGTTT CGCAGTCTGA TCATTGGATC TCTATCGCTA GCATTGGCAC    650

GGTTTCTTCC AGAAGGGAAC CGCTTGGGCC GACGGTCCCG CCTTCGTAAC    700

TCAGTGCCCT ATAATAGCAG ATAACTCTTT TCTGTATGAC TTCGACGTCC    750

CAGACCAAGC TGGTACTTTC TGGTATCATA GTCATCTATC CACTCAGTAC    800

TGTGACGGTT TACGTGGTGC CTTCGTTGTG TACGATCCTA ACGATCCTCA    850

CAAAGACCTA TACGATGTTG ATGACGGTGG GTTCCAAATA TTTGTTCTGC    900

AGACATTGTA TTGACGGTGT TCATTATAAT TTCAGAGAGC ACCGTGATTA    950

CCCTTGCGGA TTGGTACCAT GTTCTCGCCC AGACCGTTGT CGGCGCTGCG   1000

TGAGTAACAC ATACACGCGC TCCGGCACAC TGATACTAAT TTTTTTTTAT   1050

TGTAGCACTC CTGATTCTAC CTTGATCAAC GGGTTAGGCC GTTCACAGAC   1100
```

-continued

```
CGGACCCGCT GATGCTGAGC TGGCTGTTAT CAGCGTTGAA CATAACAAAC      1150

GGTATGTCAT CTCTACCCAG TATCTTCTCT CCTGCTCTAA TTCGCTGTTT      1200

CACCATAGAT ACCGTTTCCG TTTGGTTTCG ATTTCGTGCG ACCCCAACTT      1250

TACCTTCTCC GTTGATGGTC ATAATATGAC TGTCATCGAA GTCGATGGTG      1300

TCAACACACG ACCCCTGACC GTTGACTCTA TTCAAATCTT CGCCGGACAG      1350

AGGTATTCCT TTGTCGTAAG TTAATCGATA TATTCTCCTT ATTACCCCTG      1400

TGTAATTGAT GTCAATAGCT CAATGCTAAC CAACCCGAAG ACAATTACTG      1450

GATCCGTGCT ATGCCAAACA TCGGTAGAAA TACAACAACA CTGGACGGAA      1500

AGAATGCCGC TATCCTTCGA TACAAGAATG CTTCTGTAGA AGAGCCCAAG      1550

ACCGTTGGGG GCCCCGCTCA ATCCCCGTTG AATGAAGCGG ACCTGCGTCC      1600

ACTCGTACCT GCTCCTGTGG TATGTCTTGT CGCGCTGTTC CATCGCTATT      1650

TCATATTAAC GTTTTGTTTT TGTCAAGCCT GGAAACGCTG TTCCAGGTGG      1700

CGCAGACATC AATCACAGGC TTAACTTAAC TTTCGTACGT ACACCTGGTT      1750

GAAACATTAT ATTTCCAGTC TAACCTCTCT TGTAGAGTAA CGGCCTCTTC      1800

AGCATCAACA ACGCCTCCTT CACTaATCCT TCGGTCCCCG CCTTATTACA      1850

AATTCTGAGC GGTGCTCAGA ACGCTCAAGA TTTACTTCCA ACGGGTAGTT      1900

ACATTGGCCT TGAACTAGGC AAGGTTGTGG AGCTCGTTAT ACCTCCTCTG      1950

GCAGTTGGAG GACCGCACCC TTTCCATCTT CATGGCGTAA GCATACCACA      2000

CTCCCGCAGC CAGAATGACG CAAACTAATC ATGATATGCA GCACAATTTC      2050

TGGGTCGTCC GTAGTGCAGG TAGCGATGAG TATAACTTTG ACGATGCTAT      2100

CCTCAGGGAC GTCGTRAGCA TTGGAGCGGG GACTGATGAA GTCACAATCC      2150

GTTTCGTGGT ATGTCTCACC CCTCGCATTT TGAGACGCAA GAGCTGATAT      2200

ATTTTAACAT AGACCGACAA TCCGGGCCCG TGGTTCCTCC ATTGCCATAT      2250

TGATTGGCAT TTGGAGGCAG GCCTTGCCAT CGTCTTCGCT GAGGGCATCA      2300

ATCAGACCGC TGCAGCCAAC CCAACACCCC GTACGTGACA CTGAGGGTTT      2350

CTTTATAGTG CTGGATTACT GAATCGAGAT TTCTCCACAG AAGCATGGGA      2400

TGAGCTTTGC CCCAAATATA ACGGGTTGAG TGCGAGCCAA AAGGTCAAGC      2450

CTACGAACAG AACTGCTATT TAAACGTGGT CCTAGACTAC GGGCATATAA      2500

GTATTCGGGT AGCGCGTGTG AGCAATGTTC CGATACACGT AGATTCATCA      2550

CCGGACACGC TGGGACAATT TGTGTATAAT GGCTAGTAAC GTATCTGAGT      2600

TCTGGTGTGT AGTTCAAAGA GACAGCCCTT CCTGAGACAG CCCTTCCTGA      2650

GACAGCCCTT CCTGAGACGT GACCTCCGTA GTCTGCACAC GATACTYCTA      2700

AATACGTATG GCAAGATGAC AAAGAGGAGG ATGTGAGTTA CTACGAACAG      2750

AAATAGTGCC CGGCCTCGGA GAGATGTTCT TGAATATGGG ACTGGGACCA      2800

ACATCCGGA                                                  2809
``` encoding the enzyme laccase D1, having the translated protein sequence (SEQ ID No. 14)

```
MGLNSAITSL AILALSVGSY AAIGPVADIH IVNKDLAPDG VQRPTVLAGG       50

TFPGTLITGQ KGDNFQLNVI DDLTDDRMLT PTSIHWHGFF QKGTAWADGP      100

AFVTQCPIIA DNSFLYDFDV PDQAGTFWYH SHLSTQYCDG LRGAFVVYDP     150

NDPHKDLYDV DDGGTVITLA DWYHVLAQTV VGAATPDSTL INGLGRSQTG     200
```

```
PADAELAVIS  VEHNKRYRFR  LVSISCDPNF  TFSVDGHNMT  VIEVDGVNTR   250
PLTVDSIQIF  AGQRYSFVLN  ANQPEDNYWI  RAMPNIGRNT  TTLDGKNAAI   300
LRYKNASVEE  PKTVGGPAQS  PLNEADLRPL  VPAPVPGNAV  PGGADINHRL   350
NLTFSNGLFS  INNASFTNPS  VPALLQILSG  AQNAQDLLPT  GSYIGLELGK   400
VVELVIPPLA  VGGPHPFHLH  GHNFWVVRSA  GSDEYNFDDA  ILRDVVSIGA   450
GTDEVTIRFV  TDNPGPWFLH  CHIDWHLEAG  LAIVFAEGIN  QTAAANPTPQ   500
AWDELCPKYN  GLSASQKVKP  KKGTAI                               526
```

H. *Cerrena* laccase D2 gene from CBS115.075 strain
(SEQ ID No. 15)

```
GATCTGGACG ATGGTATATA AGACGATGGT ATGAGACCCA TGAAGTCTGA   50
ACACTTTTGC TCTCTGACAT TCATGGTTC ATACTCTCGA GATGGGATTG    100
AACTCGGCTA TTACATCGCT TGCTATCTTA GCTCTGTCAG TCGGAAGCTA   150
TGCTGCAATT GGGCCCGTGG CCGACATACA CATTGTCAAC AAAGACCTTG   200
CTCCAGATGG TGTACAACGT CCAACCGTGC TCGCCGGAGG CACTTTTCCT   250
GGGACGTTGA TCACCGGTCA GAAAGTAAGG AATATTAGTT TGCGTCAAAG   300
AGCCAACCAA AATTAACCGT CCCGTCCCAT AGGGTGACAA CTTCCAGCTC   350
AATGTCATTG ATGATCTTAC CGACGATCGG ATGTTGACAC CAACTTCCAT   400
TGTGAGCCTA TTATTGTATG ATTTATCCGT ATAGTTTCTC AGTCTGATCA   450
TTGGCTCTCT ATCGCTAGCA TTGGCACGGT TCCTTCCAGA AGGGAACCGC   500
TTGGGCCGAC GGTCCCGCCT TCGTAACTCA GTGCCCTATA ATAGCAGATA   550
ACTCTTTTCT GTATGACTTC GACGTCCCCG ACCAAGCTGG TACTTTCTGG   600
TATCATAGTC ATCTATCCAC TCAGTACTGT GACGGTTTAC GTGGTGCCTT   650
CGTTGTGTAC GATCCTAACG ATCCTCACAA AGACCTATAC GATGTTGATG   700
ACGGTGGGTT CCAAATACTT GACCAAGAAA CATTATATTG ATAGTATCCA   750
CTCTGATTTT CAGAGAGCAC CGTGATTACC CTTGCGGATT GGTACCATGT   800
TCTCGCCCAG ACCGTTGTCG GCGCTGCGTG AGTAACACAT ACACGCGCTC   850
CGGCACACTG ATACTAATTT TTTATTGTAG CACTCCTGAT TCTACCTTGA   900
TCAACGGGTT AGGCCGTTCA CAGACCGGAC CCGCTGATGC TGAGCTGGCT   950
GTTATCAGCG TTGAACATAA CAAACGGTAT GTCATCTCTA CCCATTATCT   1000
TCTCTCCTGC TTTAATTCGC TGTTTCACCA TAGATACCGA TTCCGTTTGG   1050
TTTCGATTTC GTGCGACCCC AACTTTACCT TCTCCGTTGA TGGTCATAAT   1100
ATGACTGTCA TCGAAGTCGA CGGTGTCAAC ACACGACCCC TGACCGTTGA   1150
CTCTATTCAA ATCTTCGCCG GACAGAGGTA TTCCTTTGTC GTAAGTTAAT   1200
CGATATATTC TCCCTATTAC CCCTGTGTAA TTGATGTCAA CAGCTCAATG   1250
CTAACCAACC CGACGACAAT TACTGGATCC GTGCTATGCC AAACATCGGT   1300
AGAAATACAA CAACACTGGA CGGAAAGAAT GCCGCTATCC TTCGATACAA   1350
GAATGCTTCT GTAGAAGAGC CCAAGACCGT TGGGGGCCCC GCTCAATCCC   1400
CGTTGAATGA AGCGGACCTG CGTCCACTCG TACCTGCTCC TGTGGTATGT   1450
CTTGTCGTGC TGTTCCATCG CTATTTCATA TTAACGTTTT GTTTTTGTCA   1500
AGCCTGGAAA CGCTGTTCCA GGTGGCGCAG ACATCAATCA CAGGCTTAAC   1550
TTAACTTTCG TACGTACACC TGGTTGAAAC ATTATATTTC CAGTCTAACC   1600
```

-continued

```
TCTTGTAGAG TAACGGCCTT TTCAGCATCA ACAACGCCTC CTTCACTAAT    1650

CCTTCGGTCC CCGCCTTATT ACAAATTCTG AGCGGTGCTC AGAACGCTCA    1700

AGATTTACTT CCAACGGGTA GTTACATTGG CCTTGAACTA GGCAAGGTTG    1750

TGGAGCTCGT TATACCTCCT CTGGCAGTTG GAGGACCGCA CCCTTTCCAT    1800

CTTCATGGCG TAAGCATACC ACACTCCCGC AGCCAGAATG ACGCAAACTA    1850

ATCATGATAT GCAGCACAAT TTCTGGGTCG TCCGTAGTGC AGGTAGCGAT    1900

GAGTATAACT TTGACGATGC TATCCTCAGG GACGTCGTGA GCATTGGAGC    1950

GGGGACTGAT GAAGTCACAA TCCGTTTCGT GGTATGTCTC ACCCCTCGCA    2000

TTTTGAGACG CAAGAGCTGA TATATTTTAA CATAGACCGA CAATCCGGGC    2050

CCGTGGTTCC TCCATTGCCA TATTGATTGG CATTTGGAGG CAGGCCTTGC    2100

CATCGTCTTC GCTGAGGGCA TCAATCAGAC CGCTGCAGCC AACCCAACAC    2150

CCCGTACGTG ACACTGAGGG TTTCTTTATA GTGCTGGATT ACTGAATCGA    2200

GATTTCTCCA CAGAAGCATG GGATGAGCTT TGCCCCAAAT ATAACGGGTT    2250

GAGTGCGAGC CAGAAGGTCA AGCCTAAGAA AGGAACTGCT ATTTAAACG     2299
``` encoding the enzyme laccase D2, having the translated protein sequence (SEQ ID No. 16)
```
MGLNSAITSL AILALSVGSY AATGPVADIH IVNKDLAPDG VQRPTVLAGG     50

TFPGTLITGQ KGDNFQLNVI DDLTDDRMLT PTSIHWHGFF QKGTAWADGP    100

AFVTQCPIIA DNSFLYDFDV PDQAGTFWYH SHLSTQYCDG LRGAFVVYDP    150

NDPHKDLYDV DDGGTVITLA DWYHVLAQTV VGAATPDSTL INGLGRSQTG    200

PADAELAVIS VEHNKRYRFR LVSISCDPNF TFSVDGHNMT VIEVDGVNTR    250

PLTVDSIQIF AGQRYSFVLN ANQPDDNYWI RAMPNIGRNT TTLDGKNAAI    300

LRYKNASVEE PKTVGGPAQS PLNEADLRPL VPAPVPGNAV PGGADINHRL    350

NLTFSNGLFS INNASFTNPS VPALLQILSG AQNAQDLLPT GSYIGLELGK    400

VVELVIPPLA VGGPHPFHLH GHNFWVVRSA GSDEYNFDDA ILRDVVSIGA    450

GTDEVTIRFV TDNPGPWFLH CHIDWHLEAG LAIVFAEGIN QTAAANPTPQ    500

AWDELCPKYN GLSASQKVKP KKGTAI                             526
```

I. Cerrena laccase E gene (partial) from CBS154.29 strain (SEQ ID No. 17)
```
TGCAATCGGA CCGGTGGCCG ACCTCAAGAT CGTAAACCGA GACATTGCAC     50

CTGACGGTTT TATTCGTCCC GCCGTTCTCG CTGGAGGGTC GTTCCCTGGT    100

CCTCTCATTA CAGGGCAGAA AGTACGTTAC GCTATCTCGG TGCTTTGGCT    150

TAATTAAACT ATTTGACTTT GTGTTCTCTT AGGGGAACGA GTTCAAAATC    200

AATGTAGTCA ATCAACTGAC CGATGGTTCT ATGTTAAAAT CCACCTCAAT    250

CGTAAGCAGA ATGAGCCCTT TGCATCTCGT TTTATTGTTA ATGCGCCCAC    300

TATAGCATTG GCATGGATTC TTCCAGAAGG GAACAAACTG GGCAGACGGT    350

CCTGCGTTCG TGAACCAATG TCCAATCGCC ACGAACAATT CGTTCTTGTA    400

TCAGTTTACC TCACAGGAAC AGCCAGGTGA GTATGAGATG GAGTTCATCC    450

GAGCATGAAC TGATTTATTT GGAACCTAGG CACATTTTGG TACCATAGTC    500

ATCTTTCCAC ACAATACTGC GATGGTTTGC GAGGGCCACT CGTGGTGTAT    550

GACCCACAAG ACCCGCATGC TGTTCTCTAC GACGTCGACG ATGGTTCGTA    600

CTTCGCATAT CCACGCTCGC TTTCATACAA TGTAAACTTT GTTCCTCCAG    650
```

```
                                               -continued
AAAGTACAAT CATCACGCTC GCGGATTGGT ATCATACCTT GGCTCGGCAA     700

GTGAAAGGCC CAGCGTAAGG CACTTTAGTG TTTCCTCATA GTCCAAGAAA     750

TTCTAACACG CCTTCTTCAT CAGGGTTCCT GGTACGACCT TGATCAACGG     800

GTTGGGGCGT CACAACAATG GTCCTCTAGA TGCTGAACTA GCGGTGATCA     850

GTGTTCAAGC CGGCAAACGG CAAGTTCAAT TCACACTTTT CACTCTGTAC     900

CTTCTTCCTG ACATTCTTTT CTTGTAGTTA CCGCTTCCGC CTGATTTCAA     950

TTTCATGCGA TCCCAACTAC GTATTCTCCA TTGATGGCCA TGATATGACT    1000

GTCATCGAAG TGGATAGTGT TAACAGTCAA CCTCTCAAGG TAGATTCTAT    1050

CCAAATATTT GCAGGTCAGA GATATTCGTT CGTGGTGAGT CAGATCAGGG    1100

CATATCCTTT TGTCGATACG TCATTGACCA TATAATGCTA CAAGCTGAAT    1150

GCCAACCAAC CAG                                            1163 encoding the enzyme laccase E, having the partial translated
protein sequence
                                                (SEQ ID No. 18)
AIGPVADLKI VNRDIAPDGF IRPAVLAGGS FPGPLITGQK GNEFKINVVN      50

QLTDGSMLKS TSIHWHGFFQ KGTNWADGPA FVNQCPIATN NSFLYQFTSQ     100

EQPGTFWYHS HLSTQYCDGL RGPLVVYDPQ DPHAVLYDVD DESTIITLAD     150

WYHTLARQVK GPAVPGTTLI NGLGRHNNGP LDAELAVISV QAGKRQVQFT     200

LFTLYRFRLI SISCDPNYVF SIDGHDMTVI EVDSVNSQPL KVDSIQIFAG     250

QRYSFVLNAN QP                                             262
```

The term "% identity" herein and refers to the level of nucleic acid or amino acid sequence identity between the nucleic acid sequence that encodes a laccase described herein or the laccase amino acid sequence, when aligned using a sequence alignment program.

For example, as used herein, 80% sequence identity is determined by an algorithm, and accordingly a homologue of a given sequence has greater than 80% sequence identity over a length of the given sequence. Exemplary levels of sequence identity include, but are not limited to, 80, 85, 90, 95, 98% or more sequence identity to a given sequence, e.g., the coding sequence for a laccase, as described herein.

Exemplary computer programs which can be used to determine identity between two sequences include, but are not limited to, the suite of BLAST programs, e.g., BLASTN, BLASTX, and TBLASTX, BLASTP and TBLASTN, publicly available on the Internet at www.ncbi.nlm.nih.gov/BLAST. See also, Altschul, et al., 1990 and Altschul, et al., 1997.

Sequence searches are typically carried out using the BLASTN program when evaluating a given nucleic acid sequence relative to nucleic acid sequences in the GenBank DNA Sequences and other public databases. The BLASTX program is preferred for searching nucleic acid sequences that have been translated in all reading frames against amino acid sequences in the GenBank Protein Sequences and other public databases. Both BLASTN and BLASTX are run using default parameters of an open gap penalty of 11.0, and an extended gap penalty of 1.0, and utilize the BLOSUM-62 matrix. (See, e.g., Altschul, et al., 1997.)

An alignment of selected sequences in order to determine "% identity" between two or more sequences, may be performed using, for example, the CLUSTAL-W program in MacVector version 6.5, operated with default parameters, including an open gap penalty of 10.0, an extended gap penalty of 0.1, and a BLOSUM 30 similarity matrix.

II. Mediators

In an embodiment, the enzymatic oxidation system further comprises one or more chemical mediator agents which enhance the activity of the laccase enzyme. The term "chemical mediator" (or "mediator" may be used interchangeably herein) is defined herein as a chemical compound which acts as a redox mediator to effectively shuttle electrons between the enzyme exhibiting oxidase activity and the dye. Chemical mediators are also known as enhancers and accelerators in the art.

The chemical mediator may be a phenolic compound, for example, methyl syringate, and related compounds, as described in WO 95/01426 and 96/12845. The chemical mediator may also be an N-hydroxy compound, an N-oxime compound, or an N-oxide compound, for example, N-hydroxybenzotriazole, violuric acid, or N-hydroxyacetanilide. The chemical mediator may also be a phenoxazine/phenothiazine compound, for example, phenothiazine-10-propionate. The chemical mediator may further be 2,2'-azinobis-(3-ethylbenzothiazoline-6-sulfonic acid) (ABTS). Other chemical mediators are well known in the art. For example, the compounds disclosed in WO 95/01426 are known to enhance the activity of a laccase. In particular embodiments, the mediator may be acetosyringone, methyl syringate, ethyl syringate, propyl syringate, butyl syringate, hexyl syringate, or octyl syringate.

Preferably, the mediator is 4-cyano-2,6-dimethoxyphenol, 4-carboxamido-2,6-dimethoxyphenol or an N-substituted derivative thereof such as, for example, 4-(N-methyl carboxamido)-2,6-dimethoxyphenol, 4-[N-(2-hydroxyethyl) carboxamido]-2,6-dimethoxyphenol, or 4-(N,N-dimethyl carboxamido)-2,6-dimethoxyphenol.

The mediator used in the present invention may be described by the following formula:

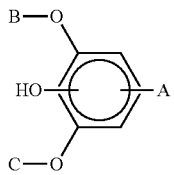

in which formula A is a group such as —R, -D, —CH=CH-D, —CH=CH—CH=CH-D, —CH=N-D, —N=N-D, or —N=CH-D, in which D is selected from the group consisting of —CO-E, —$SO_2$-E, —CN, —NXY, and —$N^+$XYZ, in which E may be —H, —OH, —R, —OR, or —NXY, and X and Y and Z may be identical or different and selected from —H, —OH, —OR and —R; R being a $C_1$-$C_{16}$ alkyl, preferably a $C_1$-$C_8$ alkyl, which alkyl may be saturated or unsaturated, branched or unbranched and optionally substituted with a carboxy, sulfo or amino group; and B and C may be the same or different and selected from $C_mH_{2m+1}$; 1≤m≤5.

In an embodiment A in the above mentioned formula is —CN or —CO-E, in which E may be —H, —OH, —R, —OR, or —NXY, where X and Y may be identical or different and selected from —H, —OH, —OR and —R, R being a $C_1$-$C_{16}$ alkyl, preferably a $C_1$-$C_8$ alkyl, which alkyl may be saturated or unsaturated, branched or unbranched and optionally substituted with a carboxy, sulfa or amino group; and B and C may be the same or different and selected from $C_mH_{2m+1}$; 1≤m≤5.

In the above mentioned formula A may be placed meta to the hydroxy group instead of being placed in the para-position as shown.

In particular embodiments, the mediator may be acetosyringone, methylsyringate, ethylsyringate, propylsyringate, butylsyringate, hexylsyringate, or octylsyringate. Preferably, the mediator is 4-cyano-2,6-dimethoxyphenol, 4-carboxamido-2,6-dimethoxyphenol or a N-substituted derivative thereof such as 4-(N-methyl carboxamido)-2,6-dimethoxyphenol, 4-[N-(2-hydroxyethyl) carboxamido]-2,6-dimethoxyphenol, or 4-(N,N-dimethyl carboxamido)-2,6-dimethoxyphenol.

The mediator of the invention may be present in concentrations of from 0.005-1000 mmole per g denim, preferably 0.05-500 μmole per g denim, more preferably 0.5-100 μmole per g denim.

The mediators may be prepared by methods known to the skilled artisan, such as those disclosed in WO 97/11217, WO 96/12845 and U.S. Pat. No. 5,752,980.

III. Utility

Industrial applications of laccases include bleaching of pulp and paper and textile bleaching, for example, of indigo-dyed denim fabrics. Laccases have also been found to be useful for hair dyeing (see, e.g., WO 95/33836 and WO 95/33837). European Patent No. 0504005 discloses that laccases can be used for dyeing wool.

The laccases described herein find use in the dyeing and bleaching of textiles, fibers, yarns and the like. The laccases also find use in the treatment of waste water, the delignification of pulp, the depolymerization of high molecular weight aggregates, deinking waste paper, the polymerization of aromatic compounds, radical mediated polymerization and cross-linking reactions (e.g., paints, coatings, biomaterials), and the activation of dyes and to couple organic compounds.

The laccases may be used in a cleaning composition or component thereof, or in a detergent.

As described herein, the laccases are capable of oxidizing a wide variety of colored compounds having different chemical structures, using oxygen as the electron acceptor. Accordingly, the laccases presented herein can be used in applications where it is desirable to modify the color associated with colored compounds, such as in cleaning, e.g., for removing the food stains on fabric. In certain situations, a mediator or enhancer can be used to obtain desirable effects.

The laccases presented herein can be used in the field of textiles. For example, the laccases described herein can be used in the treatment, processing, finishing, polishing, or production of fibers, or other fabrics or articles of manufacture. The enzymes herein can be useful, for example, in denim treatment (bleaching work-up processes); in de-coloring indigo waste; in fabric dyeing; in textile bleaching processes; in fiber modification; in achieving enhanced fiber or fabric properties; etc.

The laccases described herein can be used in the leather industry. For example, the laccases can be used in the processing of animal hides including but not limited to de-hairing, liming, bating and/or tanning of hides.

Also disclosed herein is a process for the removal of lignin from lignocellulose-containing material, the bleaching of lignocellulose-containing material (i.e. the enzymatic de-inking of recycled paper) and/or the treatment of waste water arising from the manufacture of paper or cellulose. The process uses laccase enzymes obtained from Cerrena sp., at the same time adding or metering in non-aromatic redox agents plus phenolic and/or non-phenolic aromatic redox compounds, the phenolic and non-phenolic units of the lignin either being oxidized directly by the action of these phenolic and/or non-phenolic aromatic compounds, or the lignin being oxidized by other phenolic and/or non-phenolic compounds produced by the oxidizing action of these compounds.

The laccases described herein can be used in the field of pulp and paper. For example, the laccases can be used in the manufacture of paper pulps and fluff pulps from raw materials such as wood, bamboo, and cereal rice straw; the manufacture of paper and boards for printing and writing, packaging, sanitary and other technical uses; recycling of cellulose fiber for the purpose of making paper and boards; and the treatment of waste products generated by and treated at pulp or paper mills and other facilities specifically dedicated to the manufacture of paper, pulp, or fluff. The enzymes presented herein can be useful, for example, in wood processing; in pulp bleaching; in wood fiber modification; in bio-glue (lignin activation) for MDF manufacturing; for enhanced paper properties; in ink removal; in paper dyeing; in adhesives (e.g. lignin based glue for particle- or fiber boards); etc.

The laccases described herein can be used in the field of feed. For example, the laccases presented herein can be used as a feed additive alone or as part of a feed additive with the aim to increase the nutritional value of feed for any kind of animals such as chicken, cows, pigs, fish and pets; and/or as a processing aid to process plant materials and food industry by products with the aim to produce materials/products suitable as feed raw materials.

The laccases described herein can be used in the field of contact lens cleaning. For example, the laccases can be used in the cleaning, storage, disinfecting, and/or preservation of contact lens.

The laccases described herein can be used in the field of starch. For example, the laccases can be used in the processing of a substrate including starch and/or grain to glucose (dextrose) syrup, fructose syrup or any other syrup, alcohol (potable or fuel) or sugar. Such starch processing may include processing steps such as liquefaction, saccharification, isomerization, and de-branching of a substrate.

The laccases described herein can be used in the field of food. For example, the laccases can be used in the preparation, processing, or as an active ingredient in foods such as yellow fat, tea based beverages, culinary products, bakery, and frozen foods for human consumption. The laccases can be used, for example, as a bread improver, in food preservation, as an oxygen scavenger, etc.

The laccases described herein can be used in the field of personal care. For example, the laccases can be used in the preparation of personal products for humans such as fragrances, and products for skin care, hair care, oral hygiene, personal washing and deodorant and/or antiperspirants, for humans. The enzymes presented herein can be useful, for example, in hair dyeing and/or bleaching, nails dyeing and/or bleaching; skin dyeing and/or bleaching; surface modification (e.g., as coupling reagent); as an anti-microbial agent; in odor removal; teeth whitening; etc.

The laccases described herein can be used in the field of cleaning. For example, the laccases can be used in the cleaning, treatment or care of laundry items such as clothing or fabric; in the cleaning of household hard surfaces; in dishcare, including machine dishwashing applications; and in soap bars and liquids and/or synthetic surfactant bars and liquids. The enzymes presented herein can be useful, for example, in stain removal/de-colorization, and/or in the removal of odors, and/or in sanitization, etc.

The laccases described herein can be used in the field of waste-water treatment. For example, the laccases can be used in decolorization of colored compounds; in detoxification of phenolic components; for anti-microbial activity (e.g., in water recycling); in bio-remediation; etc.

The laccases described herein can be used in the field of bio-materials. For example, the laccases can be used as bio-catalysts for various organic reactions; and/or in connection with biopolymers; in connection with packaging; in connection with adhesives; in surface modification (activation and coupling agent); in production of primary alcohols; in connection with biosensors and/or organic syntheses; etc.

The laccases described herein can be used in the field of anti-microbials. For example, the laccases can be used as an anti-microbial agent in cleaning compositions, or for reducing or eliminating the microbial load of various foods (e.g., meats) or feed.

The laccase mediators can be used as sanitization and antimicrobial agents (e.g., wood protection, detergents). The mediators may be used independently of the enzymes or in conjunction with the enzymes.

As used herein, "cleaning compositions" and "cleaning formulations" refer to compositions that find use in the removal of undesired compounds from items to be cleaned, such as fabric, etc. The term encompasses any materials/compounds selected for the particular type of cleaning composition desired and the form of the product (e.g., liquid, gel, granule, or spray composition), as long as the composition is compatible with the incase and other enzyme(s) used in the composition. The specific selection of cleaning composition materials are readily made by considering the surface, item or fabric to be cleaned, and the desired form of the composition for the cleaning conditions during use.

The terms further refer to any composition that is suited for cleaning and/or bleaching any object and/or surface. It is intended that the terms include, but are not limited to detergent compositions (e.g., liquid and/or solid laundry detergents and fine fabric detergents; hard surface cleaning formulations, such as for glass, wood, ceramic and metal counter tops and windows; carpet cleaners; oven cleaners; and textile and laundry pre-spotters, as well as dish detergents).

Indeed, the term "cleaning composition" as used herein, includes unless otherwise indicated, granular or powder-form all-purpose or heavy-duty washing agents, especially cleaning detergents; liquid, gel or paste-form all-purpose washing agents, especially the so-called heavy-duty liquid (HDL) types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, car or carpet shampoos, bathroom cleaners; hair shampoos and hair-rinses; shower gels and foam baths and metal cleaners; as well as cleaning auxiliaries such as bleach additives and "stain-stick" or pre-treat types.

As used herein, the terms "detergent composition" and "detergent formulation" are used in reference to mixtures which are intended for use in a wash medium for the cleaning of soiled objects. In some embodiments, the term is used in reference to laundering fabrics and/or garments (e.g., "laundry detergents"). In alternative embodiments, the term refers to other detergents, such as those used to clean dishes, cutlery, etc. (e.g., "dishwashing detergents"). It is not intended that the presently contemplated compositions be limited to any particular detergent formulation or composition. Indeed, it is intended that in addition to laccase, the term encompasses detergents that contain surfactants, transferase(s), hydrolytic enzymes, builders, bleaching agents, bleach activators, bluing agents and fluorescent dyes, caking inhibitors, masking agents, enzyme activators, antioxidants, and solubilizers.

As used herein the term "hard surface cleaning composition," refers to detergent compositions for cleaning hard surfaces such as floors, walls, tile, stainless steel vessels (e.g., fermentation tanks), bath and kitchen fixtures, and the like. Such compositions are provided in any form, including but not limited to solids, liquids, emulsions, etc.

EXAMPLES

Example 1

Amino Acid Sequence Analysis of *Cerrena unicolor* Laccase

Four Peptide sequences were obtained using a commercially available laccase: AIGPVADLHI (SEQ ID No. 19), MLTPTSI (SEQ ID No. 20), TVGGPA (SEQ ID No. 21) and YSFVLNANQP (SEQ ID No. 22). The commercially available laccase was purified. N-terminal sequencing resulted in SEQ ID No. 19. Proteolytic digestion with trypsin of the purified sample was performed. Fragments were separated by gel electrophoresis with 3 bands selected and collected manually. Peptide sequencing was performed for each band and resulted in SEQ ID Nos. 20, 21 and 22.

Example 2 a. Cloning of *Cerrena unicolor* Laccase A Gene from ATCC20013 Strain

To clone the laccase A gene from ATCC 20013 strain, two primers were designed and obtained from Invitrogen: TTCG-CAGGTCAACGATATTC (SEQ ID No. 35) based on DNA sequence of the laccase B gene obtained from ATCC20013 strain (see example 3a) and GTTAGGTGGTTGAAG- GATTG (SEQ ID No. 36) based on laccase A gene obtained from CBS115.075 strain (see example 2c). The primers were used in a highT PCR reaction containing genomic DNA obtained from ATCC 20013 strain as template (see example 3). The PCR fragment was purified using a QIAquick spin column from Qiagen and cloned into pTOPO plasmid using TOPO cloning kit (Invitrogen). Twenty-two clones were amplified using Ready-To-Go PCR beads (GE Healthcare) and three PCR fragments (2-1, 2-3 and 2-6) were sequenced. 1316 bps DNA sequence of the laccase A gene from ATCC20013 is listed as SEQ ID No 37.

b. Cloning of *Cerrena unicolor* Laccase A Gene from CBS154.29 Strain

To clone the laccase A gene from CBS154.29 strain, two primer was designed and obtained from Invitrogen: CACCAGCATGAGCTCAAAGCTAC (SEQ ID No. 45) based on laccase A gene obtained from CBS115.075 strain (see example 2c) and primer of the SEQ ID No. 36. The primers were used in a Herculase PCR reaction containing genomic DNA template obtained from CBS154.29 strain, dNTPs, primer and 4% DMSO in 1× buffer. The PCR mixture was heated to 98° C. for 4 minutes to denature the DNA template. Herculase® II enzyme (Stratagene) was added to the tube and PCR reaction was performed in 30 cycles of 98° C. for 30 seconds, 50° C. for 30 seconds and 72° C. for 2 minute. The final extension at 72° C. was done for 5 minutes and the reaction was chilled to 4° C. The PCR fragment was purified using the QIAquick spin column and cloned into pENTR/D-TOPO vector (Invitrogen). Fifteen clones were amplified using Ready-To-Go PCR beads and plasmids were isolated from two clones (pENTR15-24 and pENTR15-30) and the DNA templates were sequenced. 2374 bps DNA sequence of the laccase A gene from CBS154.29 was obtained. The DNA sequence is listed as SEQ ID No. 3 and the translated protein sequence is listed as SEQ ID No. 4.

c. Cloning of *Cerrena unicolor* Laccase A Gene from CBS115.075 Strain

The primer CAATCTATGACCGTAGATTC (SEQ ID No. 39) based on the laccase B gene from ATCC20013 strain (see example 3a) and primer CGATCG (SEQ ID No. 38) where N represents a mixture of all four nucleotides (A, T, C and G) were used in lowT PCR reaction (see example 3a). Genomic DNA was extracted from *Cerrena unicolor* strain (CBS115.075) and was used as template in the first round of lowT PCR reaction. The PCR fragments were purified with a QIAquick spin column and used as template in the second round of lowT PCR reaction with primers of SEQ ID No. 35 based on the laccase B gene from ATCC20013 strain (see example 3a) and primer of the SEQ ID No. 38. The PCR fragments were cloned into pTOPO plasmid using TOPO cloning kit. Sixteen clones were amplified using Ready-To-Go PCR beads and three cloned PCR fragments (B2#1, B2#4 and B2#11) were sequenced.

To clone the 3' end of laccase A gene, the primer ACCGTGGTTCCTCCATTGCC (SEQ ID No. 40) and primer of SEQ ID No. 31 were used in the lowT PCR reaction with the genomic DNA extracted from *Cerrena unicolor* strain (CBS115.075) as template in the first round of lowT PCR reaction. The PCR fragments were purified with a QIAquick spin column and used as template in the second round of lowT PCR reaction with primers GACTGGCACTTGGAAGCGGG (SEQ ID No. 41) and primer of SEQ ID No. 31. The PCR fragments were cloned into pTOPO plasmid using TOPO cloning kit. Twenty-two clones were amplified using Ready-To-Go PCR beads and one cloned PCR fragment (D2#2) was sequenced.

To clone the 5' end of the laccase A gene, a primer, GGACCAAGCTGGTACTTTC (SEQ ID No. 42), was designed based on the laccase B gene sequence. It was used to amplify a DNA fragment with primer of SEQ ID No. 36. The genomic DNA extracted from *Cerrena unicolor* strain (CBS115.075) was used as the PCR template. The 1.7 kb PCR fragment was obtained, purified with a QIAquick spin column and cloned into pTOPO plasmid using TOPO cloning kit. Twenty-two clones were analyzed using Ready-To-Go PCR beads. Plasmid DNA from clone (C5#20) was sequenced. To further clone the 5' of laccase A gene, the primer CGTGGTACCAGTCTGCCAGGG (SEQ ID No. 43) and primer of SEQ ID No. 31 were used in the lowT PCR reaction with the genomic DNA extracted from *Cerrena unicolor* CBS115.075 strain as template. From the first round of lowT PCR reaction, the PCR fragment was purified with a QIAquick spin column and used as template in the second round of lowT PCR reaction with primers GGCAGCATCAGTCACGGTCAG (SEQ ID No. 44) and primer of SEQ ID No. 31. The PCR fragment (a3) was amplified again and used as template in a third round of lowT PCR reaction with primers GGCAGCATCAGTCACGGTCAG (SEQ ID No. 44) and primer of SEQ ID No. 31. The PCT fragment (a3-2) was cloned into pTOPO plasmid using TOPO cloning kit. Eleven clones were amplified using Ready-To-Go PCR beads and two cloned PCR fragments (a3-2#10 and a3-2#11) were sequenced. The DNA sequence of the laccase A gene from CBS 115.075 strain including the sequence of 5' and 3' of the coding region is listed as SEQ ID No. 1 and the translated protein sequence is listed as SEQ ID No. 2.

Example 3 a. Cloning and Sequencing of the *Cerrena unicolor* Laccase B Gene from ATCC20013 Strain To clone the DNA fragment encoding the *Cerrena* laccase gene, four degenerated primers were designed based on the peptide sequence AIGPVADLHI (SEQ ID No. 19) and obtained from Invitrogen. They are named as

```
                                    (SEQ ID No. 23)
    primerA       GCAATCGGACCNGTNGCAGA;

(SEQ ID No. 24)
    primerB       GCAATCGGACCNGTNGCTGA;

(SEQ ID No. 25)
    primerC       GCAATCGGACCNGTNGCGGA
    and (SEQ ID No. 26)
    primerD       GCAATCGGACCNGTNGCCGA.
```

Two degenerated primers were designed based on the peptide sequence YSFVLNANQP (SEQ ID No. 22) and obtained from Invitrogen. They are named as

```
                                    (SEQ ID No. 27)
    primerE       GGTTGATTTGCATTNAGNAC
    and (SEQ ID No. 28)
    primerF       GGTTGATTTGCGTTNAGNAC
``` where N represents a mixture of all four nucleotides (A, T, C and G). The genomic DNA was extracted from ATCC20013 strain and used as template in the lowT PCR reaction contain following combination of primers: PCR reaction 1 contains no DNA and no primer; PCR reaction 2 contains primerA and primerE; PCR reaction 3 contains primerB and primerE; PCR reaction 4 contains primerC and primerE; PCR reaction 5 contains primerD and primerE; PCR reaction 6 contains primerA and primerF; PCR reaction 7 contains primerB and primerF; PCR reaction 8 contains primerC and primerF and PCR reaction 9 contains primerD and primerF. The PCR reaction mixture contained DNA template, primers, 1× buffer, 0.2 mM dNTP and 1 unit of Taq DNA polymerase. The PCR reaction was performed in 30 cycles of 95° C. for 1 minute, 45° C. for 1 minute and 68° C. for 1 minute. The final extension at 72° C. was done for 7 minutes and the reaction was chilled to 4° C. The PCR fragments from reaction 4, 5 and 8 were cut out of a 1.2% agarose gel and pooled. The PCR fragments were extracted from gel with a Qiagen spin column and cloned into pTOPO plasmid using TOPO cloning kit. Thirty-two cloned PCR fragments were selected and sequenced using Ready-To-Go PCR beads and DNA sequence of clone #A30 was identified as laccase B gene.

To clone the 5' end of laccase gene, a primer was designed and obtained from Invitrogen: GGACGTGGCCTTGAG-CATAC (SEQ ID No. 29). It was used in first round of lowT PCR reaction with a degenerated oligo NNNNNNNNNNG-GATCC (SEQ ID No. 31) where N represents a mixture of all four nucleotides (A, T, C and G). The PCR product was purified using a QIAquick spin column and used as template in a second lowT PCR reaction containing a primer TCTGT-CAAGTCGTCAATCAC (SEQ ID No. 30) and primer of SEQ ID No. 31. The PCR fragment was purified using a QIAquick spin column and diluted 1:10 and 1:100 and used as template in the first round of highT PCR reaction performed in 30 cycles of 95° C. for 1 minute, 50° C. for 1 minute and 72° C. for 1 minute with two primers (SEQ ID No. 30 and SEQ ID No. 31). The final extension at 72° C. was done for 7 minutes and the reaction was chilled to 4° C. The PCR fragment was purified with a QIAquick spin column and used in the second round of highT PCR reaction with primers of TTACCAC-GAATCAGAGGACC (SEQ ID No. 32) and SEQ ID No. 31. The PCR fragment (D13) was sequenced.

To clone the 3' end of the laccase B gene, a primer was designed and obtained from Invitrogen: CCTCACCTGTAT-TGGCACAG (SEQ ID No. 33) and used with primer of SEQ ID No. 31 in a first round of lowT PCR reaction. The PCR fragment was purified in a QIAquick spin column and used as template in second round of lowT PCR reaction with primer TTGGTATCATGCCCTTGCTC (SEQ ID No. 34) and primer of SEQ ID No. 31. The PCR fragment was cloned into a pTOPO plasmid using TOPO cloning kit. Sixteen clones were amplified using Ready-To-Go PCR beads and four cloned PCR fragments (C3, C4, C5 and C7) were sequenced.

1337 bps DNA fragment was obtained. The DNA sequence is listed as SEQ ID No. 9 and translated protein sequence is listed as SEQ ID No. 10.

b. Cloning of *Cerrena unicolor* Laccase B Gene from CBS154.29 Strain

Two primers were designed and obtained from Invitrogen:

CACCGCGATGTCTCTTCTTCGTAG (SEQ ID No. 46)

and

TGRAGRTGGAASGGATGWGGTCC (SEQ ID No. 47)

where R represent mixture of nucleotides A and G, S represent mixture of nucleotides C and G, and W represent mixture of nucleotides A and T. The two primers were used in the highT PCR reaction. The PCR fragment (A3) was purified using a QIAquick spin column. The PCR fragment was cloned into pTOPO plasmid using TOPO cloning kit. Sixteen clones were amplified using Ready-To-Go PCR beads and two PCR fragments (A3#1 and A3#5) were sequenced.

To clone the 3' end of the laccase B gene from CBS154.29 strain, a primer was designed and obtained from Invitrogen: GTCCCTGTACTACTCCAGATCC (SEQ ID No. 48) and used with a primer having SEQ ID No. 31 in first round of lowT PCR reaction. The PCR fragment was purified in a QIAquick spin column and used as template in second round of lowT PCR reaction with primer CCAGCAGGAAGCGT-GATCGAAC (SEQ ID No. 49) and primer of SEQ ID No. 31. The PCR fragment was cloned into pTOPO plasmid using TOPO cloning kit. Sixteen clones were amplified using Ready-To-Go PCR beads and three PCR fragments (7#6, 7#7 and 7#8) were sequenced. 2663 bps of the laccase B DNA sequence of the CBS154.29 strain is listed as SEQ ID No. 7 and translated protein sequence is listed as SEQ ID No. 8.

c. Cloning of *Cerrena unicolor* Laccase B Gene from CBS115.075 Strain

A primer was designed and obtained from Invitrogen: GTAATCATGTATCACCTGGGCTCAAGG (SEQ ID No. 50). The primer was used in the Herculase PCR reaction (see Example 2b) with primer of SEQ ID No. 46. The PCR fragment was purified using a QIAquick spin column. The PCR fragment was cloned into pTOPO plasmid using TOPO cloning kit. Seventeen clones were analyzed using Ready-To-Go PCR beads and the PCR fragments from four clones (#1, #2, #4 and #5) were sequenced. The plasmid DNA was prepared from two clones (pENTR-laccaseB CBS115075#1 and pENTR-laccaseB CBS115075#3) and both plasmids were sequenced. 2173 bps of the laccase B DNA sequence of the CBS115.075 strain is listed as SEQ ID No. 5 and translated protein sequence is listed as SEQ ID No. 6.

Example 4

Cloning of the *Cerrena unicolor* Laccase C Gene from CBS154.29 Strain

A primer ACGAACGAGTANCGTTGNCC (SEQ ID No. 51), where N represents a mixture of all four nucleotides (i.e., A, T, C and G), was designed based on the translated peptide sequence GQRYSFV (SEQ ID No. 52). This peptide is conserved between the laccase A gene and the laccase B gene (see Examples 2 and 3). The primer was obtained from Invitrogen and was used in the lowT reaction with primer of the SEQ ID No. 24. The PCR fragment was purified using a QIAquick spin column. The PCR fragment was cloned into pTOPO plasmid using TOPO cloning kit. Thirty-three clones were analyzed using Ready-To-Go PCR beads and the PCR fragments from four clones (#12, #5a, #19a and #21a) were sequenced. 1080 bps of the laccase C gene sequence from the CBS154.29 strain is listed as SEQ ID No. 11 and translated protein sequence is listed as SEQ ID No. 12.

Example 5 a. Cloning of *Cerrena unicolor* Laccase D Gene from CBS115.075 Strain

To clone the 5' end of the laccase D gene from CBS115.075 strain, a primer was designed based on laccase D gene from CBS154.29 strain (see Example 5b) (AACACGGAGACAGTCCAAAC, SEQ ID No. 62). It was used in the highT PCR reaction with primer of SEQ ID No. 56. The PCR fragment was purified using a QIAquick spin column and sequenced.

To clone the laccase D gene from CBS115.075 strain, two primers (CACCTCTCGAGATGGGATTGAAC, SEQ ID No. 63 and CGTTTAAATAGCAGTTCCTTTC, SEQ ID No. 64) were designed based on the laccase D gene from CBS154.29 strain (see example 5b). The primers were used in a Herculase PCR reaction (see example 2b) with DNA template of the genomic DNA from CBS115.075 strain. The PCR fragment was purified using the QIAquick spin column and cloned into pENTR/D-TOPO vector. Sixteen clones were amplified using Ready-To-Go PCR beads and the PCR fragments generated from four clones were sequenced. The plasmids were isolated from clone #2 (pENTRE-laccaseD#2) and it was sequenced. 2809 bps DNA sequence of the laccase D gene from CBS115.075 was obtained. The DNA sequence is listed as SEQ ID No. 15 and the translated protein sequence is listed as SEQ ID No. 16.

b. Cloning of *Cerrena unicolor* Laccase D Gene from CBS154.29 Strain

A primer. CTGGTTGGTTNGCATTNAG (SEQ ID No. 53), was designed based on the peptide sequence LNANQP (SEQ ID No. 54). The primer was obtained from Invitrogen and used in the lowT PCR reaction with primer of the SEQ ID No. 26. The PCR fragment was purified using a QIAquick spin column and was cloned into pTOPO plasmid using TOPO cloning kit. Eighteen clones were analyzed using Ready-To-Go PCR beads and PCR fragment from a clone was sequenced.

To clone the 3' end of the laccase D gene, a primer (CACACGACCCCTGACCGTTG, SEQ ID No. 55) was designed. The primer was used in the lowT PCR reaction with primer of the SEQ ID No. 31. The PCR fragment was purified using a QIAquick spin column and was cloned into pTOPO plasmid using TOPO cloning kit. Twenty-four clones were analyzed using Ready-To-Go PCR beads and PCR fragment(s) from a clone were sequenced.

To clone more of the 3' and the 5' ends of the laccase D gene, inverse PCR was used. 0.4 ug of the genomic DNA from the *Cerrena* CBS154.29 strain was digested with EcoRV restriction enzyme at 37° C. for 1.5 hours. Digested genomic DNA fragments were precipitated with ethanol. The linear DNA fragments were ligated with T4 DNA ligase in 100 ul volume for more than 5 hours. The ligated DNA fragments were heated to 100° C. for 3 minutes and were used as the DNA template in a first round of the highT PCR reaction using two primers (TGACCGGTGATCAACGTCCC, SEQ ID No. 56, and GGCGCAGACATCAATCACAG, SEQ ID No. 57). The PCR fragments were purified using a QIAquick spin column and were used as a DNA template in the second round of the highT PCR reaction using two primers (TCTTCAGCATCAACAACGCC, SEQ ID No. 58 and TCCGGCAAGCACGGTTGG, SEQ ID No. 59). The PCR fragments from second round of PCR reaction were purified using a QIAquick spin column and were sequenced.

To clone more of the 3' end of laccase D gene from CBS154.29 strain, inverse PCR was used. 0.4 ug of the genomic DNA from the *Cerrena* CBS154.29 strain was digested with SmaI restriction enzyme at 37° C. for 1.5 hours. Digested genomic DNA fragments were precipitated with ethanol. The linear DNA fragments were ligated with T4 DNA ligase in 100 ul volume for more than 5 hours. The ligated DNA fragments were heated to 100° C. for 3 minutes and were used as the DNA template in a first round of highT PCR reaction with primer TCGTCTTCGCTGAGGGCATC, SEQ ID No. 60, and primer of SEQ ID No. 56. The PCR fragments were purified using a QIAquick spin column and were used as DNA template in the second round of the highT PCR reaction using primer (CAGACCGCTGCAGCCAACCC, SEQ ID No. 61) and primer of SEQ ID No. 59. The PCR fragments from the second round of PCR reaction were purified using a QIAquick spin column and cloned into pTOPO plasmid using TOPO cloning kit. Twenty-one clones were analyzed using Ready-To-Go PCR beads and PCR fragment from clones #Cell and #Ce14 were sequenced. 2809 bps of the laccase D gene sequence from the CBS154.29.49 strain is listed as SEQ ID No. 13 and the translated protein sequence is listed as SEQ ID No. 14.

Example 6

Cloning of *Cerrena unicolor* Laccase E Gene from CBS154.29 Strain

The primer of SEQ ID No. 53 was used in the lowT PCR reaction with primer of the SEQ ID No. 26 (see Example 5b). The PCR fragment was purified using a QIAquick spin column and was cloned into pTOPO plasmid using TOPO cloning kit. Eighteen clones were analyzed using Ready-To-Go PCR beads and the PCR fragment from clone #Ae17 was sequenced. 1163 bps of the laccase E gene sequence from the CBS154.29.49 strain is listed as SEQ ID No. 17 and the translated protein sequence is listed as SEQ ID No. 18.

Example 7

Expression of Laccase A Gene in *Trichoderma*

To construct the expression plasmid for the laccase A gene of the CBS strain 115.075, two primers (SEQ ID No. 45 and SEQ ID No. 36) were used in the Herculase PCR reaction containing genomic DNA template obtained from 115.075 strain, dNTPs, and 4% DMSO in 1× buffer. The PCR mixture was heated to 98° C. for 4 minutes to denature the DNA template. Herculase® II enzyme (Stratagene) was added to the tube and PCR reaction was performed in 30 cycles of 98° C. for 30 seconds, 50° C. for 30 seconds and 72° C. for 2 minute. The final extension at 72° C. was done for 5 minutes and the reaction was chilled to 4° C., The PCR fragment was purified using the QIAquick spin column and cloned into pENTR/D-TOPO vector. Fifteen clones were amplified using Ready-To-Go PCR beads and plasmid DNA was isolated from pENTR-laccaseA-CBS115.075#11 clone. The laccase A gene portion was sequenced to confirm fidelity of the PCR amplification of the laccase A gene. The plasmid of pENTR-laccaseA-CBS115.075#11 (50 ng) was converted to the expression plasmid pTrex3g-laccaseA (FIG. 1) in a 10 ul LB clonase II reaction (Invitrogen) containing 6.5 ul of 1E, 1 ul of pTrex3g vector (0.1 mg/ml) and 2 ul of ClonaseII. The expression plasmid was confirmed by DNA sequencing and transformed biolistically into a *Trichoderma* strain. Transformation of the *Trichoderma* strain by the biolistic transformation method was accomplished using a Biolistic® PDS-1000/ the Particle Delivery System from Bio-Rad (Hercules, Calif.) following the manufacturers instructions (see WO 05/001036 and US 2006/0003408). Sixty-six transformants were selected and were transferred to new plates. A total of 15 stable transformants were grown in 30 ml of the Proflo media for 2 days at 30° C. Five mls of 2 days old culture from Proflo media were transferred to 50 mls of defined media containing 1 mM copper. The cultures were grown for 5 days at 28° C. Culture broths were centrifuged and supernatants were used for ABTS assay.

Example 8 a. Expression of Laccase B Gene in *Aspergillus*

Figure 2:
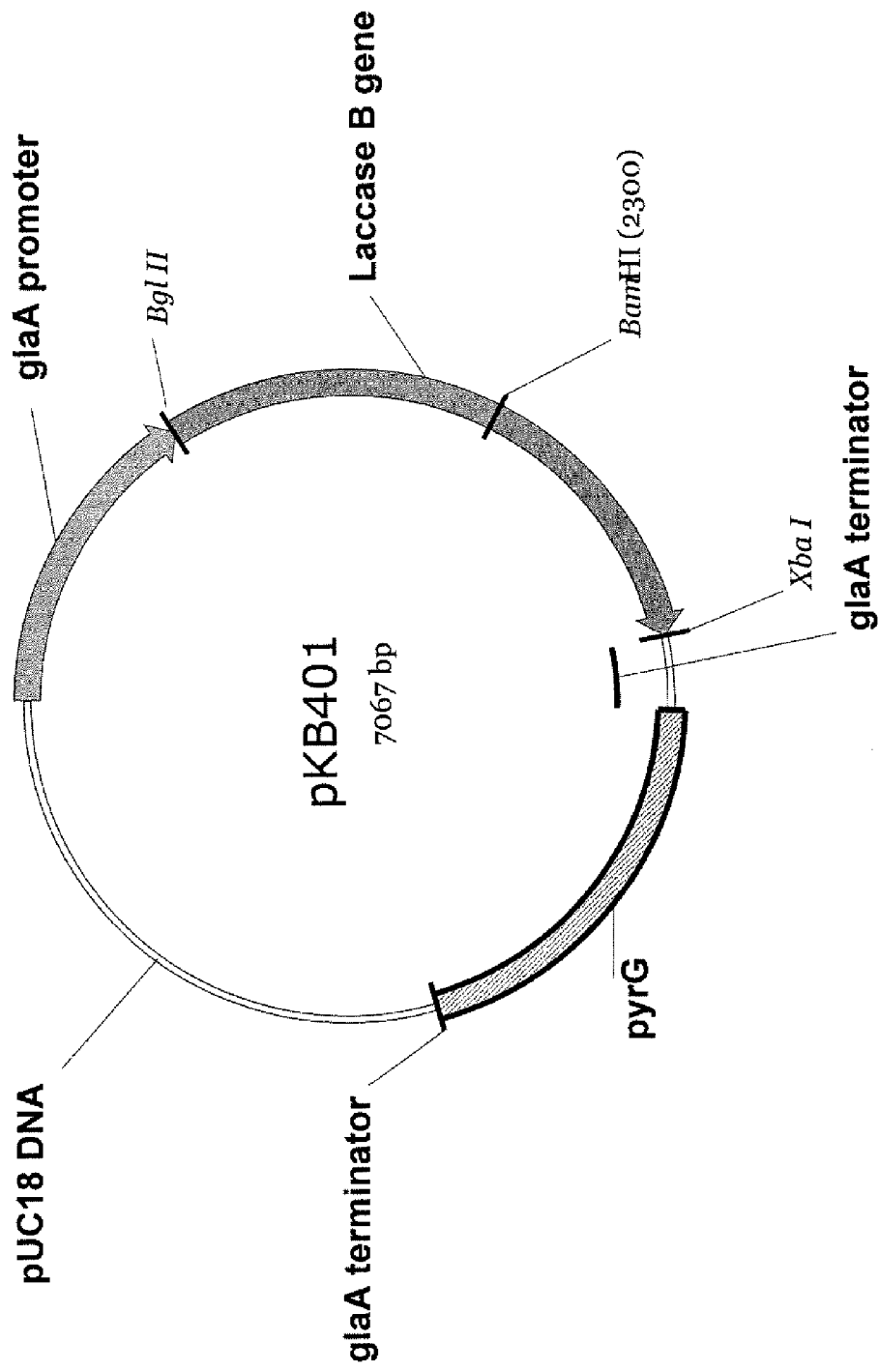
FIG. 2 is a schematic of the *Aspergillus* expression plasmid, pKB401, used in Example 8a. The laccase B gene may be replaced with other laccase genes described herein.
Figure 3:
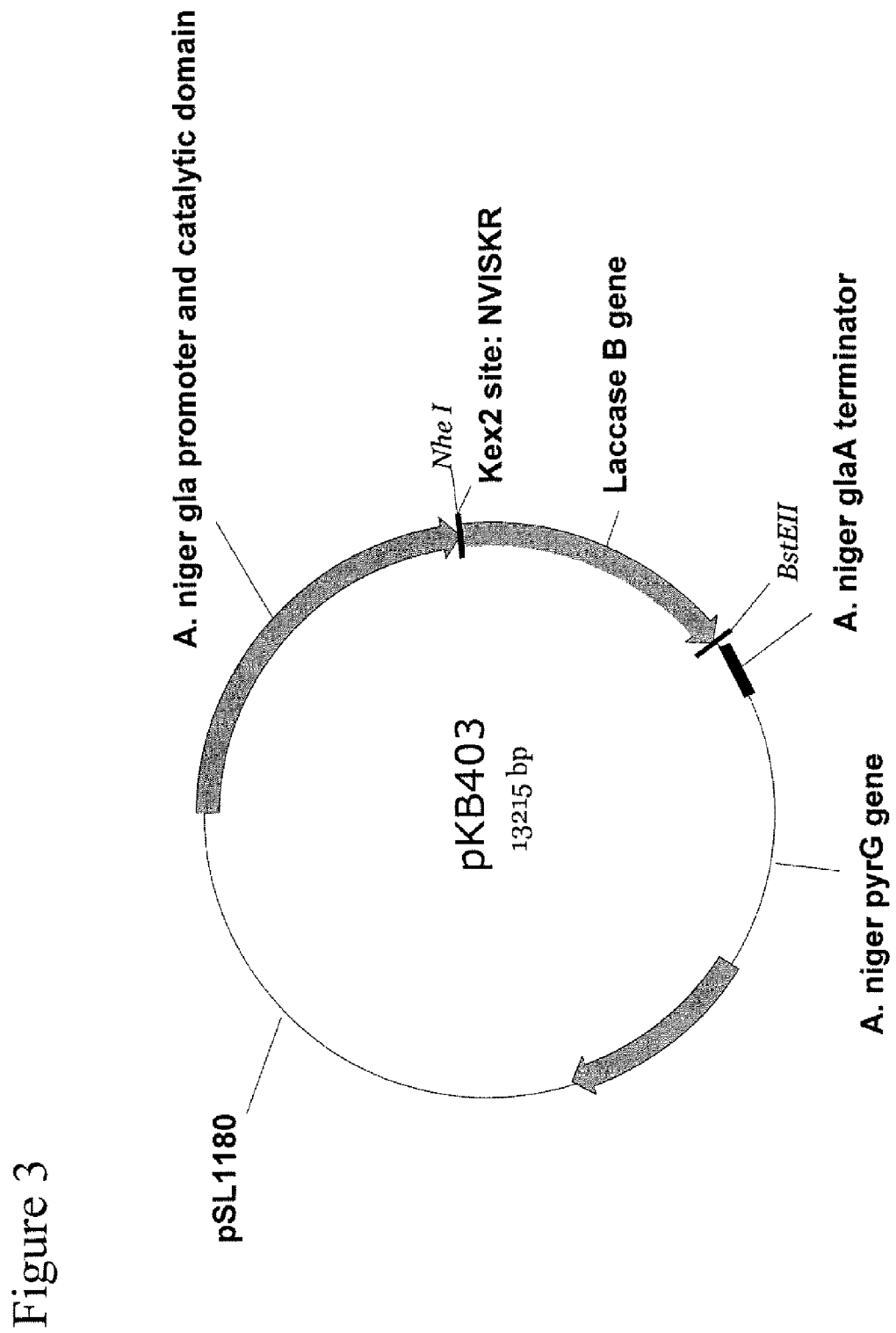
FIG. 3 is a schematic of the *Aspergillus* expression plasmid, pKB403, used in Example 8b. The laccase B gene fused to gene encoding the catalytic domain of glucoamylase. The laccase B gene may be replaced with other laccase genes described herein.

To construct the expression plasmid for the laccase B gene of the CBS strain 115.075, two primers GCAGATCTGC-GATGTCTCTTCTTCGTAGCTTGAC (SEQ ID No. 72) and GAGGTCACCTCTAGATCATGTATCAC-CTGGGCTCAAGGCATC (SEQ ID No. 73) were used in the Herculase PCR reaction containing genomic DNA template obtained from 115.075 strain (see Example 2b). The PCR fragment was purified using the QIAquick spin column and digested with restriction enzyme BgIII and XbaI. The DNA fragment was purified again with the QIAquick spin column and was cloned into BgIII and XbaI digested pGAPT vector. Fidelity of the plasmid was confirmed by DNA sequencing. The resulting plasmid pKB401 (FIG. 2) was transformed into *A. niger* 2445 for checking expression of laccase B gene. Thirty-four transformants were selected and were transferred onto MM plates and grew for 4 days at 30° C. A small plug of single colony including spores and mycelium was innoculated on to a CMA plate and grew for 4 days at 30° C. A plug of CMA plate containing confluent spores and mycelium was transferred into to 30 mls of Promosoy special broth (pH6.2) containing 1 mM copper. The cultures were grown for 5 days at 30° C. Culture broths were centrifuged and supernatants were used for ABTS assay.

b. Expression of Laccase B Gene in *Aspergillus* as Fusion to Catalytic Domain of the Glucoamylase To construct the fusion expression plasmid for the laccase B gene of the CBS strain 115.075, two primers TTGCTAG-CAACGTGATCTCCAAGCGTGCAATCG-GTCCAGTCACTGACCTAC (51mer, SEQ ID No. 74) and primer of SEQ ID No. 73 were used in the Herculase PCR reaction containing genomic DNA template obtained from CBS115.075 strain (see Example 2b). The PCR fragment was purified using the QIAquick spin column and digested with NheI and BstEII and was purified again with the QIAquick spin column. This purified fragment was cloned into NheI and BstEI digested vector pGAMpR2-GV (see US Patent application US20050153399). The resulting plasmid pKB403 (FIG. 3) was confirmed by sequencing analysis and was transformed into *A. niger* 2445. Twenty-eight transformants were selected and were transferred onto MM plates and grew for 4 days at 30° C. A small plug of single colony including the spores and mycelium were innoculated onto CMA plate and grew for 4 days at 30° C. A plug of CMA plate containing confluent spores and mycelia was transferred into to 30 mls of Promosoy special broth (pH6.2) (see US Patent application US20050153399) containing 1 mM copper. The cultures were grown for 5 days at 30° C. Culture broths were centrifuged and supernatants were used for ABTS assay.

c. Expression of Laccase B Gene in *Trichoderma*

To construct expression plasmid for the laccase B gene of the CBS115.075 strain (see Example 2b). A primer was designed and obtained from Invitrogen GTAATCATGTAT-CACCTGGGCTCAAGG (SEQ ID No. 50). The primer was used in the Herculase PCR reaction (see Example 2b) with primer of SEQ ID No. 46. The PCR fragment was purified using the QIAquick spin column and cloned into pENTR/D-TOPO vector (Invitrogen). Seventeen clones were amplified using Ready-To-Go PCR beads and plasmid DNA was isolated from pENTR-CBS115.075#1 clone (see Example 3c). The laccase B gene portion was sequenced to confirm fidelity of the PCR amplification. The plasmid of pENTR-laccaseB-CBS115.075#1 (50 ng) was converted to expression plasmid pTrex3g-laccaseB (see FIG. 1 with the laccase A gene replaced with the laccase B gene) in a 10 ul LB clonase II reaction (Invitrogen) containing 6.5 ul of TE, 1 ul of pTrex3g vector (0.1 mg/ml) and 2 ul of ClonaseII. The expression plasmid was confirmed by DNA sequencing and transformed biolistically into a *Trichoderma* strain. Sixty transformants were selected and were transferred to new plates. A total of 20 stable transformants were grown in 30 ml of the Proflo media for 2 days at 30° C. Three mls of 2 day old culture from Proflo media were transferred to 30 mls of defined media (see US Patent Application 20050153399) containing 1 mM copper. The cultures were grown for 4 days at 28° C. Culture broths were centrifuged and supernatants were used for ABTS assay.

d. Expression of the Laccase B Gene in *Trichoderma* as CBH1 Fusion

To construct the expression plasmid for the laccase B gene of the CBS strain 115.075, a primer was designed and obtained from Invitrogen (GGACTAGTGTCGCCGTTTA-CAAACGCGCAATCGGTCCAGTCACTGACC, SEQ ID No. 65). The primer was used in combination with the reverse primer (obtained from New England Biolab) in the Herculase PCR reaction containing pENTR-laccaseB CBS115075#1 (see example 3c) as the DNA template.

```
The PCR fragment
                                                    (SEQ ID No. 66)
ACTAGTGTCG CCGTTTACAA ACGCGCAATC GGTCCAGTCA CTGACCTACA      50

TATAGTGAAC CAGAATCTCG ACCCAGATGG TTTCAACCGC CCCACTGTAC     100

TCGCAGGTGG TACTTTCCCC GGTCCTCTGA TTCGTGGTAA CAAGGTACGC     150

TTCATAACCG CCCTCCGTAG ACGTAGGCTT CGGCTGACAT GACCATCATC     200

TGTAGGGAGA TAACTTTAAA ATTAATGTGA TTGACGACTT GACAGAGCAC     250

AGTATGCTCA AGGCTACGTC CATCGTAAGT CCCTGATTAA CGTTTCACCT     300
```

-continued

```
GGTCATATCG CTCAACGTCT CGAAGCACTG GCATGGGTTC TTCCAGAAGG        350

GAACCAACTG GGCCGATGGC CCCGCCTTTG TCACCCAATG TCCTATCACA        400

TCAGGAAACG CCTTCCTGTA TGATTTCAAC GTTCCGGACC AAGCTGGTAC        450

TTTCTGGTAC CACAGCCATC TCTCTACACA GTATTGTGAC GGTCTTCGTG        500

GTGCCTTTGT CGTCTATGAT CCTAATGATC CCAACAAGCA ACTCTATGAT        550

GTTGATAACG GCAAGTTCCT TGCATATTTC ATTTCTATCA TATCCTCACC        600

TGTATTGGCA CAGAAAGCAC CGTGATTACC TTGGCTGATT GGTATCATGC        650

CCTTGCTCAG ACTGTCACTG GTGTCGCGTG AGTGACAAAT GGCCCTCAAT        700

TGTTCACATA TTTTCCTGAT TATCATATGA TAGAGTATCT GATGCAACGT        750

TGATCAACGG ATTGGGACGT TCGGCCACCG GCCCCGCAAA TGCCCCTCTG        800

GCGGTCATCA GTGTCGAGCG GAATAAGAGG TCAGTTCCAT AATTATGATT        850

ATTTCCCGCG TTACTTCCTA ACAATTATTT TTGTATCCCT CCACAGATAT        900

CGTTTCCGAT TGGTTTCTAT TTCTTGCGAC CCTAACTTTA TTTTCTCAAT        950

TGACCACCAC CCAATGACCG TAATTGAGAT GGACGGTGTT AATACCCAAT       1000

CTATGACCGT AGATTCGATC CAAATATTCG CAGGTCAACG ATATTCATTT       1050

GTCGTAGGTT ATTATAAACT GCCCACCGAT CATCTCTCAC GTAACTGTTA       1100

TAGATGCAAG CCAACCAACC AGTTGGAAAT TATTGGATCC GCGCTAAACC       1150

TAATGTTGGG AACACAACTT TCCTTGGAGG CCTGAACTCC GCTATATTAC       1200

GATATGTGGG AGCCCCTGAC CAAGAACCGA CCACTGACCA AACACCCAAC       1250

TCTACACCGC TCGTTGAGGC GAACCTACGA CCCCTCGTCT ATACTCCTGT       1300

GGTATGTTGT TCTCGTTACA TATACCAAAC CTAAATGAAG ACTGAACGG        1350

ATCTACTAGC CGGGACAGCC ATTCCCTGGC GGTGCTGATA TCGTCAAGAA       1400

CTTAGCTTTG GGTTTCGTAC GTGTATTTCA CTTCCCTTTT GGCAGTAACT       1450

GAGGTGGAAT GTATATAGAA TGCCGGGCGT TTCACAATCA ATGGAGCGTC       1500

CCTCACACCT CCTACAGTCC CTGTACTACT CCAGATCCTC AGTGGTACTC       1550

ACAATGCACA GGATCTTCTC CCAGCAGGAA GCGTGATCGA ACTTGAACAG       1600

AATAAAGTTG TCGAAATCGT TTTGCCCGCT GCGGGCGCCG TTGGCGGTCC       1650

TCATCCTTTT CACTTACATG GTGTAAGTAT CAGACGTCCT CATGCCCATA       1700

TTGCTCCGAA CCTTACACAC CTGATTTCAG CACAATTTCT GGGTGGTTCG       1750

TAGCGCCGGT CAAACCACAT ACAATTTCAA TGATGCTCCT ATCCGTGATG       1800

TTGTCAGTAT TGGCGGTGCA AACGATCAAG TCACGATCCG ATTTGTGGTA       1850

TGTATCTCGT GCCTTGCATT CATTCCACGA GTAATGATCC TTACACTTCG       1900

GGTTCTCAGA CCGATAACCC TGGCCCATGG TTCCTTCACT GTCACATTGA       1950

CTGGCATTTG GAGGCTGGGT TCGCTGTAGT CTTTGCGGAG GGAATCAATG       2000

GTACTGCAGC TGCTAATCCA GTCCCAGGTA AGACTCTCGC TGCTTTGCGT       2050

AATATCTATG AATTTAAATC ATATCAATTT GCAGCGGCTT GGAATCAATT       2100

GTGCCCATTG TATGATGCCT TGAGCCCAGG TGATACATGA TTACAAGGGT       2150

Figure 4:
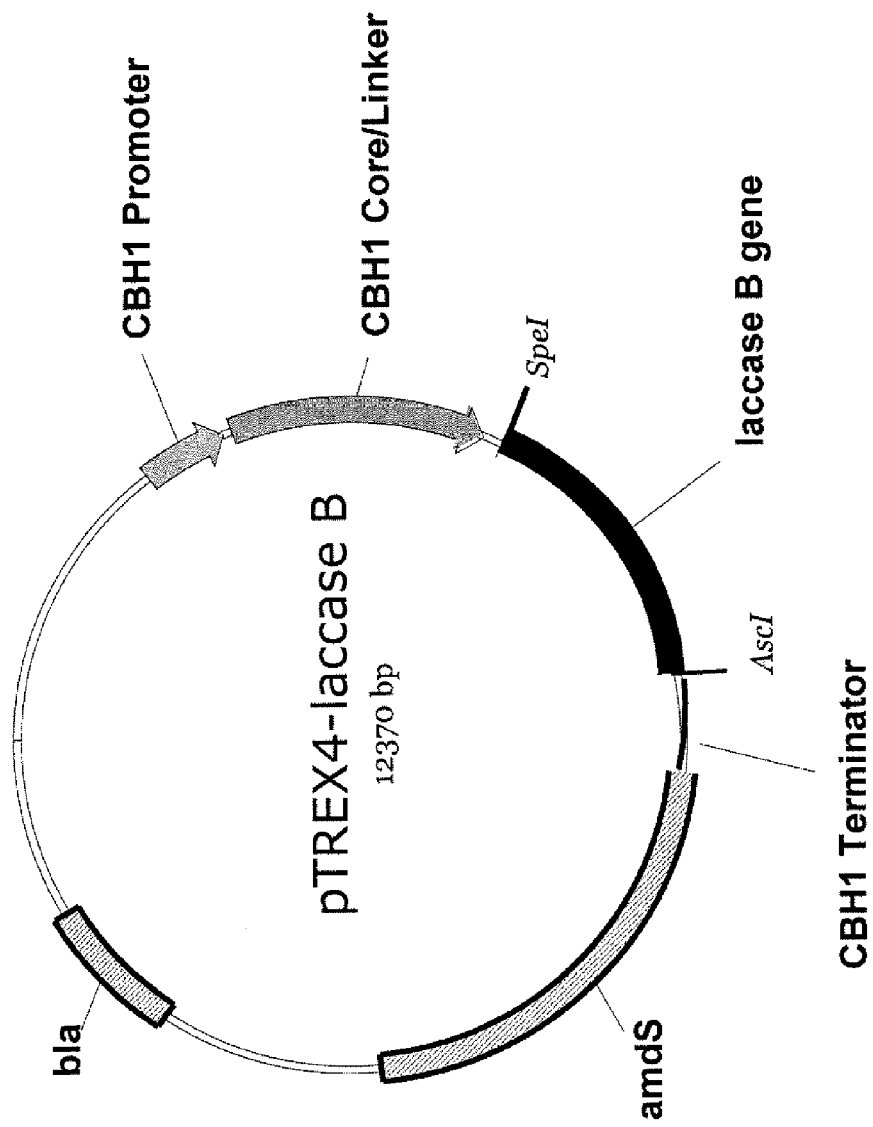
FIG. 4 is a schematic of the *Trichoderma* expression plasmid, pTrex4-laccaseB, used in Example 8d. The laccase B gene fused to gene encoding the catalytic domain of CBH1. The laccase B gene may be replaced with other laccase genes described herein.

GGGCGCGCC                                                   2159
``` was purified using the QIAquick spin column and digested with restriction enzymes SpeI and AscI This fragment (SEQ ID No. 66) was then cloned into pTrex4 vector which was also digested with SpeI and AscI to create the expression plasmid (pTrex4-laccaseB, FIG. 4). The fidelity of the expression plasmid was confirmed by DNA sequencing and transformed biolistically into a *Trichoderma* strain. More than 100 transformants were generated and sixty transformants were transferred to new plates. A total of 20 stable transformants were grown in 30 ml of the Proflo media for 2 days at 30° C. Five mls of 2 days old culture from Proflo media were transferred to 50 mls of defined media containing 1 mM copper. The cultures were grown for 4 days at 28° C. Culture broths were centrifuged and supernatants were used for ABTS assay.

Example 9 a. Expression of Laccase B Gene of the CBS Strain 115.075 in *Streptomyces*

Figure 5:
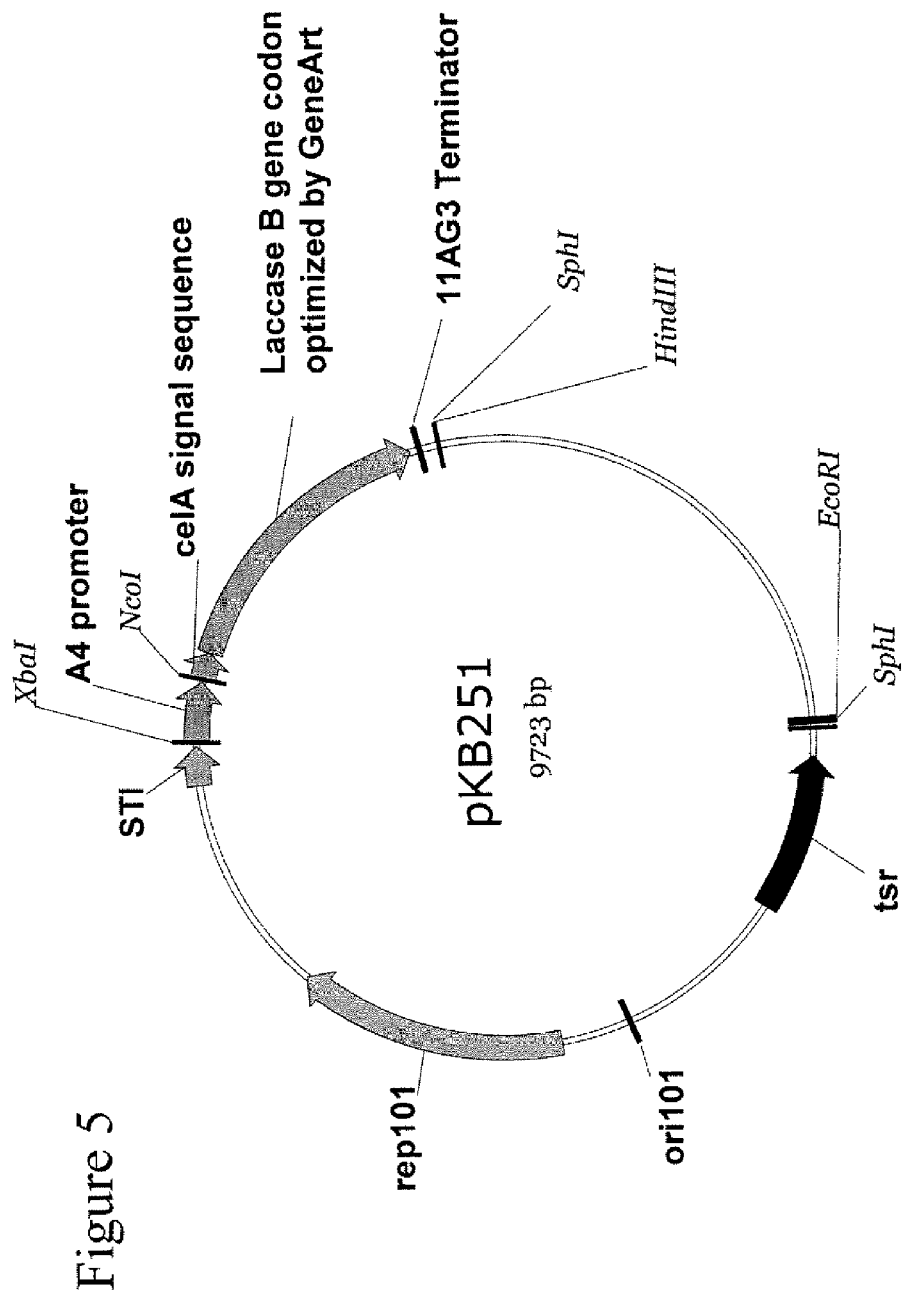
FIG. 5 is a schematic of the *Streptomyces* expression plasmid (pKB251) for codon optimized laccase B gene, used in Example 9.

The laccase B protein sequence was used for codon optimization according to *Streptomyces lividans* codon usage. To construct the expression plasmid for the synthesized laccase B gene of the CBS115.075 strain in *Streptomyces*, two primers ACGCAGCCTGAACTAGTTGCGATCCTCTAGAG (SEQ ID No. 75) and CTCTGATCAAGGTCATCAGGT-GTCGCCCGGGGACAGG (SEQ ID No. 76) were used in the Herculase PCR reaction containing the optimized DNA template (See Example 2b). The PCR fragment was purified using the QIAquick spin column and was digested with XbaI and BclI. The digested fragment was purified by the QIAquick spin column and was cloned into XbaI and BamHI digested pKB105 (see US 20060154843). The correctness of the resulting plasmid pKB251 (FIG. 5) was confirmed by DNA sequencing. The DNA of plasmid pKB251 was transformed into *Streptomyces lividans* g3s3 strain (see US 20060154843). Twelve thiostrepton resistant transformants were picked and transferred into seed shake flask (20 ml of TSG medium containing 50 ug/ml of thiostrepton in DMSO), grown for 2 days at 30° C. Three mls of 2 days old culture from seed shake flask were transferred to 30 mls of *Streptomyces* modified production medium II containing 1 mM copper. The cultures were grown for 4 days at 30° C. Culture broths were centrifuged and supernatants were used for ABTS assay.

Example 10

Expression of the Laccase B Gene in *Trichoderma* as CBH1 Fusion Using Codon Optimized Synthetic Gene

```
The optimized synthetic laccase B gene (SEQ ID NO: 67):
ACTAGTGTCG CCGTTTACAA ACGCGCAATC GGTCCCGTCA CTGACCTGCA        50

TATTGTGAAC CAGAATCTCG ACCCCGATGG TTTCAACCGC CCCACTGTCC       100

TCGCAGGTGG TACTTTCCCC GGTCCTCTGA TTCGTGGTAA CAAGGGAGAT       150

AACTTTAAAA TTAATGTGAT TGACGACTTG ACAGAGCACA GCATGCTCAA       200

GGCTACGTCC ATCCACTGGC ATGGCTTCTT CCAGAAGGGA ACCAACTGGG       250

CCGATGGCCC CGCCTTTGTC ACCCAATGTC CTATCACATC AGGAAACGCC       300

TTCCTGTACG ATTTCAACGT TCCGGACCAA GCTGGTACTT TCTGGTACCA       350

CAGCCATCTC TCTACACAGT ACTGTGACGG TCTTCGTGGT GCCTTTGTCG       400

TCTACGATCC TAATGATCCC AACAAGCAAC TCTACGATGT TGATAACGGC       450

AACACCGTGA TTACCTTGGC TGATTGGTAC CATGCCCTTG CTCAGACTGT       500

CACTGGTGTC GCAGTCTCTG ATGCAACGTT GATCAACGGA TTGGGACGTT       550

CGGCCACCGG CCCCGCAAAT GCCCCTCTGG CGGTCATCAG CGTCGAGCGC       600

AATAAGCGCT ATCGTTTCCG ATTGGTTTCT ATTTCTTGCG ACCCTAACTT       650

TATTTTCTCA ATTGACCACC ACCCCATGAC CGTCATTGAG ATGGACGGTG       700

TTAATACCCA ATCTATGACC GTAGATTCGA TCCAAATCTT CGCAGGTCAA       750

CGATACTCAT TTGTCATGCA AGCCAACCAA CCAGTTGGAA ATTACTGGAT       800

CCGCGCTAAA CCTAATGTTG GCAACACAAC TTTCCTTGGA GGCCTGAACT       850

CCGCTATCTT GCGATACGTG GGAGCCCCTG ACCAAGAACC GACCACTGAC       900

CAAACACCCA ACTCTACACC GCTCGTTGAG GCGAACCTGC GACCCCTCGT       950

CTACACTCCT GTGCCGGGAC AGCCATTCCC TGGCGGTGCT GATATCGTCA      1000

AGAACTTGGC TTTGGGTTTC AATGCCGGGC GTTTCACAAT CAATGGAGCG      1050

TCCCTCACAC CTCCTACAGT CCCTGTCCTG CTCCAGATCC TCAGCGGTAC      1100

TCACAATGCA CAGGATCTTC TCCCGGCAGG AAGCGTGATC GAACTTGAAC      1150

AGAATAAAGT TGTCGAAATC GTTTTGCCCG CTGCGGGCGC CGTTGGCGGT      1200
```

```
CCTCATCCTT TTCACTTGCA TGGTCACAAT TTCTGGGTGG TTCGTAGCGC    1250

CGGTCAAACC ACATACAATT TCAATGATGC TCCTATCCGT GATGTTGTCA    1300

GCATTGGCGG TGCAAACGAT CAAGTCACGA TCCGATTTGT GACCGATAAC    1350

CCTGGCCCAT GGTTCCTTCA CTGTCACATT GACTGGCATT TGGAGGCTGG    1400

ATTCGCTGTC GTCTTTGCGG AGGGAATCAA TGGTACTGCA GCTGCTAATC    1450

CCGTCCCGGC GGCTTGGAAT CAATTGTGCC CGTTGTACGA TGCCTTGAGC    1500

CCGGGTGATA CATGAGGCGC GCC                                1523
``` encoding the laccase B gene was synthesized by McLab Inc. (Molecular Cloning Laboratories, 384 Oyster Point Blvd, Suite 15, South San Francisco, Calif. 94080). The synthetic plasmid DNA was digested with restriction enzymes SpeI and AscI and the 1.5 kb DNA fragment was isolated from gel and cloned into pTrex4 vector which was also digested with SpeI and AscI to create the expression plasmid (pTrex4-laccase-Bopt), which is similar to the expression plasmid shown in FIG. 4 except that the codon optimized laccase B gene replaced the (non-optimized) laccase B gene. The plasmid was transformed biolistically into a *Trichoderma* strain. More than 30 transformants were generated and were transferred to new plates. A total of 20 stable transformants were selected and mycelia were transferred to 30 mls of defined media containing 1 mM copper. The cultures were grown for 4 days at 28° C. Culture broths were centrifuged and supernatants were used for ABTS assay.

Example 11 a. Expression of Laccase D Gene in *Trichoderma*

To construct the expression plasmid for the laccase D gene of the CBS115.075 strain, two primers (SEQ ID No. 63 and SEQ ID No. 64) were used in the Herculase PCR reaction containing genomic DNA template obtained from CBS115.075 strain (see Example 2b). The PCR fragment was purified using the QIAquick spin column and cloned into pENTR/D-TOPO vector. Sixteen clones were amplified using Ready-To-Go PCR beads and four plasmid DNAs were sequenced. The pENTR-laccase D CBS115.075#2 clone was selected. The pENTR-laccase D CBS115.075#2 plasmid (50 ng) was converted to expression plasmid pTrex3g-laccase D, which is similar to the expression plasmid shown in FIG. 1 except that the codon optimized laccase D gene replaced the laccase A gene, in a 10 ul LB clonase II reaction containing 6.5 ul of TE, 1 ul of pTrex3g vector (0.1 mg/ml) and 2 ul of ClonaseII. The expression plasmid was confirmed again by DNA sequencing and transformed biolistically into a *Trichoderma* strain. Forty-five transformants were selected and were transferred to new plates. Mycelia from 28 stable transformants were transferred to 30 mls of defined media containing 0.5 mM copper. The cultures were grown for 4 days at 28° C. Culture broths were centrifuged and supernatants were used for ABTS assay.

b. Expression of the Laccase D Gene in *Trichoderma* as CBH1 Fusion

To construct the expression plasmid for the laccase D gene of the CBS115.075 strain, two primers (GGACTAGT-GTCGCCGTTTACAAACGCGCAATTGGGC-CCGTGGCCGAC, SEQ ID No. 68) and (AAGGCGCGC-CTTAAATAGCAGTTCCTTTCTTAG, SEQ ID No. 69) were designed and obtained from Invitrogen. The primers were used in the Herculase PCR reaction containing genomic DNA of the CBS115.075 strain as the DNA template. The PCR fragment was purified using the QIAquick spin column and digested with restriction enzymes SpeI and AscI and cloned into pTrex4 vector (see U.S. patent application Ser. No. 10/590,956; WO 05/093050) which was also digested with SpeI and AscI to create the expression plasmid (pTrex4-laccase D). The fidelity of the expression plasmid was confirmed by DNA sequencing and transformed biolistically into *Trichoderma* strain. More than 300 transformants were generated and sixty transformants were transferred to new plates. Mycelia of 25 stable transformants were transferred to 30 mls of defined media containing 0.5 mM copper. The cultures were grown for 4 days at 28° C. Culture broths were centrifuged and supernatants were used for ABTS assay.

Example 12

Expression of the laccase D gene in *Trichoderma* as CBH1 fusion using codon optimized synthetic gene.

```
DNA (SEQ ID NO: 70):
ACTAGTGTCG CCGTTTACAA ACGCGCTATT GGACCAGTTG CTGATCTGCA      50

CATCGTTAAC AAGGATTTGG CCCCAGACGG CGTCCAGCGC CCAACTGTTC     100

TGGCCGGTGG AACTTTTCCG GGCACGCTGA TTACCGGTCA AAAGGGCGAC     150

AACTTCCAGC TGAACGTGAT TGATGACCTG ACCGACGATC GCATGTTGAC     200

CCCTACTTCG ATCCATTGGC ATGGTTTCTT CCAGAAGGGA ACCGCCTGGG     250

CCGACGGTCC GGCTTTCGTT ACACAGTGCC CTATTATCGC AGACAACTCC     300

TTCCTCTACG ATTTCGACGT TCCCGACCAG GCGGGCACCT TCTGGTACCA     350

CTCACACTTG TCTACACAGT ACTGCGACGG TCTGCGCGGT GCCTTCGTTG     400
```

-continued

```
TTTACGACCC CAACGACCCT CACAAGGACC TTTATGATGT CGATGACGGT    450
GGCACAGTTA TCACATTGGC TGACTGGTAT CACGTCCTCG CTCAGACCGT    500
TGTCGGAGCT GCTACACCCG ACTCTACGCT GATTAACGGC TTGGGACGCA    550
GCCAGACTGG CCCCGCCGAC GCTGAGCTGG CCGTTATCTC TGTTGAACAC    600
AACAAGAGAT ACCGTTTCAG ACTCGTCTCC ATCTCGTGCG ATCCCAACTT    650
CACTTTTAGC GTCGACGGTC ACAACATGAC GGTTATCGAG GTTGATGGCG    700
TGAATACCCG CCCTCTCACC GTCGATTCCA TTCAAATTTT CGCCGGCCAG    750
CGATACTCCT TTGTGCTGAA TGCCAATCAG CCCGAGGATA ACTACTGGAT    800
CCGCGCTATG CCTAACATCG ACGAAACAC CACTACCCTT GATGGCAAGA    850
ATGCCGCTAT CCTGCGATAC AAGAACGCCA GCGTTGAGGA GCCCAAAACC    900
GTCGGAGGAC CCGCGCAGAG CCCATTGAAC GAGGCCGACC TGCGACCTCT    950
GGTGCCCGCT CCTGTCCCTG GCAACGCAGT TCCTGGTGGT GCGGACATCA   1000
ACCACCGCCT GAACCTGACA TTCAGCAACG GCCTCTTCTC TATCAATAAC   1050
GCATCATTTA CAAACCCCAG CGTCCCTGCC TTGTTGCAGA TTCTTTCCGG   1100
CGCACAAAAC GCTCAGGATC TGCTTCCCAC CGGTTCTTAT ATCGGCTTGG   1150
AGTTGGGCAA GGTCGTTGAA CTCGTGATCC CTCCCTTGGC CGTTGGTGGC   1200
CCCCATCCAT TCCACTTGCA CGGCCACAAC TTTTGGGTCG TCCGAAGCGC   1250
TGGTTCTGAC GAGTATAATT TCGACGATGC AATTTTGCGC GACGTGGTCA   1300
GCATTGGCGC GGGAACTGAC GAGGTTACTA TCCGTTTTGT CACTGATAAC   1350
CCAGGCCCTT GGTTCCTCCA TTGCCACATC GACTGGCACC TCGAAGCCGG   1400
CCTCGCCATT GTTTTCGCCG AAGGCATCAA TCAAACCGCA GCCGCCAACC   1450
CGACTCCACA GGCCTGGGAC GAACTCTGCC CCAAGTATAA CGGACTCTCC   1500
GCTTCCCAGA AAGTGAAGCC CAAGAAGGGA ACAGCCATCT AAGGCGCGCC   1550
``` encoding the laccase D gene (based on the gene from CBS115.075) was synthesized by DNA2.0 Inc. (1455 Adams Drive, Menlo Park, Calif. 94025). The synthetic plasmid DNA was digested with restriction enzymes SpeI and AscI and The 1.5 kb DNA fragment was isolated from gel and cloned into pTrex4 vector which was also digested with SpeI and AscI to create the expression plasmid (pTrex4-laccase-Dopt). The plasmid was transformed biolistically into a *Trichoderma* strain, Forty transformants were transferred to new plates. A total of 24 stable transformants were selected and mycelia were transferred to 30 mls of defined media containing 0.5 mM copper. The cultures were grown for 4 days at 28° C. Culture broths were centrifuged and supernatants were used for ABTS assay.

Example 13

Expression of the Laccase D Gene in *Bacillus* as BCE103 Fusion Using Codon Optimized Synthetic Gene

```
DNA (SEQ ID NO: 71):
GGATCCTGAA GCTATCGGTC CGGTTGCAGA TTTACACATC GTAAACAAAG    50
ATCTTGCACC TGACGGCGTT CAACGTCCAA CTGTACTTGC TGGTGGAACA   100
TTCCCTGGTA CACTTATTAC TGGTCAAAAA GGTGACAACT TCCAATTAAA   150
CGTAATTGAC GATCTTACAG ATGACCGTAT GCTTACACCG ACTTCAATTC   200
ACTGGCACGG TTTCTTTCAA AAAGGAACAG CATGGGCTGA TGGTCCTGCA   250
TTCGTTACAC AATGTCCAAT CATTGCTGAT AACTCTTTCC TTTACGATTT   300
TGACGTTCCT GATCAAGCTG GTACATTCTG GTATCACTCA CACTTATCCA   350
CACAATACTG CGATGGACTT CGCGGAGCTT TCGTAGTTTA CGACCCAAAC   400
```

```
                          -continued
GATCCTCATA AAGACCTTTA CGATGTAGAT GATGGTGGAA CAGTTATCAC        450

ATTAGCTGAT TGGTACCATG TACTTGCTCA AACAGTTGTA GGTGCAGCTA        500

CACCAGATTC AACACTTATC AATGGATTAG GACGTTCTCA AACTGGTCCT        550

GCTGACGCAG AACTTGCTGT AATCTCTGTT GAACATAACA AACGTTACAG        600

ATTCCGTCTT GTTAGCATTT CTTGCGATCC AAACTTCACA TTTTCAGTTG        650

ACGGACATAA CATGACAGTT ATCGAAGTAG ATGGTGTAAA CACACGTCCA        700

CTTACTGTAG ACTCTATCCA AATCTTCGCA GGACAACGTT ACTCATTCGT        750

ATTAAACGCA AATCAACCAG AAGATAACTA CTGGATTCGT GCAATGCCAA        800

ACATCGGACG TAACACTACA ACTCTTGACG GCAAAAACGC AGCTATTCTT        850

CGTTACAAAA ACGCTTCTGT TGAAGAACCT AAAACAGTTG GTGGACCAGC        900

ACAATCACCA CTTAACGAAG CTGACTTACG TCCACTGGTT CCAGCACCTG        950

TACCTGGAAA CGCTGTACCA GGAGGTGCTG ATATTAATCA TAGACTTAAC        100

CTTACTTTCT CTAACGGTCT GTTCTCAATC AACAACGCTT CATTCACAAA       1050

TCCTTCAGTT CCAGCACTTT TACAAATTCT TAGCGGTGCA CAAAATGCTC       1100

AGGATCTTTT ACCAACTGGA TCTTACATTG GTCTTGAACT GGGTAAAGTA       1150

GTTGAATTAG TAATTCCTCC GCTTGCTGTA GGTGGACCAC ATCCTTTCCA       1200

TCTTCACGGT CATAACTTCT GGGTTGTACG TTCTGCTGGT TCAGATGAAT       1250

ACAACTTCGA TGACGCAATT CTTCGTGATG TTGTATCTAT TGGTGCTGGA       1300

ACAGATGAAG TAACTATTCG TTTCGTAACA GATAACCCTG GTCCTTGGTT       1350

CTTACATTGT CATATCGATT GGCATCTTGA AGCTGGACTT GCTATTGTTT       1400

TCGCTGAAGG AATCAATCAA ACAGCTGCAG CTAACCCAAC ACCTCAAGCA       1450

TGGGACGAAT TATGTCCAAA ATACAACGCA CTTTCTCCAG GAGATACTTA       1500

Figure 6:
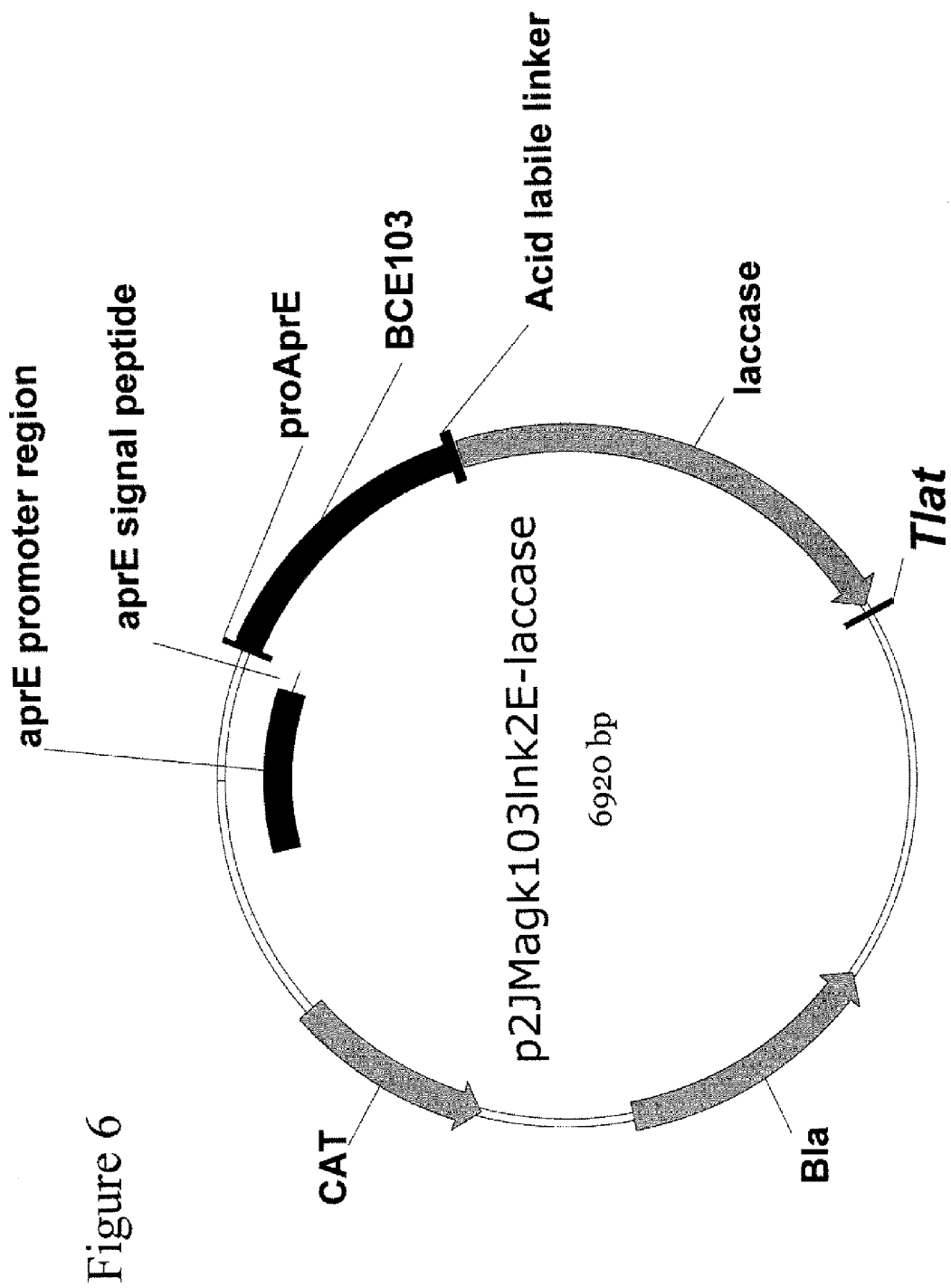
FIG. 6 is a schematic of the *Bacillus* expression plasmid (p2JMagk103lnk2E-laccase) for codon optimized laccase D gene fused to the gene encoding BCE103, used in Example 13.

AAAGCTT                                                     1507
``` encoding the laccase D gene (based on the gene from CBS115.075) was synthesized by DNA2.0 Inc. (1455 Adams Drive, Menlo Park, Calif. 94025). The synthetic plasmid DNA was digested with restriction enzymes BamHI and HindIII and the 1.5 kb DNA fragment was isolated from a gel and ligated into the p2JMagk103lnk2 vector (see US20050202535A1) digested with the same two restriction enzymes to create the expression plasmid p2JMagk103lnk2E-laccase (FIG. 6). The plasmid was transformed into a *B. subtilis* strain (degUHY32, oppA, DspoIIE, DaprE, DnprE, Depr, DispA, Dbpr, Dvpr, DwprA, DmprybfJ, DnprB, amyE::xylRPxylAcomK-ermC) (see US20050202535A1). Two transformants were selected on Luria Broth agar plates with 5 mg/ml chloramphenicol, and then to select for clones with higher gene copy numbers, colonies were serially streaked on Luria Broth agar plates with 25 mg/ml chloramphenicol until rapid colony growth was obtained. The amplified transformants were inoculated into 30 ml MBD medium (see US20050202535A1) containing 0.5 mM copper. The cultures were grown for 60 h at 37'C. Culture broths were centrifuged and supernatants were used for ABTS assay.

Example 14

Bleaching of Solubilized Indigo with Different Laccases

An assay for the bleaching of the solubilized indigo substrate by laccase/mediator combinations was performed in a 96-well microtitre plate as follows A saturated solution of indigo in N-methylpyrrolidone (NMP) was prepared by stirring indigo (30 mg) in NMP (10 ml) at room temperature for 5 hours. The NMP solution was diluted 10-fold into an aqueous buffer solution resulting in a blue solution. For example, dilution into 50 mM sodium acetate buffer at pH 5, or 50 mM sodium phosphate buffer at pH 7. Solutions were shaken well immediately before use.

The assay for the bleaching of the solubilized indigo substrate was performed in a 96-well microtitre plate whereby each well received the soluble indigo solution in 50 mM sodium acetate buffer at pH 5 (180 uL), laccase (10 ppm enzyme) and mediator solution (from a 20 mM stock solution in methanol). The total volume of each well was adjusted to 200 uL with deionzed water. A control containing laccase only was run in duplicate. The plate was sealed and incubated at 50° C. for 2 hours at 800 rpm on a heated agitator (Thermomixer, Eppendorf). Following this period, the plates were unsealed and a solution of ascorbic acid (20 uL of a 10% aqueous solution) added to each well in order to reduce the oxidized forms of the mediators. The extent of indigo bleaching was then assessed by determining the absorbance for each well at 600 nm using a microtitre plate reader. The lower the absorbance reading, the greater the extent of indigo bleaching.

Figure 7:
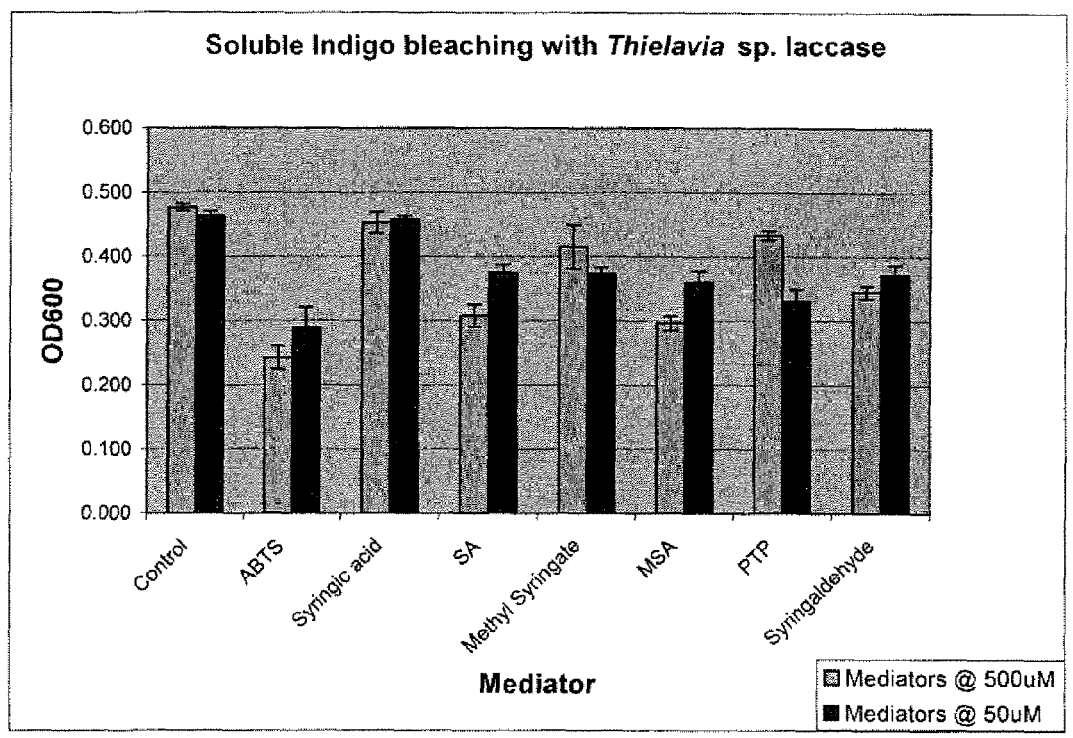
FIG. 7 is a bar graph showing the results of bleaching soluble indigo using a *Thielavia* sp. laccase and a variety of mediators at 50 and 500 uM concentrations.

FIG. 7 shows the results for a *Thielavia* sp. laccase (Ecostone LCC10, AB enzymes, Darmstadt, Germany). The mediators used were 2,2'-azino-bis(3-ethylbenzthiazoline-6-sulphonic acid (ABTS), syringic acid, 4-carboxamido-2,6- dimethoxyphenol (SA), methyl syringate (MS), 4-(N-methyl carboxamido)-2,6-dimethoxyphenol (MSA), 10-(carboxypropyl)-phenothiazine (PTP) and syringaldehyde. The changes in absorbance at 600 nm relative to control are listed in Table 1 where the greatest change in absorbance corresponds to the largest extent of indigo bleaching.

At a mediator concentration of 500 uM, the most effective mediator for indigo bleaching was ABTS, followed by the N-methyl amide (MSA) and the unsubstituted amide, 4-carboxamido-2,6-dimethoxyphenol (SA). At the lower mediator concentration of 50 uM, ABTS was still the most effective mediator, with the remaining mediators being more or less equivalent. The exception was syringic acid, which bleached soluble indigo no more effectively than the control condition.

TABLE 1

Change in absorbance at 600 nm following bleaching of soluble indigo using a *Thielavia* sp. laccase and a variety of mediators at 500 and 50 uM concentrations (n = 2).

| | 500 mM Concentration | | 50 mM Concentration | |
|---|---|---|---|---|
| Mediator | ΔA600 | Std Dev | ΔA600 | Std Dev |
| Control | 0 | 0.008 | 0 | 0.010 |
| ABTS | 0.235 | 0.019 | 0.174 | 0.032 |
| Syringic acid | 0.024 | 0.017 | 0.005 | 0.009 |
| SA | 0.170 | 0.018 | 0.088 | 0.014 |
| Methyl Syringate | 0.062 | 0.035 | 0.090 | 0.012 |
| MSA | 0.181 | 0.013 | 0.103 | 0.018 |
| PTP | 0.044 | 0.009 | 0.132 | 0.020 |
| Syringaldehyde | 0.132 | 0.012 | 0.092 | 0.017 |

Example 15

Soluble Indigo Bleaching Assay with Different Laccases at Two pH Values

Laccases derived from *Myceliophtora* (Denilite® II, Novozymes, Bagsvaerd, Denmark), *Thielavia* (Ecostone LCC10, AB enzymes, Darmstadt, Germany) and *Cerrena* sp. were assessed for their ability to bleach solubilized indigo in conjunction with low molecular weight mediators at two pH values.

Figure 8:
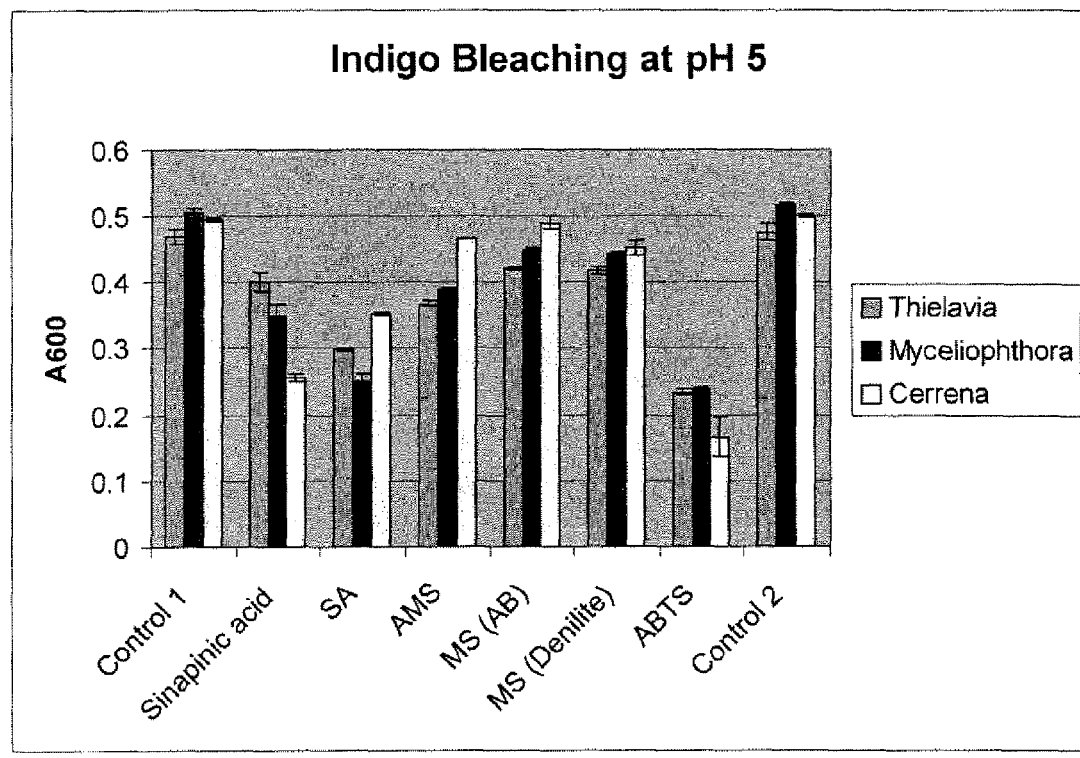
FIG. 8 is a bar graph showing the results of bleaching of soluble indigo using a *Thielavia, Myceliophthora* and *Cerrena* sp. laccase and a variety of mediators at pH 5.
Figure 9:
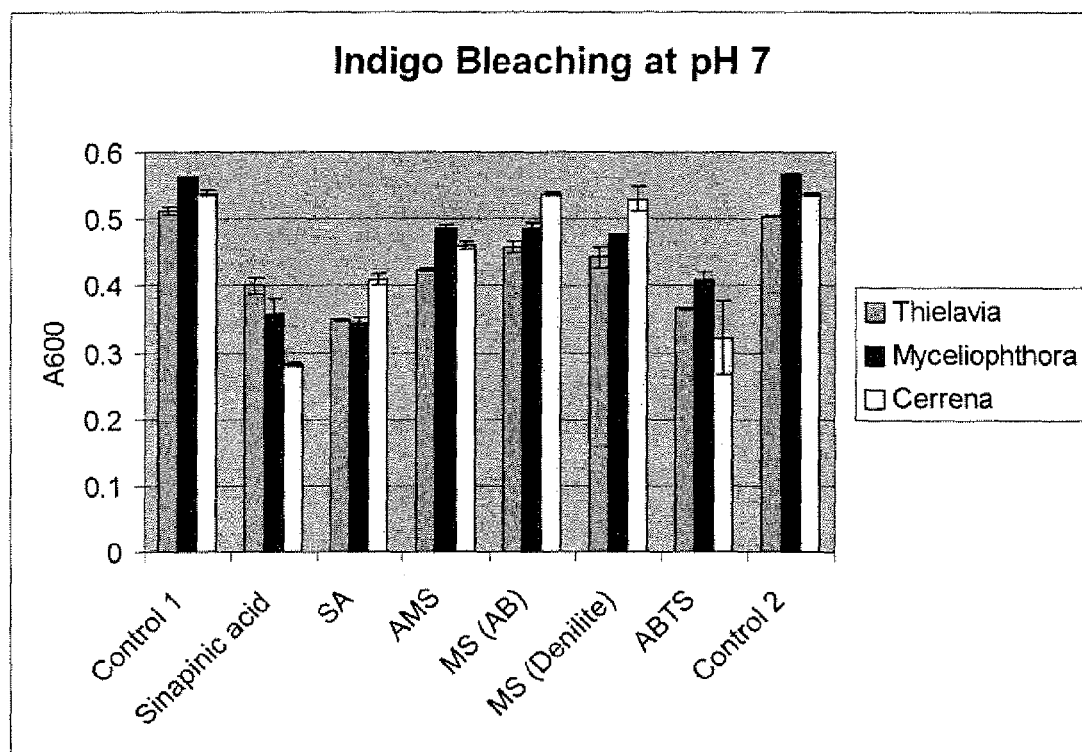
FIG. 9 is a bar graph showing the results of bleaching of soluble indigo using a *Thielavia, Myceliophthora* and *Cerrena* sp. laccase and a variety of mediators at pH 7.

Bleaching of solubilized indigo in 96-well microtitre plates was performed as described in Example 14, using 3 different laccases at pH values of 5 and 7. The mediators used were sinapinic acid, 4-carboxamide-2,6-dimethoxyphenol (SA), methyl 4-acetyl syringate (AMS), methyl syringate (MS) and 2,2'-azino-bis(3-ethylbenzthiazoline-6-sulphonic acid (ABTS). FIGS. 8 and 9 shows the results of soluble indigo bleaching at pH values of 5 and 7 using three laccases derived from *Myceliophtora, Thielavia* and *Cerrena* sp. respectively. These data are tabulated in Tables 2 and 3.

TABLE 2

Change in absorbance at 600 nm relative to a control following bleaching of soluble indigo using laccases from *Thielavia, Myceliophtora* and *Cerrena* sp. at pH 5, at a mediator concentration of 250 uM.

| | Laccase | | | | | |
|---|---|---|---|---|---|---|
| | *Thielavia* | | *Myceliophtora* | | *Cerrena* | |
| Mediator | ΔA$_{600}$ | Std Dev | ΔA$_{600}$ | Std Dev | ΔA$_{600}$ | Std Dev |
| Control 1 | 0 | 0.016 | 0 | 0.010 | 0 | 0.005 |
| Sinapinic acid | 0.068 | 0.019 | 0.157 | 0.020 | 0.240 | 0.007 |

TABLE 2-continued

Change in absorbance at 600 nm relative to a control following bleaching of soluble indigo using laccases from *Thielavia, Myceliophtora* and *Cerrena* sp. at pH 5, at a mediator concentration of 250 uM.

| | Laccase | | | | | |
|---|---|---|---|---|---|---|
| | *Thielavia* | | *Myceliophtora* | | *Cerrena* | |
| Mediator | ΔA$_{600}$ | Std Dev | ΔA$_{600}$ | Std Dev | ΔA$_{600}$ | Std Dev |
| SA | 0.170 | 0.011 | 0.254 | 0.013 | 0.142 | 0.005 |
| AMS | 0.100 | 0.012 | 0.117 | 0.007 | 0.028 | 0.003 |
| MS (AB) | 0.048 | 0.011 | 0.057 | 0.007 | 0.005 | 0.011 |
| MS (Denilite) | 0.050 | 0.013 | 0.061 | 0.007 | 0.043 | 0.013 |
| ABTS | 0.234 | 0.012 | 0.267 | 0.008 | 0.329 | 0.031 |
| Control 2 | −0.007 | 0.017 | −0.011 | 0.007 | −0.006 | 0.005 |

TABLE 3

Change in absorbance at 600 nm relative to a control following bleaching of soluble indigo using laccases from *Thielavia, Myceliophtora* and *Cerrena* sp. at pH 7, at a mediator concentration of 250 uM.

| | Laccase | | | | | |
|---|---|---|---|---|---|---|
| | *Thielavia* | | *Myceliophtora* | | *Cerrena* | |
| Mediator | ΔA600 | Std Dev | ΔA600 | Std Dev | ΔA600 | Std Dev |
| Control 1 | 0 | 0.008 | 0 | 0.001 | 0 | 0.006 |
| Sinapinic acid | 0.112 | 0.015 | 0.204 | 0.020 | 0.257 | 0.005 |
| SA | 0.162 | 0.006 | 0.220 | 0.009 | 0.128 | 0.010 |
| AMS | 0.087 | 0.006 | 0.078 | 0.005 | 0.077 | 0.007 |
| MS (AB) | 0.053 | 0.010 | 0.076 | 0.006 | 0.000 | 0.006 |
| MS (Denilite) | 0.069 | 0.017 | 0.086 | 0.001 | 0.008 | 0.018 |
| ABTS | 0.145 | 0.006 | 0.155 | 0.014 | 0.215 | 0.056 |
| Control 2 | 0.007 | 0.006 | −0.004 | 0.001 | 0 | 0.005 |

Example 16

Purification and Determination of Specific Activity

The laccase D optimized gene (SEQ ID NO:70) was expressed using the expression system described in co-pending application U.S. 60/984,430 (entitled "Signal Sequences and co-expressed chaperones for improved heterologous protein production in a host cell" filed 1 Nov. 2007) in 14 liter fermenters. Fermentation broth from was harvested at 184 hours and concentrated by ultra filtration (UFC 20070245). The concentrate was diafiltered into 25 mM sodium acetate, pH4.0 buffer. Then 500 ml of the diafiltered UFC sample was loaded on to an ion exchange column containing Poros HS-20 resin (Applied Biosystems, 20×275 mm column) equilibrated with 25 mM sodium acetate buffer, pH 4.0. The column was washed with 10 column volumes of 25 mM sodium acetate buffer, pH 4.0. The laccase D protein was eluted from the column using a salt gradient (12 column volumes) from 40 mm to 80 mM sodium chloride in 25 mM sodium acetate buffer, pH 4.0. Fractions containing laccase activity were pooled and further concentrated using an Amicon 400 mL stir cell with a 10K membrane. Total protein was measure by SDS protein gel using BSA as standard as 4 mg/ml (>90% pure). The laccase sample was diluted 10,000 fold with water and stored at RT for 18 hours and at 4° C. for more than 24 hours. ABTS activity was measured as 8570 units/ml. The specific activity of the recombinant laccase D is then calculated by dividing 8570 units/ml by 4 mg/ml resulting in 2140 units/mg of protein which is 100 times more activity than the Stachybotrys laccase (16 u/mg), see Mander et al, Appl. Environ. Microbiol. (2006) 72:5020-5026). Thus, this enzyme results in lower copper discharge into the environment than other laccases, e.g., Stachybotrys laccase, by virtue of the high specific activity.

Example 17

Procedure for Denim Bleaching

Mediators 4-hydroxy-3,5-dimethoxybenzamide (syringamide, SA) was purchased from Punjab Chemicals & Crop Protection Limited (Mumbai, India). 4-hydroxy-3,5-dimethoxybenzonitrile (syringonitrile, SN) was acquired from StereoChemical, Inc., (Newark, Del.) or Punjab Chemicals & Crop Protection Limited (Mumbai, India).

Enzyme

Laccase enzyme, derived from *Cerrena unicolor* (Example 16, 8570 U/ml, 4 mg protein/ml) was used in the experiments.

Procedure

The enzyme incubations were done in an ATLAS LP 2 Launder-O-meter at different conditions in relation to pH, temperature, enzyme concentration and mediator concentration.

Reactions were carried out in 500 ml stainless steel reaction vessels containing 100 ml of liquid. To each vessel five (7×7 cm) stonewashed denim swatches (ACG denim style 80270) and 6 steel balls of 6 mm diameter were added. The reactions vessels were closed and entered into the launder-O-meter that was pre-heated to the desired temperature. The incubation was carried out for 30 minutes after which the swatches were washed with 'running' tap water, spin dried in an AEG IPX4 centrifuge and dried with an Elna Press Electronic iron at program cotton and evaluated.

Stonewashing of Denim

Denim, 12 legs weighing approximately 3 kg, was desized in a Unimac UF 50 washing machine under the following conditions:

Desizing for 15 minutes at 10:1 liquor ratio 50° C. with 0.5 g/l (15 g) of Optisize 160 amylase (Genencor) and 0.5 g/l (15 g) of a non-ionic surfactant (e.g. Rucogen BFA, (Rudolf Chemie) or Ultravon GPN, (Huntsman))

2 cold rinses for 5 minutes at 30:1 liquor ratio.

Following desizing the denim was stonewashed in a Unimac UF 50 washing machine under the following conditions:

Cold rinse for 5 minutes at 10:1 liquor ratio

Stonewashing for 60 minutes at 10:1 liquor ratio 55° C. with 1 kg of pumice stone, citrate buffer (30 g tri-sodium citrate dihydrate and 30 g citric acid monohydrate) and 35 g IndiAge 2XL cellulase (Genencor).

2 cold rinses for 5 minutes at 30:1 liquor ratio.

The denim was dried in a Miele Novotronic T494C household fabric dryer. From the denim legs, swatches of 7×7 cm were cut.

Evaluation of Denim Swatches

The color of the five denim swatches is measured with a Minolta Chromameter CR 310 in the CIE Lab color space with a D 65 light source. Measurements were done before and after laccase treatment and the results of the five swatches were averaged. The total color difference (TCD) is calculated. The total color difference can be calculated with the formula: $TCD=\sqrt{(\Delta L)^2+(\Delta a)^2+(\Delta b)^2}$.

Evaluation of Denim Legs

Denim legs were evaluated with a Minolta Chromameter CR 310 in the CIE Lab color space with a D 65 light source. Measurements were done only after laccase treatment. For each denim leg 8 measurements are taken and the result of the 12 legs (96 measurements) was averaged. The total color difference ($\Delta E$) is calculated from the difference between the initial and final CIE L*a*b* values according to the formula $$\Delta E=(\Delta L^2+\Delta a^2+\Delta b^2)^{1/2}$$

Example 18

Effect of Temperature on the Recombinant Laccase D Bleaching Performance (Unimac)

Laccase Bleaching of Stonewashed Denim:

Denim, 12 legs approximately 3 kg, was desized and stonewashed as described in example 17. After stonewashing a laccase treatment was done in a Unimac UF 50 washing machine according to the following process:

30 minutes at 10:1 liquor ratio, pH 6 (21 g monosodium phosphate and 5 g adipic acid, laccase D laccase) or pH 4.8 (8.6 g monosodium phosphate and 16.8 g of adipic acid Base 268 laccase)

laccase (laccase D or Novoprime Base 268)

mediator (syringamide (SA) and syringonitrile (SN))

After laccase treatment the denim use rinsed twice in cold water for 5 minutes at 30:1 liquor ratio.

The laccase experiments were carried out and the results are presented in Tables 4 and 5.

TABLE 4

| Laccase D concentration | Mediator | Mediator concentration | Temperature (° C.) | Bleaching level (CIE L) |
|---|---|---|---|---|
| 0.05 g/l/0.4 U/ml | SA | 0.33 mM | 60 | 35.6 |
| 0.05 g/l/0.4 U/ml | SN | 0.47 mM | 60 | 35.9 |
| 0.05 g/l/0.4 U/ml | SA | 0.33 mM | 40 | 35.6 |
| 0.05 g/l/0.4 U/ml | SN | 0.47 mM | 40 | 35.7 |

TABLE 5

| Novoprime base 268 concentration | Mediator concentration | Temperature (° C.) | Bleaching level (CIE L) |
|---|---|---|---|
| 0.05 g/l | 0.023 g/l | 60 | 35.9 |
| 0.05 g/l | 0.023 g/l | 40 | 33.7 |

The recombinant laccase D has better performance at lower temperatures than currently available commercial laccases. The laccase D (in the presence of mediator) provides a bleaching effect at temperatures below 60° C., preferably between 40° C. and 60° C. Thus, the laccase may provide an energy benefit to the textile processor.

Example 19

Effect of Recombinant Laccase Enzyme and Mediator Concentration on Bleaching Performance (Launder-O-Meter)

The effect of laccase and mediator concentration was evaluated running the experiments in the table below at pH 6 (50 mM monosodium phosphate buffer pH adjusted with sodium hydroxide 4N solution) and a temperature of 60° C.

The experiments were done with syringamide (SA)—and syringonitrile (SN) mediator. 100 ml buffer was added to a beaker with five swatches, 7×7 cm. The total weight 12 g, (denim:liquor ratio=1:8). Laccase and mediator concentrations were used as indicated in the tables below.

TABLE 6

| Laccase enzyme concentration (μl/l) | Activity correspondence (Laccase unit/ g denim) |
|---|---|
| 10 | 0.67 |
| 33 | 2.17 |
| 55 | 3.67 |
| 78 | 5.17 |
| 100 | 6.67 |

TABLE 7

| Mediator Concentration (mM) |
|---|
| 0.10 |
| 0.33 |
| 0.55 |
| 0.78 |
| 1.00 |

The amounts of syringamide or syringonitrile mediator as indicated in the tables below were added to each beaker as a dilution of a 275 mM SA—or—SN stock solution in 98% methanol. The laccase was added to each beaker as indicated in the tables below, as dilution of a 400 units/ml laccase stock solution. The beakers were closed and processed at 60° C. as described in the example 17. The swatches were evaluated as described in example 17.

TABLE 8

LACCASE + SA at 60° C. pH 6

| Laccase (μl/l) | Mediator syringamide (mM) | TCD |
|---|---|---|
| 100 | 1.00 | 5.6 |
| 100 | 1.00 | 6.0 |
| 100 | 0.10 | 2.9 |
| 78 | 0.33 | 4.4 |
| 55 | 1.00 | 6.2 |
| 55 | 0.55 | 5.3 |
| 33 | 0.78 | 5.5 |
| 33 | 0.33 | 4.6 |
| 10 | 1.00 | 3.2 |
| 10 | 0.10 | 2.5 |
| 55 | 0.55 | 5.8 |
| 100 | 0.55 | 5.3 |
| 78 | 0.78 | 5.9 |
| 100 | 0.10 | 3.2 |
| 55 | 0.10 | 3.1 |
| 10 | 0.55 | 3.6 |

TCD = total color difference

TABLE 9

LACCASE + SN at 60° C. pH 6

| Laccase (μl/l) | Mediator syringonitrile (mM) | TCD |
|---|---|---|
| 100 | 1.00 | 7.6 |
| 100 | 1.00 | 8.1 |
| 100 | 0.10 | 4.1 |
| 78 | 0.33 | 5.6 |
| 55 | 1.00 | 7.0 |
| 55 | 0.55 | 6.0 |
| 33 | 0.78 | 5.5 |
| 33 | 0.33 | 4.4 |
| 10 | 1.00 | 3.8 |
| 10 | 0.10 | 2.7 |
| 55 | 0.55 | 6.3 |
| 100 | 0.55 | 7.1 |
| 78 | 0.78 | 7.1 |
| 100 | 0.10 | 4.0 |
| 55 | 0.10 | 3.5 |
| 10 | 0.55 | 3.4 |

TCD = total color difference

Figure 10:
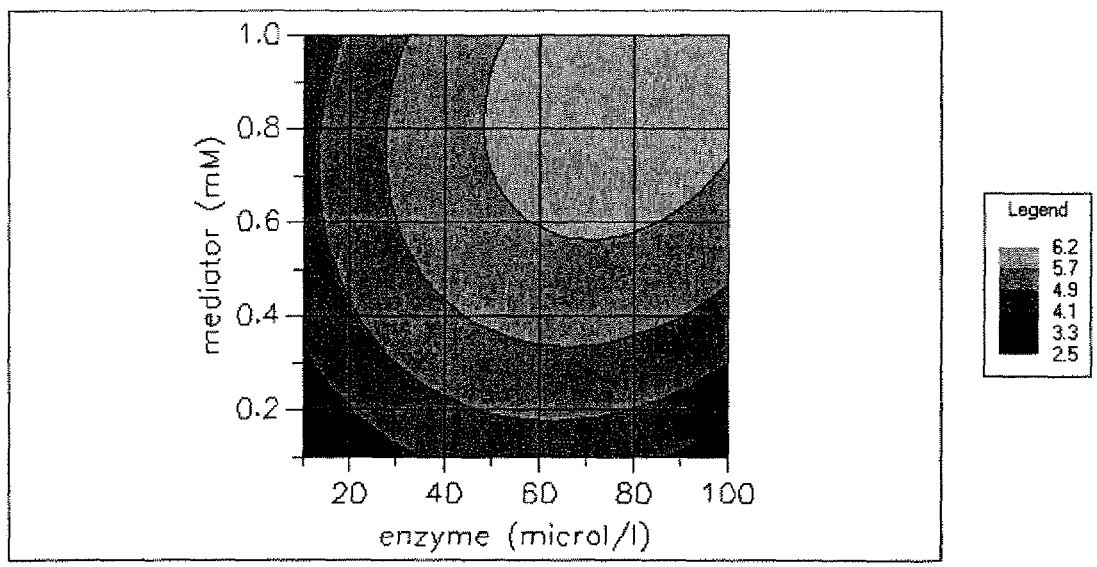
FIG. 10 is a total color difference graph for the recombinant laccase D and syringamide mediator as a function of mediator concentration and enzyme concentration at 60° C. and pH 6.
Figure 11:
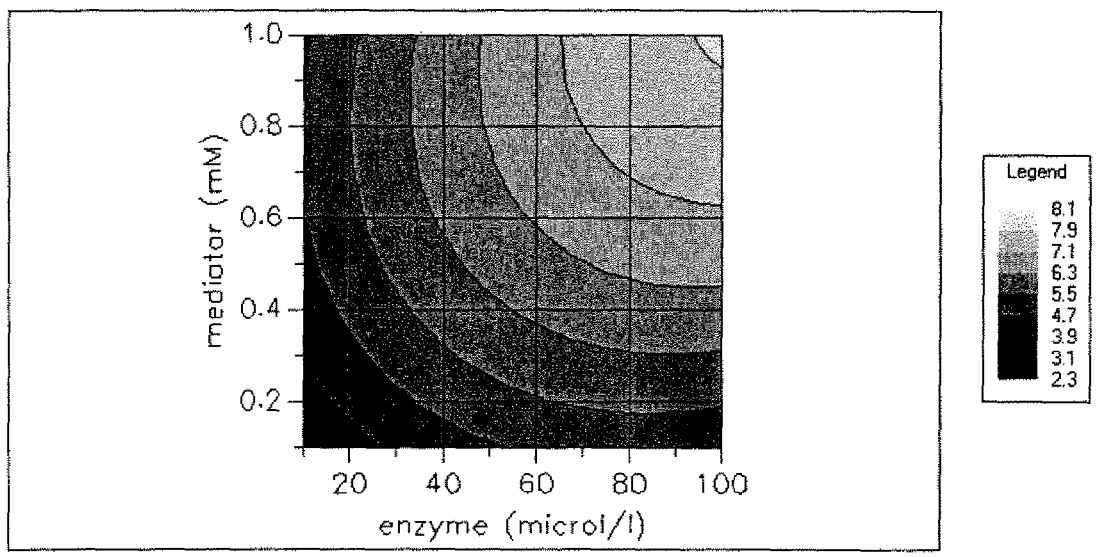
FIG. 11 is a total color difference graph for the recombinant laccase D and syringonitrile mediator as a function of mediator concentration and enzyme concentration at 60° C. and pH 6.

The above Tables and FIGS. 10 and 11 show that you need both enzyme and mediator to get bleaching. Also it shows there is some flexibility in the enzyme/mediator ratio in achieving a certain bleaching level.

Example 20

Recombinant Laccase D Dose Response Effect on the Bleaching Performance (Unimac)

Laccase Bleaching of Stonewashed Denim—
Denim, 12 legs weighing approximately 3 kg, was desized and stonewashed as described in Example 17. After stonewashing, a laccase treatment was done according to the following process: 30 minutes at 10:1 liquor ratio and pH 6 (21 g monosodium phosphate and 5 g adipic acid) and 60° C. with laccase and mediator. After laccase treatment the denim use rinsed twice in cold water for 5 minutes at 30:1 liquor ratio.

The following experiments were carried out.
Syringamide 0.33 mM:

| *Cerrena unicolor* laccase concentration (g/l) | Bleaching level (CIE L) |
|---|---|
| 0.010 | 34.6 |
| 0.05 | 36.2 |
| 0.25 | 36.2 |

Syringonitrile 0.39 mM:

| Laccase D concentration (g/l) | Bleaching level (CIE L) |
|---|---|
| 0.25 | 37.7 |
| 0.4 | 39.5 |
| 0.53 | 38.8 |

The results are shown in the above tables. This shows that with recombinant laccase D and the amide mediator the bleaching level flattens quite quickly. With an enzyme concentration of 0.05 and 0.25 the same bleaching level is obtained. For the recombinant laccase D and the nitrile mediator the bleaching level increases up to 0.4 g/l, where there appears to be an optimum.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety.

The invention claimed is:

1. A process for bleaching dye in solution comprising treating the dye in solution with a laccase polypeptide having at least 95% amino acid sequence identity to the polypeptide of SEQ ID NO: 14 and an effective mediator.

2. The process according to claim 1, wherein the mediator is selected from the group consisting of acetosyringone, syringaldehyde, syringamide, methyl syringamide, 2-hydroxyethyl syringamide, methyl syringate, syringonitrile, dimethylsyringamide, and syringic acid.

3. A process for bleaching fabric comprising contacting the fabric with a laccase polypeptide having at least 95% amino acid sequence identity to the polypeptide of SEQ ID NO: 14.

4. The process of claim 3 further comprising contacting the fabric with a mediator selected from the group consisting of acetosyringone, syringaldehyde, syringamide, methyl syringamide, 2-hydroxyethyl syringamide, methyl syringate, syringonitrile, dimethylsyringamide, and syringic acid.

5. The process according to claim 3, wherein the fabric is dyed with a vat dye.

6. The process according to claim 3, wherein the fabric is a cellulosic fabric, a mixture of cellulosic fibers, or a mixture of cellulosic and synthetic fibers.

7. The process according to claim 3, wherein the fabric is denim.

* * * * *